United States Patent [19]

Hayakawa et al.

[11] Patent Number: 5,286,723
[45] Date of Patent: Feb. 15, 1994

[54] SPIRO COMPOUND

[75] Inventors: Isao Hayakawa; Shohgo Atarashi; Masazumi Imamura; Youichi Kimura, all of Chiba, Japan

[73] Assignee: Daiichi Seiyaku Co., Ltd., Tokyo

[21] Appl. No.: 902,560

[22] Filed: Jun. 22, 1992

Related U.S. Application Data

[63] Continuation of Ser. No. 400,835, Oct. 30, 1989, abandoned.

[30] Foreign Application Priority Data

Aug. 31, 1988 [JP] Japan ................. 63-217638
Sep. 14, 1988 [JP] Japan ................. 63-231318
Nov. 24, 1988 [JP] Japan ................. 63-296985
Jun. 19, 1989 [JP] Japan ................. 63-156316

[51] Int. Cl.$^5$ .............. A61K 31/55; A61K 31/47; C07D 223/32; C07D 223/14
[52] U.S. Cl. .................... 514/213; 514/211; 514/221; 514/224.2; 514/230.5; 514/278; 540/543; 544/6; 546/15; 546/16
[58] Field of Search .............. 544/71, 231, 6; 540/543; 546/15, 16; 514/210, 226.8, 227.5, 230.5, 221, 249, 258, 229.8, 312, 278, 211

[56] References Cited

U.S. PATENT DOCUMENTS 3,418,324 12/1968 Rice et al. ................ 260/326
4,011,233 3/1977 Dubs et al. ............... 206/306
4,430,335 2/1984 Strupczewski et al. ..... 548/408
4,777,175 10/1988 Culbertson et al. ........ 514/312

FOREIGN PATENT DOCUMENTS 0116347 8/1984 European Pat. Off.
0153163 8/1985 European Pat. Off.
0172651 2/1986 European Pat. Off.
0297858 1/1989 European Pat. Off.
1961474 7/1970 Fed. Rep. of Germany.
1470010 8/1970 Fed. Rep. of Germany.
2756360 6/1978 Fed. Rep. of Germany.
3322530 1/1985 Fed. Rep. of Germany.
3522405 1/1987 Fed. Rep. of Germany ...... 544/105
3721745 1/1988 Fed. Rep. of Germany.
0210092 12/1983 Japan ................. 14/230.2
8802627 4/1988 PCT Int'l Appl.
984119 2/1965 United Kingdom.

OTHER PUBLICATIONS

Masuzawa et al., Chemical Abstracts, vol. 108, 1988, Abstract 112468p.
Keily et al., J. Med. Chem., 31, 2004–2008, 1988.
Wentland et al., J. Med. Chem., 1988, 31, 1694–1697.
Chemical Abstracts, 106:13 640 (1987).
Journal of Medicinal Chemistry, 1972, vol. 15, No. 2, pp. 129–132, 1972.
Chemical Abstracts, vol. 112, Abstract No. 112337, 1989.
Journal of the Chemical Society, Perkin Transactions II, pp. 325–331, 1973.
Chemical Abstracts, vol. 66, Abstract No. 18688c, 1967.
Notification of Defects in Israel Patent Applications No. 91474, 1993.
English Translation of Notification of Defects in Israel Patent Applications No. 91474, 1993.
Abstract of Israeli Patent 78528, 1986.
Claims of JP 61243077, 1986.
Abstract of Israeli Patent 69601, 1967.

Primary Examiner—John M. Ford
Assistant Examiner—P. K. Sripada
Attorney, Agent, or Firm—Sughrue, Mion, Zinn, Macpeak & Seas

[57] ABSTRACT

The present invention relates to spiro compounds of general formula I:

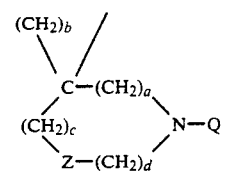

wherein the substituents are herein below defined.

The present invention relates to antibacterial spiro compounds which are of value as drugs for humans, veterinary drugs or drugs for use in fish culture or as preservatives, and to antibacterial compositions containing one or more of the same compounds as active ingredients.

34 Claims, No Drawings

SPIRO COMPOUND

This is a continuation of application Ser. No. 07/400,835, filed Oct. 30, 1989, now abandoned.

FIELD OF THE INVENTION

The present invention relates to antibacterial spiro compounds which are of value as drugs for humans, veterinary drugs or drugs for use in fish culture or as preservatives, and to antibacterial compositions containing one or more the same compounds as active ingredients.

BACKGROUND OF THE INVENTION

A variety of derivatives of synthetic antibacterial compounds are known. However, many of the highly active derivatives are not absorbed well when orally administered.

The inventor of the present invention diligently endeavored to develop quinolone derivatives which possess high antibacterial activity and show efficient oral absorption rate.

SUMMARY OF THE INVENTION

The present invention relates to spiro compounds of general formula I:

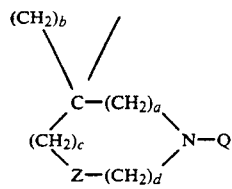

wherein a means an integer equal to 0 or 1, b an integer equal to 2 through 5, inclusive, c an integer equal to 0 or 1 and d an integer equal to 0 through 2, inclusive; Z means

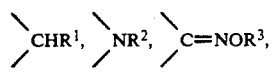

an oxygen atom or a sulfur atom, wherein $R^1$ is a hydrogen atom, an amino group, a monoalkylamino group of 1 to 6 carbon atoms, a dialkylamino group containing 1 to 6 carbon atoms per alkyl, a hydroxyl group, an alkoxy group of 1 to 6 carbon atoms or a hydroxyalkyl group of 1 to 6 carbon atoms; $R^2$ is a hydrogen atom, an alkyl group of 1 to 6 carbon atoms, a hydroxyalkyl group of 1 to 6 carbon atoms, a haloalkyl group of 1 to 6 carbon atoms, a formyl group or an alkylcarbonyl group of 2 to 7 carbon atoms, and $R^3$ is a hydrogen atom or an alkyl group of 1 to 6 carbon atoms; Q represents a partial structure of formula II

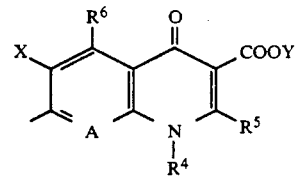

wherein $R^4$ means an alkyl group of 1 to 6 carbon atoms, an alkenyl group of 2 to 6 carbon atoms, a haloalkyl group of 1 to 6 carbon atoms, a substituted or unsubstituted cycloalkyl group of 3 to 6 carbon atoms, a substituted or unsubstituted aryl group, a substituted or unsubstituted heteroaryl group, an alkoxy group of 1 to 6 carbon atoms or an alkylamino group of 1 to 6 carbon atoms; $R^5$ means a hydrogen atom or an alkyl group of 1 to 6 carbon atoms; $R^6$ means a hydrogen atom, a substituted or unsubstituted amino group, a hydroxyl group, an alkoxy group of 1 to 6 carbon atoms or a halogen atom; A means a nitrogen atom or

wherein $R^7$ is a hydrogen atom, an alkyl group of 1 to 6 carbon atoms, a halogen atom, an alkoxy group of 1 to 6 carbon atoms, a haloalkyl group of 1 to 6 carbon atoms or a cyano group; $R^4$ may, taken together with $R^5$ and/or $R^7$, form a substituted or unsubstituted ring which can include an oxygen, nitrogen or sulfur atom, wherein the substituent is an alkyl group of 1 to 6 carbon atoms or a haloalkyl group of 1 to 6 carbon atoms; X means a halogen atom, preferably a fluorine atom; Y means a hydrogen atom, an alkyl group of 1 to 6 carbon atoms, an alkoxyalkyl group of 1 to 6 carbon atoms, a phenylalkyl group containing 1 to 6 carbon atoms in its alkyl moiety, a dihaloboron group, a phenyl group, an acetoxymethyl group, a pivaloyloxymethyl group, an ethoxycarbonyloxy group, a choline group, a dimethylaminoethyl group, a 5-indanyl group, a phthalidinyl group, a 5-substituted-2-oxo-1,3-dioxazol- 4-ylmethyl group or a 3-acetoxy-2-oxobutyl group, and salts thereof. More particularly, the invention relates to spiro compounds of general formula I wherein a means 1, b 2, c 0 and d 1 and Z means

and salts thereof. The invention also relates to spiro compounds of general formula I wherein a means 1, b 3, c 0, and d 1, and Z means

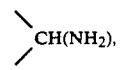

and the salts thereof. The invention further relates to spiro compounds of general formula I wherein a means 1, b 2, c 0 and d 2 and Z means

and salts thereof. More particularly, the invention relates to spiro compounds of general formula I wherein said spiro compounds are optically pure. More particularly, the invention relates to 7-(7-amino-5-azaspiro[2,4-]heptan-5-yl)-1-cyclopropyl-6,8-difluoro-1,4-dihydro-4-oxoquinoline-3-carboxylic acid, 7-(7-amino-5-azaspiro-[2,4]heptan-5-yl)-8-chloro-1-cyclopropyl-6-fluoro-1,4-dihydro-4-oxoquinoline-3-carboxylic acid, 7-(7-amino-5-azaspiro[2,4]heptan-5-yl)-1-cyclopropyl-6-fluoro-1,4-dihydro-4-oxoquinoline-3-carboxylic acid, 7-(7-amino-5-azaspiro[2,4]heptan-5-yl)-6-fluoro-1-(2,4-difluorophenyl)-1,4-dihydro-4-oxoquinoline-3-carboxylic acid, 7-(7-amino-5-azaspiro[2,4]heptan-5-yl)-1-cyclo-propyl-6-fluoro-1,4-dihydro-4-oxo-1,8-naphthyridine-3-carboxylic acid, 10-(7-amino-5-azaspiro[2,4]heptan-5-yl)-9-fluoro-2,3-dihydro-3-(S)-methyl-7-oxo-7H-pyrido[1,2,3-de][1,4] benzoxazine-6-carboxylic acid, 1-cyclopropyl-7-(4,7-diazaspiro[2,5]octan-7-yl)-6-fluoro-1,4-dihydro-4-oxoquinoline-3-carboxylic acid, 7-(7-amino-5-azaspiro[2,4]heptan-5-yl)-1-cyclopropyl-6-fluoro-8-methyl-1,4-dihydro-4-oxoquinoline-3-carboxylic acid, 7-(7-hydroxy-5-azaspiro[2,4]heptan-5-yl)-8-chloro-1-cyclopropyl-6-fluoro-1,4-dihydro-4-oxoquinoline-3-carboxylic acid, 7-(7-amino-5-azaspiro[2,4]heptan-5-yl)-1-(2-methyl-2-propyl)-6-fluoro-1,4-dihydro-4-oxo-1,8-naphthyridine-3-carboxylic acid, 7-(7-hydroxyimino-5-azaspiro[2,4]heptan-5-yl)-8-chloro-1-cyclopropyl-6-fluoro-1,4-dihydro-4-oxoquinoline-3-carboxylic acid, 1-cyclopropyl-6,8-difluoro-7-(8-hydroxymethyl-6-azaspiro[3,4]octan-6-yl)-4-oxo-1,4-dihydroquinoline-3-carboxylic acid, 1-cyclopropyl-6,8-difluoro-7-(4-hydroxymethyl-2-azaspiro[4,4]nonan-2-yl)-4-oxo-1,4-dihydroquinoline-3-carboxylic acid, 1-cyclopropyl-6,8-difluoro-7-(4-hydroxymethyl-2-azaspiro[4,5]decan-2-yl)-4-oxo-1,4-dihydroquinoline-3-carboxylic acid, 7-(8-amino-6-azaspiro[3,4]octan-6-yl)-1-cyclopropyl-6,8-difluoro-4-oxo-1,4-dihydroquinoline-3-carboxylic acid, 10-(8-amino-6-azaspiro[3,4]octan-6-yl)-9-fluoro-2,3-dihydro-3-(S)-methyl-7-oxo-7H-pyrido[1,2,3-de][1,4]benzoxazine-6-carboxylic acid, or 7-(4-amino-2-azaspiro-[4,4]nonan-2-yl)-1-cyclopropyl-6,8-difluoro-4-oxo-1,4 -dihydroquinoline-3-carboxylic acid. In a further aspect, the present invention relates to an antibacterial composition containing a compound of general formula I as an active ingredient.

DETAILED DESCRIPTION OF THE INVENTION

The compounds of the present invention are characterized in that each of them is a cyclic amine compound having a spiro ring and also in that the "7-equivalent position" of a quinolone derivative has been attached thereto. The term "7-equivalent position" of a quinolone derivative means, for example, the 7-position of optionally substituted 4-oxoquinoline-3-carboxylic acid compounds and 4-oxo-1,8-naphthyridine-3-carboxylic acid compounds, the 10-position of 7-oxopyrido[1,2,3-de][1,4]benzoxazine-6-carboxylic acid or the 8-position of benzo[ij]quinolizine-2-carboxylic acid.

The spiro ring should be in the range of 3-membered through 6-membered rings, of which 3-membered and 4-membered rings are preferred.

The ring size of the cyclic amine exclusive of the spiro ring should be in the range of 4- to 8-membered rings, of which 5-membered and 6-membered rings are preferred. This cyclic amine is attached through its nitrogen atom to the "7-equivalent position" of a quinolone derivative.

This cyclic amine may further contain one or more hetero-atom, such as oxygen, sulfur and nitrogen, of which nitrogen is preferred. This nitrogen atom may be substituted, for example, by an alkyl group of 1 to 6 carbon atoms, a hydroxyalkyl group of 1 to 6 carbon atoms, a haloalkyl group of 1 to 6 carbon atoms, a formyl group and an alkylcarbonyl group of 2 to 7 carbon atoms.

The followings are some of the examples of cyclic amine structures bearing spirocyclic ring; 5-azaspiro[2,4]heptane structure, 6-azaspiro[3,4]octane structure, 2-azaspiro[4,4]nonane structure, 2-azaspiro[4,5]decane structure, 5-azaspiro[2,5]octane structure, 6-azaspiro[2,5]octane structure, 6-azaspiro[3,5]nonane structure, 7-azaspiro[3,5]nonane structure, 7-azaspiro[4,5]decane structure, 8-azaspiro[4,5]decane structure, 2-azaspiro[5,5]undecane structure, 3-azaspiro[5,5]undecane structure, 4,7-diazaspiro[2,5]octane structure, 5,8-diazaspiro[3,5]nonane structure, 6,9-diazaspiro[4,5]decane structure, 7,10-diazaspiro[5,5]undecane structure, 7-aza-4-oxaspiro[2,5]octane structure, 8-aza-5-oxaspiro[3,5]nonane structure, 9-aza-6-oxaspiro[4,5]decane structure, 7-aza-4-thiaspiro[2,5]octane structure, 8-aza-5-thiaspiro[3,5]nonane structure, 9-aza-6-thiaspiro[4,5]decane structure, 7-aza-4-thiaspiro[2,5]octane-4-oxide structure, 8-aza-5-thiaspiro[3,5]nonane-5-oxide structure, and 9-aza-6-thiaspiro[4,5]decane-6-oxide structure.

When an additional hetero-atom such as oxygen, sulfur or nitrogen exists in the ring of said cyclic amine or particularly when such hetero-atom is not existent, there may exist polar substituent groups on the amine ring, such as, for example, amino, monoalkylamino groups of 1 to 6 carbon atoms, dialkylamino groups containing 1 to 6 carbon atoms per alkyl, aminoalkyl groups of 1 to 6 carbon atoms, the amino moiety of which is or is not substituted by alkyl of 1 to 6 carbon atoms or hydroxyalkyl of 1 to 6 carbon atoms, hydroxy, hydroxyalkyl groups of 1 to 6 carbon atoms, hydroxyimino, and alkoxy groups of 1 to 6 carbon atoms. Preferred are the amino groups.

These substituents on the spiro-substituted cyclic amine are or are not protected by appropriate protective groups. Such protective groups can be selected from among those which are commonly employed. For example, suitable protective groups include alkoxycarbonyl groups such as tert-butoxycarbonyl, and 2,2,2-trichloroethoxycarbonyl, aralkyloxycarbonyl groups such as benzyloxycarbonyl, p-methoxybenzyloxycarbonyl, and p-nitrobenzyloxycarbonyl, acyl groups such as acetyl, methoxyacetyl, trifluoroacetyl, chloroacetyl, pivaloyl, formyl, and benzoyl, alkyl or aralkyl groups such as tert-butyl, benzyl, p-nitrobenzyl, p-methoxybenzyl, and triphenylmethyl, ether groups such as methoxymethyl, tert-butoxymethyl, tetrahydropyranyl, and 2,2,2-trichloroethoxymethyl, and silyl groups such as trimethylsilyl, isopropyldimethylsilyl, tert-butyldimethylsilyl, tribenzylsilyl, and tert-butyldiphenylsilyl.

When a substituent other than the spiro ring exists on the spiro-substituted cyclic amine and the carbon atom to which the substituent is attached is an asymmetric carbon atom, stereoisomers of the cyclic amine exist. If such a cyclic amine as a mixture of stereoisomers is used as a substituent for the "7-equivalent position", the resulting spiro compound I may be a mixture of diastereomers if the second asymmetric carbon atom exists in the spiro compound. A mixture of diastereomers is a mixture of compounds dissimilar in physical constants and cannot be utilized as a drug. In such cases, the cyclic amine should be fractionated into isomers prior to the reaction.

When the product spiro compound I is a racemic compound, the racemate may be used as it is. However, there are cases in which an optically active form is biologically more useful than the racemate. In such cases, the racemate should be subjected to optical resolution.

For example, as for the antimicrobial activity of the two enantiomers having a 7-amino-5-azaspiro[2,4]heptane structure, one of them has more potent antimicrobial activity than the other. It has been revealed that the derivative of the 7-(S)-amino-5-azaspiro[2,4-]heptane is the more potent enantiomer. This fact was confirmed by the X-ray crystallographycal analysis of the one of the isomer of 7-(7-tert-butoxycarbonylamino-5-azaspiro[2,4]heptane-5-yl)-8-chloro-1-cyclopropyl-6-fluoro-1,4-dihydro-4-oxoquinoline-3-carboxylic acid which gives the more potent isomer of 7-(7-amino-5-azaspiro[2,4]heptane-5-yl)-8-chloro-1-cyclopropyl-6-fluoro-1,4-dihydro-4-oxoquinoline-3-carboxylic acid.

The cyclic amine substituted by a spiro ring can be synthesized in the following manner.

Taking 7-amino-5-azaspiro[2,4]heptane as an example, ethyl acetoacetate is first reacted with 1,2-dibromoethane in the presence of a base to give ethyl 1-acetyl-1-cyclopropanecarboxylate. Then, using bromine, the acetyl group of this compound is brominated to give ethyl 1-bromoacetyl-1-cyclopropanecarboxylate. This bromoacetyl compound is then cyclized with benzylamine to give 5-benzyl-4,7-dioxo-5-azaspiro[2,4]heptane. When this compound is reacted with hydroxylamine hydrochloride, the ketone in 7-position is converted to an oxime to give 5-benzyl-7-(hydroxyimino)-4-oxo-5-azaspiro[2,4]heptane. This oxime is reduced with lithium aluminum hydride to give a spiro ring-containing aminopyrrolidine compound, viz., 7-amino-5-benzyl-5-azaspiro[2,4]heptane. When the benzyl group of this compound is eliminated by an ordinary procedure, such as catalytic hydrogenolysis, 7-amino-5-azaspiro[2,4]heptane which is a racemic compound, is obtained When this cleavage of the benzyl group is preceded after the amino group is protected by the reaction of 2-(tert-butoxycarbonylamino)-2-phenylacetonitrile (hereinafter referred to briefly as BOC-ON), 7-tert-butoxycarbonylamino-5-azaspiro[2,4]heptane is obtained.

Optical isomers of 7-amino-5-azaspiro[2,4]heptane can be obtained in the following manner.

First, 7-amino-5-benzyl-5-azaspiro[2,4]heptane is reacted with (R)-N-p-toluenesulfonylpropyl chloride to give 7-[(R)-N-p-toluenesulfonylpropyl]amino-5-benzyl-5-azaspiro[2,4]heptane. This compound is then reacted with benzyl chlorocarbonate to give 7-[(R)-N-p-toluenesulfonylpropyl]amino-5-benzyloxycarbonyl-5-azaspiro[2,4]heptane. This product can be fractionated into optically active compounds by high performance liquid chromatography (hereinafter referred to briefly as HPLC). After resolution, each compound is treated with 2N sodium hydroxide, whereupon the proline moiety and the benzyloxycarbonyl group are cleaved off to give the corresponding optically active 7-amino-5-azaspiro[2,4]heptane.

It has also been found that when the cyclization of ethyl 1-bromoacetyl-1-cyclopropanecarboxylate is carried out using an optically active 1-phenethylamine in lieu of benzylamine, the subsequent optical resolution of the racemic compound is facilitated.

The following procedure is an alternative synthesis starting from 1-acetyl-1-cyclopropanecarboxylic ester. At first, the ester of 1-acetyl-1-cyclopropanecarboxylic ester is cleaved by acidic or basic hydrolysis or by catalytic hydrogenation. This free acid is reacted with R-(+)-1-phenylethylamine to give N-[1-(R)-phenylethyl]-1-acetyl-1-cyclopropylcarboxamide, an amide derivative. Then, the carbonyl moiety of acetyl group thereof is converted to a ketal group and, thus, N-[1-(R)-phenylethyl]-1-(1,1-ethylenedioxyethyl)-1-cyclopropanecarboxamide is obtained. The methyl group adjacent to the ketal group thereof is then halogenated, for example, N-[1-(R)-phenylethyl]-1-(1,1-ethylenedioxyethyl)ethyl)-1-cyclopropanecarboxamide is converted to N-[1-(R)-phenylethyl]-1-(2-bromo-1,1-ethylenedioxyethyl)-1-cyclopropanecarboxamide. This halomethyl compound is cyclized in the presence of base to 4,7-dioxo-5-[1-(R)-phenylethyl]-5-azaspiro[2,4-]heptane-7-ethyleneacetal which is a pyrrolidone derivative bearing a spiro cyclic ring and ketal function. The ketal function thereof can be cleaved by a known hydrolysis procedure to give 4,7-dioxo-5-[1-(R)-phenylethyl]-5-azaspiro[2,4]heptane. This compound can lead to the spirocyclic amine by the previously mentioned procedure.

The synthesis of 4,7-diazaspiro[2,5]octane is discussed below. Cyclopropane-1,1-diamide is first reacted with bromine and a base to give cyclopropane-1,1-dibromoamide which, in turn, is treated with an alkoxide to give a spiro hydantoin, namely, 4,6-diazaspiro[2,4]heptane-5,7-dione. This compound is then treated with alkali to give 1-aminocyclopropanecarboxylic acid. The amino group of this compound is protected with a tert-butoxycarbonyl group to give 1-(tert-butoxycarbonylamino)-1-cyclopropanecarboxylic acid, which is then condensed with glycine ethyl ester in the presence of dicyclohexylcarbodiimide to give ethyl (1-tert-butoxycarbonylamino-1-cyclopropylcarbonylamino)acetate. After removal of the amino-protecting group, the above compound is cyclized under heating to give a spiro ring-containing diketopiperazine compound, namely, 4,7-diazaspiro[2,5]octane-5,8-dione. This compound is reduced with lithium aluminum hydride to give a spiro ring-containing piperazine compound, namely, 4,7-diazaspiro[2,5]octane.

The synthesis of the cyclic amine derivative bearing a spirocyclic ring can be achieved by the method exemplified as follows. Condensation of a cyclic alkyl ketone and malonic acid diester in the presence of titanium tetrachloride gives a cycloalkylidenemalonic acid diester. The reaction of this cycloalkylidenemalonic acid diester and nitromethane in the presence of base yields Michael adduct, e.g., (1-nitromethyl-1-cycloalkyl)malonic acid diester. The reductive cyclization of (1-nitromethyl-1-cycloalkyl)malonic acid diester gives pyrrolidonecarboxylic acid ester bearing a spirocyclic ring, e.g., if the spirocyclic ring is 4-membered ring, 7-oxo-6-azaspiro[3,4]octane-8-carboxylic acid ester is obtained. For this reductive cyclization, catalytic reduction is more convenient. However, other chemical reduction methods are also applicable. This pyrrolidonecarboxylic acid ester can be converted to the cyclic amine derivative bearing a spirocyclic ring and tert-butoxycarbonylamino substituent by the Crutius reaction in tert-butanol of the free carboxylic acid which is obtained by the cleavage of the ester by the known method such as hydrolysis or hydrogenolysis. The reduction of the pyrrolidone bearing a spirocyclic ring and an amino substituent after the removal of tert-butoxycarbonyl group gives pyrrolidine derivative having a spirocyclic ring and an amino substituent. The reduction of pyrrolidonecarboxylic acid ester with metal hydrides such as lithium aluminum hydride gives pyrrolidine derivative bearing a spirocyclic ring and a hydroxymethyl substituent.

Quinolone derivatives to be bound to such a spiro ring-containing cyclic amine include bicyclic compounds such as 1,4-dihydro-4-oxoquinoline-3-carboxylic acid, and 1,4-dihydro-4-oxo-1,8-naphthyridine-3-carboxylic acid, and tricyclic compounds such as 2,3-dihydro-7-oxo-7H-pyrido[1,2,3-de][1,4]benzoxazine-6-carboxylic acid, 2,3-dihydro-7-oxo-7H-pyrido[1,2,3-de][1,4]benzothiazine-6-carboxylic acid, 6,7-dihydro-1,7-dioxo-1H,5H-benzo[ij]quinolizine-2-carboxylic acid, and 6,7-dihydrobenzo[ij]quinolizine-2-carboxylic acid, tetracyclic compound such as 9,1-epoxymethano-5-oxo-5H-thiazolo[3,2-a]quinoline-4-carboxylic acid. The partial structures are illustrated below.

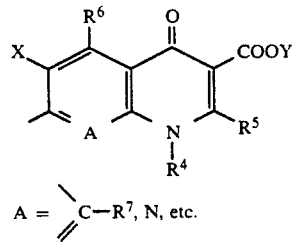

$A = \diagdown C-R^7$, N, etc.

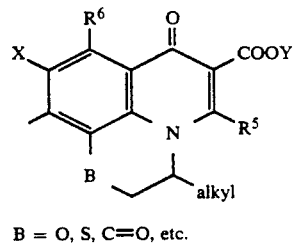

B = O, S, C=O, etc.

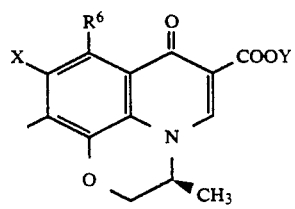

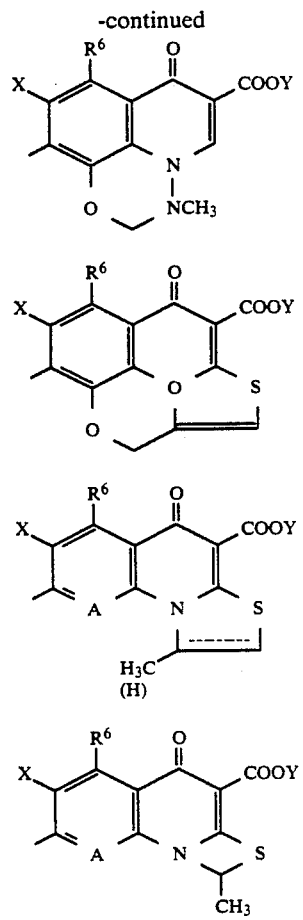

Referring to 1,4-dihydro-4-oxoquinoline-3-carboxylic acid and 1,4-dihydro-4-oxo-1,8-naphthyridine-3-carboxylic acid compounds, the substituent in 1-position may, for example, be a lower alkyl group of 1 to 6 carbon atoms, such as ethyl, isopropyl and tert-butyl, a haloalkyl group of 1 to 6 carbon atoms, such as 2-fluoroethyl, a lower alkenyl group of 2 to 6 carbon atoms, such as vinyl and isopropenyl, a cycloalkyl group of 3 to 6 carbon atoms which is or is not substituted, such as cyclopropyl, cis-2-methylcyclopropyl and 2-gem-dihalocyclopropyl, an aryl or heteroaryl group which is or is not substituted, such as 4-fluorophenyl, 2,4-difluorophenyl and 2-fluoro-4-pyridyl, an alkoxy group of 1 to 6 carbon atoms, such as methoxy and ethoxy, or an alkylamino group of 1 to 6 carbon atoms, such as methylamino and ethylamino. Among these substituent groups, ethyl, 2-fluoroethyl, vinyl, cyclopropyl, cis-2-methylcyclopropyl, 4-fluorophenyl, 2,4-difluorophenyl, 2-fluoro-4-pyridyl, methoxy and methylamino are preferred.

The substituent in 2-position is preferably a hydrogen atom or an alkyl group of 1 to 6 carbon atoms, such as methyl, ethyl and propyl.

The preferred substituent group in 5-position is a hydrogen atom, an amino group, an unsubstituted mono-$C_{1-6}$alkylamino or di-$C_{1-6}$alkylamino group, such as methylamino, ethylamino, isopropylamino, dimethylamino and diethylamino, a hydroxyl group, a halo-$C_{1-6}$ alkyl group, a $C_{1-6}$alkoxy group such as methoxy and ethoxy, or a halogen atom.

The 6-position is preferably substituted by a halogen atom, particularly fluorine or chlorine.

The 8-position of quinoline derivatives is or is not substituted. Suitable substituents include a halogen atom, a $C_{1-6}$alkyl group, a $C_{1-6}$alkoxy group, a halo-$C_{1-6}$alkyl group and a cyano group. Preferred species are chlorine, fluorine, methyl and methoxy.

Regarding the quinolone structure, it may not only be a bicyclic structure but may be a tricyclic or tetracyclic structure formed between the 1-position and either the 8-position or the 2-position or between the 1-position and each of the 8- and 2-positions of the quinoline ring. The ring formed in such cases is preferably in the range of 4-membered to 7-membered rings and more desirably a 5- or 6-membered ring.

The ring so formed may include nitrogen, oxygen and sulfur atoms. Moreover, not only single bonds but also double bonds may be contained, and the ring may have aromaticity. Furthermore, such rings are or are not substituted by $C_{1-6}$alkyl or halo-$C_{1-6}$alkyl groups.

Regarding tricyclic quinolone derivatives, taking 2,3-dihydro-7-oxo-7H-pyrido[1,2,3-de][1,4]benzoxazine-6-carboxylic acid as an example, the 3-position may be substituted by an alkyl group of 1 to 6 carbon atoms which is preferably be in S-configuration. The 9-position is preferably substituted by a halogen atom which is preferably fluorine or chlorine. The above status of substitution may equally apply to other tricyclic quinolone derivatives such as 2,3-dihydro-7-oxo-7H-pyrido[1,2,3-de][1,4]benzothiazine-6-carboxylic acid and 6,7-dihydro-1H,5H-benzo[ij]quinolizine-2-carboxylic acid as well. In the case of 3-alkyl-7-oxo-2,3-dihydro-7H-pyrido[3,2,1-ij]-1,3,4-benzoxadiazine-6-carboxylic acid, the 9-position is preferably substituted by a halogen atom which is preferably fluorine or chlorine.

Preferred quinolone derivatives which are to be attached to said spiro ring-containing cyclic amine are 1,4-dihydro-4-oxoquinoline-3-carboxylic acid compounds.

The spiro ring-containing cyclic amine can be introduced into such a quinolone derivative by the processes described in European Patent (EP)-A-167,763, EP-A-195,841, EP-A-160,578 and EP-A-206,283.

The processes for production of the present compounds are described below by way of reaction schemes.

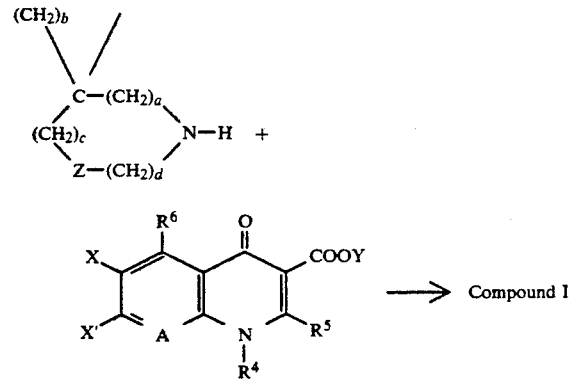

wherein a, b, c, d, Z, A, $R^4$, $R^5$, $R^6$, Y and X are as defined hereinbefore; X' means a halogen atom, preferably a fluorine atom. Thus, when the spiro ring-containing cyclic amine is reacted with a 7-haloquinolone derivative, the nitrogen atom of the pyrrolidine ring is bound to the 7-position of the quinolone ring to give the desired quinolone derivative.

In the starting material quinolone derivative, for example, 1-cyclopropyl-6-fluoro-7-halo-1,4-dihydro-4-oxoquinoline-3-carboxylic acid, the halogen atom in the 7-position may be chlorine or fluorine. These starting compounds can be synthesized by the methods disclosed in EP-A-167,763 and EP-A-195,841. Other quinolone materials can also be synthesized by known processes.

(For example, 7-chloro-6-fluoro-1-ethyl-1,4-dihydro-4-oxo-1,8-naphthyridine-3-carboxylic acid, EP-A-27,752; 9,10-difluoro-3-methyl-7-oxo-2,3-dihydro-7H-pyrido[3,2,1-ij]-1,3,4-benzoxadiazine-6-carboxylic acid, Japan Kokai 88-132891; 9,1-epoxymethano-7,8-difluoro-5-oxo-5H-thiazolo[3,2-a]quinoline-4-carboxylic acid, Japan Kokai 89-117888; 7,8-difluoro-5-oxo-5H-thiazolo[3,2-a]quinoline-3-carboxylic acid, U.S. Pat. No. 4,550,104; 7-halogeno-6-fluoro-1-methyl-4-oxo-4H-[1,3]thiazeto[3,2-a]quinoline-3-carboxylic acid, Japan Kokai 88-107990; 9,10-difluoro-3-methyl-2,3-dihydro-7-oxo-7H-pyrido[1,2,3-de][1,4]benzoxazine-6-carboxylic acid, EP-A-47,005.)

In the method described in EP-A-195,841, the intermediate compound 3-chloro-2,4,5-trifluorobenzoic acid is synthesized in 10 reaction steps. In contrast, the inventor of the present invention developed a process for synthesizing the above compound in one step starting from 3-amino-2,4,5-trifluorobenzoic acid and found that this process was applicable to other benzoic acid derivatives as well.

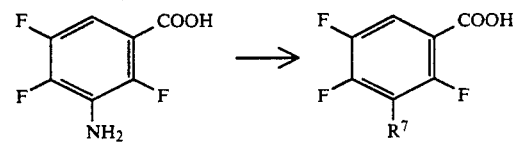

Furthermore, as a starting material to be reacted with the spiro ring-containing amine, it is possible to use a quinolone derivative whose carboxyl group in the 3-position (or 3-equivalent position) has been esterified by a substituted boron compound This ester may, for example, be a compound having the following substituent group in 3-position (or 3-equivalent position) of the quinolone nucleus, forming a chelate with the carbonyl group in 4-position (or 4-equivalent position) of the quinolone ring.

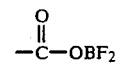

The above fluorine atom may be a different halogen atom or an acetoxy group.

This dihalogenated boron compound can be easily prepared from a free carboxylic acid derivative and an appropriate trihalogenated boron compound such as a boron trifluoride-ether complex.

Thus, the carboxylic acid derivative is suspended or dissolved in an ether, such as diethyl ether, diisopropyl ether, tetrahydrofuran or dioxane, and an excess of boron trifluoride-diethyl ether complex is added. The mixture is stirred at room temperature. The reaction may be conducted at room temperature but, if necessary, under heating up to about 100° C. The reaction is complete in 30 minutes to 24 hours. Since the reaction product generally precipitates out, the precipitate is collected, washed with an inert solvent such as ether and dried under reduced pressure (EP-A-206,283).

The derivatives in which the carboxyl moiety in 3-position (or 3-equivalent position) has been esterified are useful as synthetic intermediates or prodrugs. For example, esters such as an alkyl ester, benzyl ester, alkoxyalkyl ester, phenylalkyl ester or phenyl ester are useful as synthetic intermediates.

The reaction for introduction of the spiro ring-containing cyclic amine is generally carried out in the presence of an acid acceptor. While the acid acceptor may be an organic base or an inorganic base, it is generally preferable to use an organic base.

Preferred organic bases include tertiary amines inclusive of trialkylamines such as triethylamine, tripropylamine, N,N-diisopropylethylamine and tributylamine, aniline compounds such as N,N-dimethylaniline and N,N-diethylaniline, and heterocyclic compounds such as N-methylmorpholine, pyridine and N,N-dimethylaminopyridine.

Examples of inorganic bases include hydroxides, carbonates and hydrogencarbonates of alkali metals such as lithium, sodium and potassium. To be specific, lithium hydroxide, sodium hydroxide, potassium hydroxide, sodium carbonate, potassium carbonate, sodium hydrogen-carbonate and potassium hydrogencarbonate can be mentioned.

It is also possible to use a stoichiometric excess of the starting material spiro ring-containing cyclic amino so that it may serve both as the reactant and the acid acceptor.

The reaction solvent may be any kind of solvent that is inert to the reaction. Suitable solvents include acetonitrile, amides such as N,N-dimethylformamide, N-methyl-2-pyrrolidone and N,N-dimethylacetamide, aromatic hydrocarbons such as benzene, toluene and xylene, aprotic polar solvents such as dimethyl sulfoxide and sulfolane, lower alcohols such as methanol, ethanol, propanol, butanol, amyl alcohol, isoamyl alcohol, cyclohexyl alcohol and 3-methoxybutanol, and ethers such as dioxane, dimethyl cellosolve, diethyl cellosolve and diglyme. When the solvent is water-soluble, it may be used in an admixture with water. In this case, said acid acceptor is preferably an organic base.

The reaction may be conducted in the temperature range of from about 50° to about 180° C., preferably of from about 80° to about 130° C.

The reaction time is 10 minutes to 48 hours and it is generally sufficient to carry out the reaction for 30 minutes to 30 hours.

When the spiro ring-containing cyclic amine is used in the reaction after protection of its nuclear substituent group, subsequent removal of the protective group from the reaction product can be accomplished by a known method suited to the particular protective group, e.g., hydrolysis or hydrogenolysis.

When the carboxyl moiety in 3-position (or 3-equivalent position) is not a free carboxyl group, the derivative can be converted to a free carboxylic acid by a known technique suited to each case. For example, when it is an ester, the conventional hydrolysis reaction using alkali hydroxide in aqueous medium can be employed. In the case of a boron compound, the method using a protonic substance such as an alcohol can be utilized. In this case an acid acceptor may be present in the reaction system. For example, the treatment with ethanol in the presence of triethylamine may be mentioned.

The product spiro compound I can be purified by any or a suitable combination of recrystallization, reprecipitation, treatment with activated carbon, chromatography and other known procedures.

The following compounds are some of the examples of the novel compounds included in the present invention:

7-(7-amino-5-azaspiro[2,4]heptan-5-yl)-1-cyclopropyl-6,8-difluoro-1,4-dihydro-4-oxoquinoline-3-carboxylic acid;

7-(7-amino-5-azaspiro[2,4]heptan-5-yl)-8-chloro-1-cyclopropyl-6-fluoro-1,4-dihydro-4-oxoquinoline-3-carboxylic acid;

7-(7-amino-5-azaspiro[2,4]heptan-5-yl)-1-cyclopropyl-6-fluoro-1,4-dihydro-4-oxoquinoline-3-carboxylic acid;

7-(7-amino-5-azaspiro[2,4]heptan-5-yl)-1-cyclopropyl-6-fluoro-1,4-dihydro-4-oxo-1,8-naphthyridine-3-carboxylic acid;

7-(7-amino-5-azaspiro[2,4]heptan-5-yl)-6,8-difluoro-1-(2-fluoroethyl)-1,4-dihydro-4-oxoquinoline-3-carboxylic acid;

7-(7-amino-5-azaspiro[2,4]heptan-5-yl)-8-chloro-6-fluoro-1-(2-fluoroethyl)-1,4-dihydro-4-oxoquinoline-3-carboxylic acid;

7-(7-amino-5-azaspiro[2,4]heptan-5-yl)-6-fluoro-1-(2-fluoroethyl)-1,4-dihydro-4-oxoquinoline-3-carboxylic acid;

7-(7-amino-5-azaspiro[2,4]heptan-5-yl)-6-fluoro-1-(2-fluoroethyl)-1,4-dihydro-4-oxo-1,8-naphthyridine-3-carboxylic acid;

7-(7-amino-5-azaspiro[2,4]heptan-5-yl)-1-ethyl-6,8-difluoro-1,4-dihydro-4-oxoquinoline-3-carboxylic acid;

7-(7-amino-5-azaspiro[2,4]heptan-5-yl)-8-chloro-1-ethyl-6-fluoro-1,4-dihydro-4-oxoquinoline-3-carboxylic acid;

7-(7-amino-5-azaspiro[2,4]heptan-5-yl)-1-ethyl-6-fluoro-1,4-dihydro-4-oxoquinoline-3-carboxylic acid;

7-(7-amino-5-azaspiro[2,4]heptan-5-yl)-1-ethyl-6-fluoro-1,4-dihydro-4-oxo-1,8-naphthyridine-3-carboxylic acid;

7-(7-amino-5-azaspiro[2,4]heptan-5-yl)-6,8-difluoro-1-(2,4-difluorophenyl)-1,4-dihydro-4-oxoquinoline-3-carboxylic acid;

7-(7-amino-5-azaspiro[2,4]heptan-5-yl)-8-chloro-6-fluoro-1-(2,4-difluorophenyl)-1,4-dihydro-4-oxoquinoline-3-carboxylic acid;

7-(7-amino-5-azaspiro[2,4]heptan-5-yl)-6-fluoro-1-(2,4-difluorophenyl)-1,4-dihydro-4-oxoquinoline-3-carboxylic acid;

7-(7-amino-5-azaspiro[2,4]heptan-5-yl)-6-fluoro-1-(2,4-difluorophenyl)-1,4-dihydro-4-oxo-1,8-naphthyridine-3-carboxylic acid;

7-(7-amino-5-azaspiro[2,4]heptan-5-yl)-6,7-difluoro-1-vinyl-1,4-dihydro-4-oxoquinoline-3-carboxylic acid;

7-(7-amino-5-azaspiro[2,4]heptan-5-yl)-8-chloro-6-fluoro-1-vinyl-1,4-dihydro-4-oxoquinoline-3-carboxylic acid;

7-(7-amino-5-azaspiro[2,4]heptan-5-yl)-6-fluoro-1-vinyl-1,4-dihydro-4-oxoquinoline-3-carboxylic acid;

7-(7-amino-5-azaspiro[2,4]heptan-5-yl)-6-fluoro-1-vinyl-1,4-dihydro-4-oxo-1,8-naphthyridine-3-carboxylic acid;

1-cyclopropyl-7-(4,7-diazaspiro[2,5]octan-7-yl)-6,8-difluoro-1,4-dihydro-4-oxoquinoline-3-carboxylic acid;

8-chloro-1-cyclopropyl-7-(4,7-diazaspiro[2,5]octan-7-yl)-6-fluoro-1,4-dihydro-4-oxoquinoline-3-carboxylic acid;

1-cyclopropyl-7-(4,7-diazaspiro[2,5]octan-7-yl)-6-fluoro-1,4-dihydro-4-oxoquinoline-3-carboxylic acid;

1-cyclopropyl-7-(4,7-diazaspiro[2,5]octan-7-yl-)-6-fluoro-1,4-dihydro-4-oxo-1,8-naphthyridine-3-carboxylic acid;

7-(4,7-diazaspiro[2,5]octan-7-yl)-6,8-difluoro-1-(2-fluoroethyl)-1,4-dihydro-4-oxoquinoline-3-carboxylic acid;

8-chloro-7-(4,7-diazaspiro[2,5]octan-7-yl)-6-fluoro-1-(2-fluoroethyl)-1,4-dihydro-4-oxoquinoline-3-carboxylic acid;

7-(4,7-diazaspiro[2,5]octan-7-yl)-6-fluoro-1-(2-fluoroethyl)-1,4-dihydro-4-oxoquinoline-3-carboxylic acid;

7-(4,7-diazaspiro[2,5]octan-7-yl)-6-fluoro-1-(2-fluoroethyl)-1,4-dihydro-4-oxo-1,8-naphthyridine-3-carboxylic acid;

7-(4,7-diazaspiro[2,5]octan-7-yl)-1-ethyl-6,8-difluoro-1,4-dihydro-4-oxoquinoline-3-carboxylic acid;

8-chloro-7-(4,7-diazaspiro[2,5]octan-7-yl)-1-ethyl-6-fluoro-1,4-dihydro-4-oxoquinoline-3-carboxylic acid;

7-(4,7-diazaspiro[2,5]octan-7-yl)-1-ethyl-6-fluoro-1,4-dihydro-4-oxoquinoline-3-carboxylic acid;

7-(4,7-diazaspiro[2,5]octan-7-yl)-1-ethyl-6-fluoro-1,4-dihydro-4-oxo-1,8-naphthyridine-3-carboxylic acid;

7-(4,7-diazaspiro[2,5]octan-7-yl)-6,8-difluoro-1-(2,4-difluorophenyl)-1,4-dihydro-4-oxoquinoline-3-carboxylic acid;

8-chloro-7-(4,7-diazaspiro[2,5]octan-7-yl)-6-fluoro-1-(2,4-difluorophenyl)-1,4-dihydro-4-oxoquinoline-3-carboxylic acid;

7-(4,7-diazaspiro[2,5]octan-7-yl)-6-fluoro-1-(2,4-difluorophenyl)-1,4-dihydro-4-oxoquinoline-3-carboxylic acid;

7-(4,7-diazaspiro[2,5]octan-7-yl)-6-fluoro-1-(2,4-difluorophenyl)-1,4-dihydro-4-oxo-1,8-naphthyridine-3-carboxylic acid;

7-(4,7-diazaspiro[2,5]octan-7-yl)-6,8-difluoro-1-vinyl-1,4-dihydro-4-oxoquinoline-3-carboxylic acid;

8-chloro-7-(4,7-diazaspiro[2,5]octan-7-yl)-6-fluoro-1-vinyl-1,4-dihydro-4-oxoquinoline-3-carboxylic acid;

7-(4,7-diazaspiro[2,5]octan-7-yl)-6-fluoro-1-vinyl-1,4-dihydro-4-oxoquinoline-3-carboxylic acid;

7-(4,7-diazaspiro[2,5]octan-7-yl)-6-fluoro-1-vinyl-1,4-dihydro-4-oxo-1,8-naphthyridine-3-carboxylic acid;

10-(7-amino-5-azaspiro[2,4]heptan-5-yl)-9-fluoro-3-(S)-methyl-2,3-dihydro-7-oxo-7H-pyrido[1,2,3-de][1,4]benzoxazine-6-carboxylic acid;

10-(4,7-diazaspiro[2,5]octan-7-yl)-9-fluoro-3-(S)-methyl-2,3-dihydro-7-oxo-7H-pyrido[1,2,3-de][1,4]benzoxazine-6-carboxylic acid;

8-(7-amino-5-azaspiro[2,4]heptan-5-yl)-9-fluoro-5-(S)-methyl-6,7-dihydro-1,7-dioxo-1H,5H-benzo[ij]quinolizine-2-carboxylic acid;

8-(4,7-diazaspiro[2,5]octan-7-yl)-9-fluoro-5-(S)-methyl-6,7-dihydro-1,7-dioxo-1H,5H-benzo[ij]quinolizine-2-carboxylic acid;

10-(7-amino-5-azaspiro[2,4]heptan-5-yl)-9-fluoro-3-(S)-methyl-2,3-dihydro-7-oxo-7H-pyrido[1,2,3-de][1,4]benzothiazine-6-carboxylic acid;

10-(4,7-diazaspiro[2,5]octan-7-yl)-9-fluoro-3-(S)-methyl-2,3-dihydro-7-oxo-7H-pyrido[1,2,3-de][1,4]benzothiazine-6-carboxylic acid;

5-amino-7-(7-amino-5-azaspiro[2,4]heptan-5-yl)-1-cyclopropyl-6,8-difluoro-1,4-dihydro-4-oxoquinoline-3-carboxylic acid;

5-amino-7-(7-amino-5-azaspiro[2,4]heptan-5-yl)-8-chloro-1-cyclopropyl-6-fluoro-1,4-dihydro-4-oxoquinoline-3-carboxylic acid;

5-amino-7-(7-amino-5-azaspiro[2,4]heptan-5-yl)-6,8-difluoro-1-(2-fluoroethyl)-1,4-dihydro-4-oxoquinoline-3-carboxylic acid;

5-amino-7-(7-amino-5-azaspiro[2,4]heptan-5-yl)-8-chloro-6-fluoro-1-(2-fluoroethyl)-1,4-dihydro-4-oxoquinoline-3-carboxylic acid;

5-amino-7-(7-amino-5-azaspiro[2,4]heptan-5-yl)-1-ethyl-6,8-difluoro-1,4-dihydro-4-oxoquinoline-3-carboxylic acid;

5-amino-7-(7-amino-5-azaspiro[2,4]heptan-5-yl)-8-chloro-1-ethyl-6-fluoro-1,4-dihydro-4-oxoquinoline-3-carboxylic acid;

5-amino-7-(7-amino-5-azaspiro[2,4]heptan-5-yl)-6,8-difluoro-1-(2,4-difluorophenyl)-1,4-dihydro-4-oxoquinoline-3-carboxylic acid;

5-amino-7-(7-amino-5-azaspiro[2,4]heptan-5-yl)-6,8-chloro-6-fluoro-1-(2,4-difluorophenyl)-1,4-dihydro-4-oxoquinoline-3-carboxylic acid;

5-amino-1-cyclopropyl-7-(4,7-diazaspiro[2,5]octan-7-yl)-6,8-difluoro-1,4-dihydro-4-oxoquinoline-3-carboxylic acid;

5-amino-8-chloro-7-(4,7-diazaspiro[2,5]octan-7-yl)-1-cyclopropyl-6-fluoro-1,4-dihydro-4-oxoquinoline-3-carboxylic acid;

5-amino-7-(4,7-diazaspiro[2,5]octan-7-yl)-6,8-difluoro-1-(2-fluoroethyl)-1,4-dihydro-4-oxoquinoline-3-carboxylic acid;

5-amino-8-chloro-7-(4,7-diazaspiro[2,5]octan-7-yl)-6-fluoro-1-(2-fluoroethyl)-1,4-dihydro-4-oxoquinoline-3-carboxylic acid;

5-amino-7-(4,7-diazaspiro[2,5]octan-7-yl)-1-ethyl-6,8-difluoro-1,4-dihydro-4-oxoquinoline-3-carboxylic acid;

5-amino-8-chloro-7-(4,7-diazaspiro[2,5]octan-7-yl)-1-ethyl-6-fluoro-1,4-dihydro-4-oxoquinoline-3-carboxylic acid;

5-amino-7-(4,7-diazaspiro[2,5]octan-7-yl)-6,8-difluoro-1-(2,4-difluorophenyl)-1,4-dihydro-4-oxoquinoline-3-carboxylic acid;

5-amino-8-chloro-7-(4,7-diazaspiro[2,5]octan-7-yl)-6-fluoro-1-(2,4-difluorophenyl)-1,4-dihydro-4-oxoquinoline-3-carboxylic acid;

5-amino-7-(7-amino-5-azaspiro[2,4]heptan-5-yl)-6,8-difluoro-1-vinyl-1,4-dihydro-4-oxoquinoline-3-carboxylic acid;

5-amino-7-(7-amino-5-azaspiro[2,4]heptan-5-yl)-8-chloro-6-fluoro-1-vinyl-1,4-dihydro-4-oxoquinoline-3-carboxylic acid;

5-amino-7-(4,7-diazaspiro[2,5]octan-7-yl)-6,8-difluoro-1-vinyl-1,4-dihydro-4-oxoquinoline-3-carboxylic acid;

5-amino-8-chloro-7-(4,7-diazaspiro[2,5]octan-7-yl)-6-fluoro-1-vinyl-1,4-dihydro-4-oxoquinoline-3-carboxylic acid;

7-(7-amino-5-azaspiro[2,5]heptan-5-yl)-1-cyclopropyl-6-fluoro-8-methoxy-1,4-dihydro-4-oxoquinoline-3-carboxylic acid;

7-(7-amino-5-azaspiro[2,5]heptan-5-yl)-6-fluoro-1-(2-fluoroethyl)-8-methoxy-1,4-dihydro-4-oxoquinoline-3-carboxylic acid;

7-(7-amino-5-azaspiro[2,5]heptan-5-yl)-1-ethyl-6-fluoro-8-methoxy-1,4-dihydro-4-oxoquinoline-3-carboxylic acid;

7-(7-amino-5-azaspiro[2,5]heptan-5-yl)-6-fluoro-1-(2,4-difluorophenyl)-8-methoxy-1,4-dihydro-4-oxoquinoline-3-carboxylic acid;

7-(7-amino-5-azaspiro[2,5]heptan-5-yl)-6-fluoro-8-methoxy-1-vinyl-1,4-dihydro-4-oxoquinoline-3-carboxylic acid;

7-(7-amino-5-azaspiro[2,5]heptan-5-yl)-1-cyclopropyl-6-fluoro-8-methyl-1,4-dihydro-4-oxoquinoline-3-carboxylic acid;

7-(7-amino-5-azaspiro[2,5]heptan-5-yl)-6-fluoro-1-(2-fluoroethyl)-8-methyl-1,4-dihydro-4-oxoquinoline-3-carboxylic acid;

7-(7-amino-5-azaspiro[2,5]heptan-5-yl)-1-ethyl-6-fluoro-8-methyl-1,4-dihydro-4-oxoquinoline-3-carboxylic acid;

7-(7-amino-5-azaspiro[2,5]heptan-5-yl)-6-fluoro-1-(2,4-difluorophenyl)-8-methyl-1,4-dihydro-4-oxoquinoline-3-carboxylic acid;

7-(7-amino-5-azaspiro[2,5]heptan-5-yl)-6-fluoro-8-methyl-1-vinyl-1,4-dihydro-4-oxoquinoline-3-carboxylic acid;

1-cyclopropyl-7-(4,7-diazaspiro[2,5]octan-7-yl)-6-fluoro-8-methoxy-1,4-dihydro-4-oxoquinoline-3-carboxylic acid;

7-(4,7-diazaspiro[2,5]octan-7-yl)-6-fluoro-1-(2-fluoroethyl)-8-methoxy-1,4-dihydro-4-oxoquinoline-3-carboxylic acid;

7-(4,7-diazaspiro[2,5]octan-7-yl)-1-ethyl-6-fluoro-8-methoxy-1,4-dihydro-4-oxoquinoline-3-carboxylic acid;

7-(4,7-diazaspiro[2,5]octan-7-yl)-1-(2,4-difluorophenyl)-6-fluoro-8-methoxy-1,4-dihydro-4-oxoquinoline-3-carboxylic acid;

7-(4,7-diazaspiro[2,5]octan-7-yl)-6-fluoro-8-methoxy-1-vinyl-1,4-dihydro-4-oxoquinoline-3-carboxylic acid;

1-cyclopropyl-7-(4,7-diazaspiro[2,5]octan-7-yl)-6-fluoro-8-methyl-1,4-dihydro-4-oxoquinoilne-3-carboxylic acid;

7-(4,7-diazaspiro[2,5]octan-7-yl)-6-fluoro-1-(2-fluoroethyl)-8-methyl-1,4-dihydro-4-oxoquinoline-3-carboxylic acid;

7-(4,7-diazaspiro[2,5]octan-7-yl)-1-ethyl-6-fluoro-8-methyl-1,4-dihydro-4-oxoquinoline-3-carboxylic acid;

7-(4,7-diazaspiro[2,5]octan-7-yl)-1-(2,4-difluorophenyl)-6-fluoro-8-methyl-1,4-dihydro-4-oxoquinoline-3-carboxylic acid;

7-(4,7-diazaspiro[2,5]octan-7-yl)-6-fluoro-8-methyl-1-vinyl-1,4-dihydro-4-oxoquinoline-3-carboxylic acid;

7-(8-amino-6-azaspiro[3,4]octan-6-yl)-1-cyclopropyl-6,8-difluoro-1,4-dihydro-4-oxoquinoline-3-carboxylic acid;

7-(8-amino-6-azaspiro[3,4]octan-6-yl)-8-chloro-1-cyclopropyl-6-fluoro-1,4-dihydro-4-oxoquinoline-3-carboxylic acid;

7-(8-amino-6-azaspiro[3,4]octan-6-yl)-6,8-difluoro-1-(2-fluoroethyl)-1,4-dihydro-4-oxoquinoline-3-carboxylic acid;

7-(8-amino-6-azaspiro[3,4]octan-6-yl)-8-chloro-6-fluoro-1-(2-fluoroethyl)-1,4-dihydro-4-oxoquinoline-3-carboxylic acid;

7-(8-amino-6-azaspiro[3,4]octan-6-yl)-1-ethyl-6,8-difluoro-1,4-dihydro-4-oxoquinoline-3-carboxylic acid;

7-(8-amino-6-azaspiro[3,4]octan-6-yl)-8-chloro-1-ethyl-6-fluoro-1,4-dihydro-4-oxoquinoline-3-carboxylic acid;

7-(8-amino-6-azaspiro[3,4]octan-6-yl)-6,8-difluoro-1-(2,4-difluorophenyl)-1,4-dihydro-4-oxoquinoline-3-carboxylic acid;

7-(8-amino-6-azaspiro[3,4]octan-6-yl)-8-chloro-6-fluoro-1-(2,4-difluorophenyl)-1,4-dihydro-4-oxoquinoline-3-carboxylic acid;

7-(8-amino-6-azaspiro[3,4]octan-6-yl)-6,8-difluoro-1-vinyl-1,4-dihydro-4-oxoquinoline-3-carboxylic acid;

7-(8-amino-6-azaspiro[3,4]octan-6-yl)-8-chloro-6-fluoro-1-vinyl-1,4-dihydro-4-oxoquinoline-3-carboxylic acid;

10-(8-amino-6-azaspiro[3,4]octan-6-yl)-9-fluoro-3-(S)-methyl-2,3-dihydro-7-oxo-7H-pyrido[1,2,3-de][1,4]benzoxazine-6-carboxylic acid;

8-(8-amino-6-azaspiro[3,4]octan-6-yl)-9-fluoro-5-(S)-methyl-6,7-dihydro-1,7-dioxo-1H,5H-benzo[ij]quinolizine-2-carboxylic acid;

1-cyclopropyl-7-(5,8-diazaspiro[3,5]nonan-8-yl)-6,8-difluoro-1,4-dihydro-4-oxoquinoline-3-carboxylic acid;

8-chloro-1-cyclopropyl-7-(5,8-diazaspiro[3,5]nonan-8-yl)-6-fluoro-1,4-dihydro-4-oxoquinoline-3-carboxylic acid;

7-(5,8-diazaspiro[3,5]nonan-8-yl)-6,8-difluoro-1-(2-fluoroethyl)-1,4-dihydro-4-oxoquinoline-3-carboxylic acid;

8-chloro-7-(5,8-diazaspiro[3,5]nonan-8-yl)-6-fluoro-1-(2-fluoroethyl)-1,4-dihydro-4-oxoquinoline-3-carboxylic acid;

7-(5,8-diazaspiro[3,5]nonan-8-yl)-1-ethyl-6,8-difluoro-1,4-dihydro-4-oxoquinoline-3-carboxylic acid;

8-chloro-7-(5,8-diazaspiro[3,5]nonan-8-yl)-1-ethyl-6-fluoro-1,4-dihydro-4-oxoquinoline-3-carboxylic acid;

7-(5,8-diazaspiro[3,5]nonan-8-yl)-6,8-difluoro-1-(2,4-difluorophenyl)-1,4-dihydro-4-oxoquinoline-3-carboxylic acid;

8-chloro-7-(5,8-diazaspiro[3,5]nonan-8-yl)-6-fluoro-1-(2,4-difluorophenyl)-1,4-dihydro-4-oxoquinoline-3-carboxylic acid;

7-(5,8-diazaspiro[3,5]nonan-8-yl)-6,8-difluoro-1-vinyl-1,4-dihydro-4-oxoquinoline-3-carboxylic acid;

8-chloro-7-(5,8-diazaspiro[3,5]nonan-8-yl)-6-fluoro-1-vinyl-1,4-dihydro-4-oxoquinoline-3-carboxylic acid;

10-(5,8-diazaspiro[3,5]nonan-8-yl)-9-fluoro-3-(S)-methyl-2,3-dihydro-7-oxo-7H-pyrido[1,2,3-de][1,4]benzoxazine-6-carboxylic acid;

10-(5,8-diazaspiro[3,5]nonan-8-yl)-9-fluoro-3-(S)-methyl-2,3-dihydro-7-oxo-7H-pyrido[1,2,3-de][1,4]benzothiazine-6-carboxylic acid;

8-(5,8-diazaspiro[3,5]nonan-8-yl)-9-fluoro-5-(S)-methyl-6,7-dihydro-1,7-dioxo-1H,5H-benzo[ij]quinolizine-2-carboxylic acid;

7-(7-methylamino-5-azaspiro[2,4]heptan-5-yl)-1-cyclopropyl-6,8-difluoro-1,4-dihydro-4-oxoquinoline-3-carboxylic acid;

7-(7-dimethylamino-5-azaspiro[2,4]heptan-5-yl)-1-cyclopropyl-6,8-difluoro-1,4-dihydro-4-oxoquinoline-3-carboxylic acid; and 8-chloro-1-cyclopropyl-7-(4-methyl-4,7-diazaspiro[2,5]octan-7-yl)-6-fluoro-1,4-dihydro-4-oxoquinoline-3-carboxylic acid.

These quinolone derivatives having a spiro ring-containing cyclic amine moiety are more lipophilic than the corresponding quinolone derivatives having no spiro ring and, as such, are expected to be better absorbed after oral administration and exhibit antibacterial activity.

The pyridonecarboxylic acid derivatives according to the present invention can be used as free compounds, acid addition salts or salts of the carboxyl groups thereof. Examples of such acid addition salts include inorganic acid salts such as hydrochloride, sulfate, nitrate, hydrobromide, hydroiodide, and phosphate, and organic acid salts such as the acetate, methanesulfonate, benzenesulfonate, toluenesulfonate, citrate, maleate, fumarate, and lactate.

Examples of said salts of carboxyl groups include inorganic and organic salts, for example, alkali metal salts such as the lithium salt, sodium salt, potassium salt, alkaline earth metal salts such as magnesium salt and calcium salt, ammonium salt, triethylamine salt, N-methylglucamate and tris(hydroxymethyl)aminomethane salt.

These free compounds, acid addition salts and salts of carboxyl groups of pyridonecarboxylic acid derivatives may exist as hydrates.

On the other hand, quinolone derivatives whose carboxyl moieties are esters are useful as prodrugs or synthetic intermediates.

The esters to be used as prodrugs are esters which are readily cleaved in the body to give free carboxylic acids. Thus, for example, the acetoxymethyl ester, pivaloyloxymethyl ester, ethoxycarbonyloxy ester, choline ester, dimethylaminoethyl ester, 5-indanyl ester, phthalidinyl ester, 5-substituted-2-oxo-1,3-dioxo-4-ylmethyl ester and various oxoalkyl ester such as 3-acetoxy-2-oxobutyl ester are suitable.

The compounds of the present ivnention have excellent antibacterial activity and thus can be used as human and veterinary medicines, fish medicines, agricultural chemicals and food preservatives.

The dose of the compound of the present invention as the active ingredient of medicine for human use is in the range of 50 mg to 1 g per adult per day, and preferably of 100 to 300 mg per adult per day. The dose for medicine for use with animals is in the range of from 1 to 200 mg per kg of body weight per day, and preferably of 5 to 100 mg per kg of body weight per day. The daily dose should be adjusted in accordance with such factors as intended use (such as therapeutic or preventive), kind, size or age of the human or the animal to be cured, the kind of pathogenic organisms, to be treated and symptoms exhibited, etc.

The daily dose described above may be divided into 1 to 4 times per day. It may be necessary to deviate from the amount described hereinbefore according to causative organisms or the severity of the symptoms exhibited.

The compounds according to the present invention are active against a very broad spectrum of microorganisms and it is possible to prevent, alleviate and/or cure the diseases caused by such pathogens. Examples of susceptible bacteria or bacteria-like microorganisms include Staphylococcus sp., *Streptococcus pyogenes*, hemolytic streptococci, entero-cocci, *Streptococcus pneumoniae*, *Neisseria gonorrhoeae*, *Escherichia coli*, Citrobacter sp., Shigella sp., Klebsiella pneumoniae, Enterobacter sp., Serratia sp., Proteus sp., *Pseudomonas aeruginosa*, *Haemophilus influenzae*, Acinetobacter sp., Campylobacter sp. and Chlamidiae.

Examples of diseases which can be prevented, alleviated and/or cured by the compound of compounds according to the present invention include pneumonia, chronic bronchitis, diffuse panbronchiolitis, bronchiectasis with infection, secondary infections of chronic respiratory diseases, pharyngolaryngitis, tonsillitis, acute bronchitis, pyelonephritis, cytisis, prostatitis, epididymitis, gonococcal urethritis, non-gonococcal urethritis, folliculitis, furuncle, furunculosis, carbuncle, erysipelas, phlegmon, lymphangitis/lymphadenitis, felon, subcutaneous abscess, spiradenitis, acne conglobata, infectious atheroma, perianal abscess, mastadenitis, superficial secondary infections after trauma, burn or surgery trauma, cholecystitis, cholangitis, otitis media, sinusitis, blepharitis, hordeolum, dacryocystitis, tarsadenitis, keratohelcosis, bacillary dysentery and enteritis.

Examples of susceptible microorganism which cause veterinary diseases include Escherichia sp., Salmonella sp., Pasteurella sp., Haemophysalis sp., Bordetella sp., Staphylococcus sp., and Mycoplasma sp. The following are some examples of veterinary diseases; those of fowl include colibacillosis, pullorum disease, avian paratyphosis, fowl cholera, infectious coryza, Staphylococcal infections, and mycoplasmal diseases; those of pigs include colibacillosis, salmonellosis, pasteurellosis, haemophylus infection, atrophic rhintis, exudative epidermitis, and mycoplasmal diseases; those of cattle include colibacillosis, salmonellosis, hemorrhagic septicemia, mycoplasmal diseases, bovine contageous pleurponeumonia, and bovine mastesis; those of dogs include coliform sepsis, salmonelosis, hemorrhagic septicemia, pyometra, and cystitis; and those of cats include hemorrhagic pleuritis, cystitis, chronic rhiniti; and those of kittens include bacterial entritis and mycoplasmal diseases.

The pharmaceutical preparations containing one or more compounds of the present invention as the active ingredients can be prepared according to the conventional preparation methods. Examples of the pharmaceutical preparations for oral administration include tablets, powders, granules, capsules, solutions, syrups, elixirs and oily or aqueous suspensions.

The solid preparations may contain the active compound or compounds of the present invention alongside the customary excipients such as fillers, extenders, binders, humectants, absorption accelerators, wetting agents, adsorbents, and lubricants. The liquid preparations may include solutions, suspensions or emulsions. These may contain in addition to the active compound or compounds, the customary excipients such as solubilizing agents, emulsifiers, stabilizers or preservatives in its preparation. The solutions of the compound(s) of the present invention which may contain these ingredients is put into a container such as ampoules or vial vessels and, further, this solution may be solidified by means of lyophilization. The lyophilized formulation is dissolved by diluent at administration. The container may contain either single dose or multiple doses.

Examples of topical preparations include solutions, suspensions, emulsions, ointments, gels, creams, lotions and sprays.

The compound of the present invention may also be administered to animals as oral or non-oral veterinary medicines. And such medicines may be administered in the form of a mixture with feedstuff or water. The preparations for veterinary medicine or additives can be prepared according to the customary method of the field and such preparations include powders, fine granules, granules, solubilized powders, syrups, solutions and injections.

The following are the examples of the formulations and these are purely illustrative and in no way to be interpreted as restrictive.

| Formulation Example 1 | |
|---|---|
| Each capsule contains: | |
| Compound 32b | 100.0 mg |
| Corn starch | 23.0 mg |
| Calcium carboxymethyl cellulose | 22.5 mg |
| Hydroxypropylmethyl cellulose | 3.0 mg |
| Magnesium stearate | 1.5 mg |
| | 150.0 mg |
| Formulation Example 2 | |
| A solution contains: | |
| Compound 31b | 1 to 10 g |
| Acetic acid or sodium hydroxide | 0.5 to 1 g |
| Ethyl p-hydroxybenzoate | 0.1 g |
| Purified water | 88.9 to 98.4 g |
| | 100.0 g |
| Formulation Example 3 | |
| A powder for admixing with feedstuff contains: | |
| Compound 55b | 1 to 10 g |
| Corn starch | 98.5 to 89.5 g |
| Light anhydrous silicic acid | 0.5 g |
| | 100.0 g |

Although the disclosure illustrates and describes a preferred embodiment of this invention, it is to be understood that it is not restricted thereto.

The following examples are further illustrative of the present invention but should by no means be construed as limiting its scope.

The antibacterial activity assays were performed by the method specified by Japan Society of Chemotherapy (Chemotherapy 29(1), 76 (1981). The table of antibacterial activity is followed by the reaction schemes for the synthesis of various spiro ring-containing cyclic amine derivatives, intermediate compounds for synthesis of quinolone rings and synthesis of various spiro compounds.

REFERENCE EXAMPLE 1

Synthesis of 7-amino-5-azaspiro[2,4]heptane

1) Ethyl 1-acetyl-1-cyclopropanecarboxylate (compound 2)

To 10.4 g of ethyl acetoacetate were added 15 g of 1,2-dibromoethane, 23 g of potassium carbonate and 150 ml of N,N-dimethylformamide (DMF) and the mixture was stirred at room temperature for 2 days. After the insolubles were filtered off, the filtrate was concentrated to dryness under reduced pressure and to the residue was added water. The mixture was extracted with chloroform. The extract was dried over anhydrous sodium sulfate and the solvent was removed under reduced pressure. The light yellow oily residue was then subjected to vacuum distillation to yield 7.5 g of title compound 2 as a fraction boiling at 70°–71° C./2–3 mmHg.

$^1$H-NMR (CDCl$_3$) δppm: 1.30 (3H, t, J=7 Hz), 1.48 (4H, s), 2.49 (3H, s), 4.24 (2H, q, J=7 Hz).

2) 5-Benzyl-4,7-dioxo-5-azaspiro[2,4]heptane (compound 4)

In 50 ml of ethanol was dissolved 7 g of compound 2 and, then, 8.0 g of bromine was added dropwise thereto with stirring at room temperature. After 2 hours of stirring at this temperature, the excess bromine and the solvent were removed under reduced pressure to give ethyl 1-bromoacetyl-1-cyclopropanecarboxylate (compound 3). This product was dissolved as it was, i.e., without purification, in 50 ml of ethanol and 12 g of benzylamine was added dropwise thereto with stirring and ice-cooling. The mixture was then stirred at room temperature for 24 hours, after which the solvent was removed under reduced pressure. The residue was dissolved in 200 ml of chloroform and the solution was washed with 1N hydrochloric acid and saturated aqueous sodium chloride in that order and dried over anhydrous sodium sulfate. The solvent was then removed and the residue was subjected to silica gel chromatography using 2% methanol-chloroform as an eluent. The procedure gave 2.3 g of title compound 4 as light yellow crystals.

$^1$H-NMR (CDCl$_3$) δppm: 1.6–1.8 (4H, m), 3.78 (2H, s), 4.68 (2H, s), 7.2–7.45 (5H, br s).

3) 5-Benzyl-7-(hydroxyimino)-4-oxo-5-azaspiro[2,4]heptane (compound 5)

To 670 mg of compound 4 were added 700 mg of hydroxylamine hydrochloride, 200 mg of triethylamine and 10 ml of ethanol. The mixture was stirred at room temperature overnight. The solvent was then removed under reduced pressure and the residue was dissolved in 10% aqueous citric acid and extracted with chloroform. The chloroform layer was extracted with 1N aqueous sodium hydroxide and the aqueous layer was acidified with concentrated hydrochloric acid and extracted with chloroform. This extract was dried over anhydrous sodium sulfate and the solvent was then distilled off under reduced pressure to yield 490 mg of title compound 5 as colorless crystals.

$^1$H-NMR (CDCl$_3$) δppm: 1.3–1.7 (4H, m), 3.80* & 4.10* (2H, s), 4.60 & 4.70 (2H, s), 7.38 (5H, arm.) (*, **: a mixture of syn- and anti-isomers)

4) 7-Amino-5-azaspiro[2,4]heptane (compound 7)

In 80 ml of dry tetrahydrofuran was dissolved 490 mg of compound 5 followed by addition of 500 mg of lithium aluminum hydride and the mixture was refluxed for 8 hours. Then, at room temperature, 0.5 ml of water, 0.5 ml of 15% aqueous sodium hydroxide and 1.5 ml of water were added thereto in the order mentioned and the insolubles were filtered off. The filtrate was concentrated under reduced pressure to give 7-amino-5-benzyl-5-azaspiro[2,4]heptane (compound 6). This product was dissolved as it was, i.e., without purification, in 20 ml of ethanol and after addition of 10% palladium-on-carbon, catalytic hydrogenation was carried out at 4.5 kg/cm$^2$ and 50° C. After 6 hours of reaction, the catalyst was filtered off and the filtrate was concentrated under reduced pressure at a temperature not higher than room temperature. The above procedure gave title compound 7 as a crude product. This compound 7 was used, without purification, in various reactions.

(5) 7-[(R)-N-p-toluenesulfonylpropyl]amino-5-benzyl-5-azaspiro[2,4]heptane (compound 8)

A mixture of 2.8 g of compound 6, 1.5 g of triethylamine and 50 ml of methylene chloride was prepared, and a solution of (R)-N-p-toluenesulfonylpropyl chloride (prepared from 4 g of (R)-N-p-toluenesulfonylproline and an excess amount of thionyl chloride) in 10 ml of methylene chloride was added dropwise to the above mixture over a period of 10 minutes with ice-cooling and stirring. The mixture was then stirred at room temperature for 3 hours. The reaction mixture was washed with saturated aqueous sodium hydrogencarbonate and saturated aqueous sodium chloride and dried over anhydrous sodium sulfate. The solvent was removed under reduced pressure and the residue was subjected to flash column chromatography (silica gel 80 g). From the ethyl acetate fraction, 3.5 g of title compound 8 was obtained as a syrup.

6)
7-[(R)-N-p-toluenesulfonylpropyl]amino-5-benzyloxycarbonyl-5-azaspiro[2,4]heptane (compound 9) and optical isomers (compound 9a and compound 9b)

To 4 ml of dry methylene chloride were added 3.5 g of compound 8 and 2.5 ml of benzyl chlorocarbonate and the mixture was stirred at room temperature for 12 hours. After 4 ml of benzyl chlorocarbonate was further added, the mixture was stirred for 5 hours. Then, chloroform was added to the reaction mixture. The mixture was washed with saturated aqueous sodium hydrogencarbonate and saturated aqueous sodium chloride in the order mentioned and dried over anhydrous sodium sulfate. The solvent was then removed under reduced pressure and the residue was subjected to flash column chromatography (silica gel 85 g). From the ethyl acetate-n-hexane (2:1–4:1, v/v) fraction, 3 g of the title compound 9 was obtained as a light yellow oil. This oil was immediately subjected to HPLC to give 1.40 g of compound 9a and 1.45 g of compound 9b.

Column: Nucleosil® 50-5 (20×250 mm)
Eluent: Ethyl acetate
Flow rate: 11 ml/min
Retention time: 9a: 19.5 min, 9b: 21 min
9a: $[\alpha]_D$ +133 6° (c=0.75, chloroform)
9b: $[\alpha]_D$ +76.0° (c=0.85, chloroform)

7) Optically active 7-amino-5-azaspiro[2,4]heptane (compound 7a and compound 7b)

1.4 g of compound 9a was dissolved in 20 ml of ethanol followed by the addition of 15 ml of 2N aqueous sodium hydroxide solution. The mixture was refluxed for 19 hours. The reaction mixture was then acidified with concentrated hydrochloric acid and washed with chloroform twice and ethyl acetate once. The aqueous layer was then concentrated under reduced pressure to give a colorless solid residue. To this colorless solid was added 10 ml of 50% aqueous sodium hydroxide and the mixture was distilled under reduced pressure to give an aqueous solution containing compound 7a. This distillate was used, as it was, in the next reaction.

The other compound 7b was also obtained from compound 9b in the like manner.

8) 7-tert-Butoxycarbonylamino-5-azaspiro[2,4]heptane (compound 11)

In 30 ml of tetrahydrofuran was dissolved 800 mg of compound 6 followed by the addition of 1.2 g of 2-(tert-butoxycarbonyloxyimino)-2-phenylacetonitrile (BOC-ON) at room temperature and the mixture was stirred at that temperature for 2 hours. The solvent was then removed under reduced pressure and to the residue was added chloroform. The mixture was extracted with a 10% aqueous citric acid. The citric acid extract was adjusted to pH≧10 with 1N aqueous sodium hydroxide and extracted with chloroform. The extract was dried over anhydrous sodium sulfate and the solvent was removed under reduced pressure to give 900 mg of 7-tert-butoxycarbonylamino-5-benzyl-5-azaspiro[2,4-]heptane (compound 10). 870 mg of this compound 10 was dissolved in 15 ml of ethanol and catalytic hydrogenation was carried out at 40° C. and 4.5 kg/cm² in the presence of 500 mg of 10% palladium-on-carbon for 2 hours. The catalyst was then filtered off and the filtrate was concentrated under reduced pressure to give title compound 11. This product was used without purification in the substitution reaction.

REFERENCE EXAMPLE 2

Synthesis of optically active 7-amino-5-azaspiro[2,4]heptane 1)
5-[(1R)-Phenylethyl]-4,7-dioxo-5-azaspiro[2,4]heptane (compound 12)

35.7 g of compound 2 was dissolved in 200 ml of ethanol and then 40 g of bromine was added dropwise with stirring at room temperature. The reaction mixture was stirred at room temperature for 2 hours, after which the excess bromine and the solvent were removed under reduced pressure to give ethyl 1-bromoacetyl-1-cyclopropanecarboxylate (compound 3). This product was dissolved, without purification, in 200 ml of ethanol and under ice-cooling and stirring, 33 g of R-(+)-1-phenylethylamine and 27 g of triethylamine were simultaneously added dropwise over a period of 1 hour. Then, at room temperature, the mixture was stirred for 2 days. Thereafter, the insolubles were filtered off and the ethanol was removed under reduced pressure. The residue was dissolved in 300 ml of ethyl acetate and the solution was washed successively with 1N hydrochloric acid, saturated aqueous sodium hydrogencarbonate and saturated aqueous sodium chloride. The organic layer was dried over anhydrous sodium sulfate. The solvent was then removed under reduced pressure and the residue was subjected to silica gel (200 g) column chromatography using chloroform-2% methanol/chloroform as an eluent system. The procedure gave title compound 12 as colorless crystals.

m.p.: 98°–103° C.
¹H-NMR (CDCl₃) δppm: 1.4–1.8 (4H, m), 1.62 (3H, d, J=7.2 Hz), 3.5 (1H, d, J=18 Hz), 3.9 (1H, d, J=18 Hz), 5.82 (1H, q, J=7.2 Hz), 7.36 (5H, s).

2)
5-[(1R)-Phenylethyl]-7-hydroxyimino-4-oxo-5-azaspiro[2,4]heptane (compound 13)

To 3.35 g of compound 12 were added 1.6 g of hydroxylamine hydrochloride, 2.3 g of triethylamine and 80 ml of ethanol and the mixture was stirred at room temperature for 2 hours. The solvent was then removed under reduced pressure and the residue was extracted with chloroform. The extract was washed with 10% aqueous citric acid and saturated aqueous sodium chloride. The organic layer was dried over anhydrous sodium sulfate and the solvent was removed under reduced pressure. The procedure gave 3.5 g of title compound 13 as colorless crystals.

m.p.: 188°–194° C.
¹H-NMR (CDCl₃) δppm: 1.2–1.4 (2H, m), 1.53 (3H, d, J=7.2 Hz, & 2H, m), 3.8 (1H, d, J=18 Hz), 4.16 (1H, d, J=18 Hz), 5.63 (1H, q, J=7.2 Hz), 7.32 (5H, s).

3)
7-Amino-4-oxo-5-[(1R)-phenylethyl]-5-azaspiro[2,4-]heptane (compound 14a and compound 14b)

To 150 ml of methanol were added 3.5 g of compound 13 and 7.5 ml of Raney nickel. Catalytic reduction was carried out at room temperature for 12 hours. After the catalyst was filtered off, the solvent was removed under reduced pressure and the residue was subjected to silica gel (100 g) column chromatography using 5% methanol/chloroform as an eluent. The procedure gave 1.0 g of compound 14b (obtained from the fraction eluted earlier) and 0.8 g of compound 14a as colorless oils.

14b: $^1$H-NMR (CDCl$_3$) δppm: 0.8–1.4 (4H, m), 1.52 (3H, d, J=7 Hz), 2.87 (1H, dd, J=10, 3 Hz), 3.3–3.9 (2H, m), 4.27 (2H, br s), 5.42 (1H, q, J=7 Hz), 7.29 (5H, s).

14a:) $^1$H-NMR (CDCl$_3$) δppm: 0.6–1.3 (4H, m), 1.40 (2H, s), 1.53 (3H, d, J=7.2 Hz), 2.99 (1H, dd, J=12.8, 7.2 Hz), 3.15–3.45 (2H, m), 5.52 (1H, q, J=7.2 Hz), 7.30 (5H, s).

4) 7-Amino-5-[(1R)-phenylethyl]-5-azaspiro[2,4]heptane (compound 15a and compound 15b)

To 50 ml of dry tetrahydrofuran were added 1.0 g of compound 14b and 500 mg of lithium aluminum hydride and the mixture was refluxed for 17 hours. After cooling, to the reaction mixture was successively added 0.5 ml of water, 0.5 ml of 15% aqueous sodium hydroxide and 1.5 ml of water and the mixture was further stirred at room temperature for 30 minutes. The insoluble material was then removed by filtration and was washed with tetrahydrofuran. The washings and the filtrate were combined and dried. Finally, the solvent was removed under reduced pressure to yield 940 mg of title compound 15b as a light yellow oil. Similarly, 755 mg of compound 15a was prepared from 800 mg of compound 14a.

15b: $^1$H-NMR (CDCl$_3$) δppm: 0.2–0.8 (4H, m), 1.35 (3H, d, J=6.6 Hz), 1.6–2.0 (2H, br m), 2.2–3.1 (4H, m), 3.24 (1H, q, J=6.6 Hz), 3.5–3.9 (1H, m), 7.28 (5H, br s).

15a: $^1$H-NMR (CDCl$_3$) δppm: 0.3–0.9 (4H, m), 1.36 (3H, d, J=6.7 Hz), 1.8–2.2 (2H, m), 2.2–3.2 (4H, m), 3.24 (1H, q, J=6.7 Hz), 3.6–3.9 (1H, m), 7.28 (5H, br s).

5) 7-(tert-Butoxycarbonylamino)-5-[(1R)-phenylethyl]-5-azaspiro[2,4]heptane (compound 16a and compound 16b)

To 20 ml of dry tetrahydrofuran were added 764 mg of compound 15b and 1.3 g of BOC-ON. The mixture was stirred at room temperature for 4 hours. The reaction mixture was diluted with ethyl acetate, washed with 1N aqueous sodium hydroxide twice and water once and extracted with 10% aqueous citric acid. After the aqueous layer was washed with ethyl acetate once, it was made alkaline with 15% aqueous sodium hydroxide under cooling and then extracted with 3 portions of chloroform. The organic layers were combined, washed with saturated aqueous sodium chloride and dried and the solvent was removed. The residue was subjected to silica gel (20 g) column chromatography, with an eluent of chloroform-methanol (20:1, 10:1). The procedure gave 690 mg of title compound 16b. Upon standing, this product crystallized. The crystals were washed with n-hexane. The title compound 16a was also prepared in a like manner.

16b: colorless crystals
m.p.: 103°–105° C.
[α]$_D$ −15.2° (c=1.475, chloroform).
$^1$H-NMR (CDCl$_3$) δppm: 0.4–0.9 (4H, m), 1.36 (3H, d, J=7.2 Hz), 1.44 (9H, s), 2.42 (2H, AB q, J=10.2 Hz), 2.79 (2H, d, J=5.6Hz), 3.24 (1H, q, J=7.2 Hz), 3.6–4.0 (1H, m), 4.6–5.1 (1H, br d), 7.28 (5H, s).

Elemental analysis, for C$_{19}$H$_{28}$N$_2$O$_2$ Calcd.: C; 72.12, H; 8.92, N; 8.85, Found: C; 71.63, H; 9.07, N; 8.64.

16a: colorless crystals
m.p 94°–97° C.
[α]$_D$ +47.6° (c=0.89, chloroform)
$^1$H-NMR (CDCl$_3$) δppm: 0.4–0.9 (4H, m), 1.33 (3H, d, J=6.6 Hz), 1.40 (9H, s), 2.29 (1H, d, J=9 Hz), 2.44 (1H, dd, J=10.8, 3.6 Hz), 2.77 (1H, d, J=9 Hz), 2.88 (1H, dd, J=10.8, 5.3 Hz), 3.22 (1H, q, J=6.6 Hz), 3.6–3.9 (1H, m), 4.7–5.2 (1H, br d), 7.27 (5H, s).

Elemental analysis, for C$_{19}$H$_{28}$N$_2$O$_2$ Calcd.: C; 72.12, H; 8.92, N; 8.85. Found: C; 71.86, H; 9.36, N; 8.68.

6) 7-tert-Butoxycarbonylamino-5-azaspiro[2,4]heptane (compound 11a and compound 11b, optical isomer of compound 11)

To 30 ml of ethanol were added 650 mg of compound 16b and 500 mg of palladium-on-carbon (50% water wet) and catalytic reduction was carried out at a presence of 4.2 atm and the reaction vessel was warmed by a tungsten lamp. The reduction reaction was carried out for 6 hours. The catalyst was then filtered off and the mother liquor was condensed to dryness under reduced pressure. The resulting oily residue was diluted with ethyl acetate and extracted with 10% aqueous citric acid twice. The aqueous layer was made alkaline with 15% aqueous sodium hydroxide and extracted with 3 portions of chloroform. The chloroform layers were pooled, washed with water and dried and the solvent was removed to give 440 mg of title compound 11b as a crude product. The title compound 11a was also prepared in a like manner. The $^1$H-NMR spectra of compounds 11b and 11a were in complete agreement.

17b: $^1$H-NMR (CDCl$_3$) δppm: 0.4–1.0 (4H, m), 1.42 (9H, s), 2.71 (1H, d, J=10.2 Hz), 2.92 (1H, dd, J=10.8, 3.6 Hz), 3.01 (1H, d, J=10.2 Hz), 3.33 (1H, dd, J=10.8, 5.4 Hz), 3.5–3.9 (1H, m), 5.0–5.4 (1H, br d).

REFERENCE EXAMPLE 3

Synthesis of 4,7-diazaspiro[2,5]octane 1)
Cyclopropane-1,1-dibromoamide (compound 18)

14.0 g of cyclopropane-1,1-diamide 17 was suspended in 35 g of bromine and under stirring at room temperature, 130 ml of an aqueous potassium hydroxide prepared using 14 g of potassium hydroxide was added dropwise. After 1 hour of stirring, the reaction mixture was cooled with ice and the resulting crystals were collected by filtration, washed with ice water and dried in the air. The crystals were then dried under reduced pressure at 66° C. for 2 hours to give 28.6 g of title compound 18.

2) 4,6-Diazaspiro[2,4]heptane-5,7-dione (compound 19)

To a sodium methoxide solution prepared from 9.1 g of sodium metal and dry methanol was added 26 g of compound 18 with ice-cooling and stirring. After removal of the ice bath, the mixture was further stirred whereupon the internal temperature rose from about 5° C. by degrees and then after about 20° C., sharply rose to the boiling point of methanol. The reaction mixture was maintained under reflux for 10 minutes and then cooled to room temperature. The reaction mixture was then concentrated to dryness under reduced pressure and acetone was added to the residue. The crystals were collected by filtration and washed with acetone. The washings and the filtrate were combined and concentrated under reduced pressure. The procedure gave title compound 19 as a crude product. This product was used without purification in the next reaction.

3) 1-Aminocyclopropanecarboxylic acid 20 and 1-tert-butoxycarbonylaminocyclopropanecarboxylic acid (compound 21)

The above crude compound 19 was dissolved in 60 ml of water followed by the addition of 15 g of barium hydroxide. The mixture was heated in a stainless steel autoclave at an external temperature of 170° C. for 2 hours. The reaction mixture was then allowed to stand overnight and the separated barium carbonate was filtered off. Then, ammonium carbonate was added to the filtrate and the precipitated barium carbonate was filtered off. The filtrate was concentrated to give the title amino compound 20 as a crude product. This compound 20 was subjected, without purification, to tert-butoxycarbonylation with BOC-ON to give 2.5 g of title compound 21.

$^1$H-NMR (CDCl$_3$) δppm: 1.85 (2H, t), 2.05 (9H, s), 2.15 (2H, t).

4) Ethyl (1-tert-butoxycarbonylamino-1-cyclopropylcarbonylamino)acetate (compound 22)

700 mg of compound 21 was dissolved in 50 ml of dioxane followed by the addition of 800 mg of dicyclohexylcarbodiimide and 600 mg of glycine ethyl ester hydrochloride. Then, with stirring at room temperature, 10 ml of a dioxane solution of 400 mg of triethylamine was gradually added dropwise and the mixture was further stirred for 3 hours. The solvent was then removed under reduced pressure and the residue was subjected to silica gel column chromatography using 5% methanol-chloroform as an eluent. The procedure gave 700 mg of title compound 22.

5) Ethyl (1-amino-1-cyclopropylcarbonylamino)acetate (compound 23)

To 680 mg of compound 22 were added 10 ml of trifluoroacetic acid and 0.5 g of anisole. The mixture was stirred at room temperature for 2 hours. The solvent was removed under reduced pressure. To the residue was added aqueous potassium carbonate and pH was adjusted over 10. The mixture was saturated with sodium chloride and extracted with chloroform. The chloroform layer was dried over anhydrous sodium sulfate and the solvent was removed under reduced pressure. The procedure gave 410 mg of compound 23.

$^1$H-NMR (CDCl$_3$) δppm: 0.85 (2H, t), 1.28 (3H, t), 1.46 (2H, t, J=4 Hz), 1.68 (2H, br s), 4.21 (2H, t, J=7 Hz), 4.40 (2H, d, J=7 Hz).

6) 4,7-Diazaspiro[2,5]octane-5,8-dione (compound 24)

When 500 mg of compound 23 was heated on an oil bath at 220° C., it foamed and then was solidified. The heating was continued for 20 minutes, at the end of which time the reaction system was cooled to room temperature. The procedure gave title compound 24 as a crude product.

$^1$H-NMR (DMSO-d$_6$) δppm: 0.96 (2H, t), 1.17 (2H, t, J=4 Hz), 3.86 (2H, J=3 Hz), 8.0, 8.25 (each 1H, br s).

7) 4,7-Diazaspiro2,5]octane (compound 25)

350 mg of compound 24 was suspended in 200 ml of dry tetrahydrofuran followed by the addition of 0.6 g of lithium aluminum hydride. The mixture was refluxed for 14 hours. To this reaction mixture was then added 0.6 g of water, 0.6 g of 15% aqueous sodium hydroxide and 1.8 g of water in the order mentioned under ice-cooling and the resulting precipitate was removed by filtration. The precipitate was thoroughly washed with tetrahydrofuran and ether and the washings and the filtrate were combined. The solvent was then removed under reduced pressure to give title compound 4,7-diazaspiro[2,5]octane 25 as a crude product. This product was subjected, without purification, to the substitution reaction.

REFERENCE EXAMPLE 4

Synthesis of benzoic acid derivatives 1) 3-Chloro-2,4,5-trifluorobenzoic acid (compound 27)

9.3 g of anhydrous cuprous chloride and 8.8 g of tert-butyl nitrite were added to 150 ml of acetonitrile and under stirring and heating at 60° C., 11 g of 3-amino-2,4,5-trifluorobenzoic acid 26 (a commercial product) was added. The mixture was stirred for 20 minutes. After cooling, 500 ml of 15% hydrochloric acid was added and the mixture was extracted with ethyl acetate. The extract was dried over anhydrous sodium sulfate and the solvent was then removed under reduced pressure. Finally the residue was subjected to silica gel (100 g) column chromatography using chloroform as an eluent. The procedure gave 8.4 g of 3-chloro-2,4,5-trifluorobenzoic acid 27 as colorless needles.

m.p.: 114°–115° C.

Elemental analysis, for C$_7$H$_2$ClF$_3$O$_2$: Calcd.: C; 39.93, H; 0.96. Found: C; 39.87, H; 1.04.

$^1$H-NMR (CDCl$_3$) δppm: 7.76 (1H, ddd, J=6.5, 8.5, 9.9 Hz), 8.6–9 2 (1H, br s).

2) 2,4,5-Trifluoro-3-iodobenzoic acid (compound 28)

10 g of cuprous iodide and 8.8 g of tert-butyl nitrite were added to 150 ml of acetonitrile and under stirring at 60° C., 11 g of 3-amino-2,4,5-trifluorobenzoic acid was added. The stirring was continued for 20 minutes and after cooling, 500 ml of 15% hydrochloric acid was added. The mixture was then extracted with ethyl acetate. The organic layer was dried over anhydrous sodium sulfate and the solvent was removed under reduced pressure. The residue was chromatographed on 100 g of silica gel eluting with chloroform. The fractions containing the object compound were collected and the solvent was removed under reduced pressure. Finally, the residue was recrystallized from n-hexane to give 8.4 g of title compound 28 as colorless crystals.

m.p.: 121°–122° C.

Elemental analysis, for C$_7$H$_2$F$_3$IO$_2$.$\frac{1}{4}$H$_2$O: Calcd.: C 28.26, H 0.51. Found: C 28.19, H 0.76.

MS m/z: 302 (M+).

Using anhydrous cuprous bromide in otherwise the same manner as above, 3-bromo-2,4,5-trifluorobenzoic acid (compound 29) was synthesized.

m.p.: 124°–125° C.

3) 2,4,5-Trifluorobenzoic acid (compound 30)

3-1 Direct deamination 1.8 g of tert-butyl nitrite was dissolved in 5 ml of dry dimethylformamide and under stirring at 60° C., 2.0 g of 3-amino-2,4,5-trifluorobenzoic acid was added thereto. The mixture was further stirred for 20 minutes. The reaction mixture was then poured into 50 ml of water and extracted with diethyl ether. The organic layer was dried over anhydrous sodium sulfate and concentrated to dryness under reduced pressure. The residue was subjected to silica gel column chromatography using chloroform as an eluent. The procedure gave 1.1 g crystals of title compound 30.

3-2 Reduction of the bromo-compound

A mixture consisting of 5.0 g of 3-bromo-2,4,5-trifluorobenzoic acid 29, 30 ml of acetic acid, 2.0 g of sodium acetate and 1.0 g of 5% palladium-on-carbon was subjected to a reduction reaction in a hydrogen atmosphere for 4 hours. The catalyst was then filtered off and the filtrate was concentrated to dryness under reduced pressure. The residue was extracted with ethyl acetate and the extract was washed with water and dried over anhydrous sodium sulfate. Finally, the solvent was removed under reduced pressure to give 3.2 g of title compound 30 as colorless crystals.

$^1$H-NMR (CDCl$_3$) δppm:

30: $^1$H-NMR (CDCl$_3$) δppm: 7.10 (1H, ddd, J=6.5, 9, 9Hz), 7.96 (1H, ddd, J=6.3, 8.5, 9.8 Hz), 9.2–9.6 (1H, br s).

EXAMPLE 1

7-(7-Amino-5-azaspiro[2,4]heptan-5-yl)-1-cyclopropyl-6,8-difluoro-1,4-dihydro-4-oxoquinoline-3-carboxylic acid (compound 31)

300 mg of 7-amino-5-azaspiro[2,4]heptane 7 and 250 mg of 1-cyclopropyl-6,7,8-trifluoro-1,4-dihydro-4-oxoquinoline-3-carboxylic acid were added to 5 ml of dimethyl sulfoxide. The mixture was heated at 100° C. for 30 minutes. After cooling, the solvent was distilled off under reduced pressure and the residue was crystallized by addition of ethanol. The resulting crude crystals were collected by filtration, suspended in ethanol and dissolved by the addition of 28% aqueous ammonia. To this solution was added 50 mg of activated carbon and the mixture was filtered. The filtrate was concentrated by heating and the resulting crystals were collected by filtration. The procedure gave 170 mg of title compound 31.

m.p.: 238°–245° C.

Elemental analysis, for C$_{19}$H$_{19}$F$_2$O$_3$.½H$_2$O: Calcd.: C; 59.37, H; 5.24, N; 10.93. Found: C; 59.63, H; 5.71, N; 10.85.

EXAMPLE 2

Synthesis of optical isomer (compound 31a and compound 31b) of compound 31

140 mg of 1-cyclopropyl-6,7,8-trifluoro-1,4-dihydro-4-oxoquinoline-3-carboxylic acid was suspended in 2 ml of dimethyl sulfoxide followed by the addition of 66 mg of triethylamine and, further, an excess amount of an aqueous solution of optically active amino-compound 7a. The mixture was heated at 120° C. for 3 hours. The solvent was then removed under reduced pressure and the residue was purified by preparative TLC (developed with the bottom layer of chloroform-methanol-water=7:3:1). The resulting crystals were recrystallized from ethanol-28% aqueous ammonia to give 40.5 mg of compound 31a as light yellow microcrystals.

Using compound 7b in otherwise the same manner, 34 mg of compound 31b was also obtained. (+)-7-(7-Amino-5-azaspiro[2,4]heptan-5-yl)-1-cyclopropyl-6,8-difluoro-1,4-dihydro-4-oxoquinoline-3-carboxylic acid 31a m.p.: 221°–235° C. (decomp.).

$[α]_D$ +116.2° (c=0.575, concentrated aqueous ammonia).

Elemental analysis, for C$_{19}$H$_{19}$F$_2$O$_3$.½H$_2$O. Calcd.: C; 59.37, H; 5.24, N; 10.93. Found: C; 59.31, H; 5.02, N; 10.93.

(−)-7-(7-Amino-5-azaspiro[2,4]heptan-5-yl)-1-cyclopropyl-6,8-difluoro-1,4-dihydro-4-oxoquinoline-3-carboxylic acid 31b m.p. 227°–240° C. (decomp.).

$[α]_D$ −106 3° (c=0.365, concentrated aqueous ammonia)

Elemental analysis, for C$_{19}$H$_{19}$F$_2$N$_3$O$_3$.½H$_2$O: Calcd.: C; 59.37, H; 5.24, N; 10.93. Found: C; 59.33, H; 4.90, N; 10.65.

EXAMPLE 3

7-(7-Amino-5-azaspiro[2,4]heptan-5-yl)-8-chloro-1-cyclopropyl-6-fluoro-1,4-dihydro-4-oxoquinoline-3-carboxylic acid (compound 32)

200 mg of 8-chloro-1-cyclopropyl-6,7-difluoro-1,4-dihydro-4-oxoquinoline-3-carboxylic acid, 150 mg of compound 11 and 70 mg of triethylamine were added to 5 ml of acetonitrile and the mixture was refluxed for 24 hours. After cooling, the solvent was removed under reduced pressure and to the residue was added water. The precipitate was collected by filtration and washed successively with water, acetonitrile, ethanol and ether and dried. The procedure gave 245 mg of 7-(7-tert-butoxycarbonylamino-5-azaspiro[2,4]heptan-5-yl)-8-chloro-1-cyclopropyl-6-fluoro-1,4-dihydro-4-oxoquinoline-3-carboxylic acid melting at 205°–207° C.

To 200 mg of this carboxylic acid were added 0.3 ml of anisole and 5 ml of trifluoroacetic acid. The mixture was stirred at room temperature for 30 minutes. The solvent was removed under reduced pressure and to the residue was added water. The mixture was made alkaline with 1N aqueous sodium hydroxide. The mixture was washed with chloroform twice, neutralized (pH 7.1) with 10% aqueous citric acid. The mixture was extracted with 3 portions of chloroform. The extract was washed with water and dried over anhydrous sodium sulfate. The solvent was then removed under reduced pressure and the residue was recrystallized from ethanol-concentrated aqueous ammonia. The procedure gave 105 mg of title compound 32.

m.p.: 235°–240° C. (decomp.).

Elemental analysis, for C$_{19}$H$_{19}$ClFN$_3$O$_3$.½H$_2$O: Calcd.: C 57.58, H 4.96, N 10.60. Found: C 57.64, H 5.33, N 10.37.

EXAMPLE 4

7-(7-Amino-5-azaspiro[2,4]heptan-5-yl)-1-cyclopropyl-6-fluoro-1,4-dihydro-4-oxoquinoline-3-carboxylic acid (compound 33)

250 mg of 1-cyclopropyl-6,7-difluoro-2,3-dihydro-4-oxoquinoline-3-carboxylic acid and 250 mg of compound 11 were added to 4 ml of dimethyl sulfoxide and the mixture was heated at 120° C. for 2 hours. After cooling, the solvent was removed under reduced pressure and the residue was crystallized by the addition of ethanol. The crystals were collected by filtration. The procedure gave 7-(7-tert-butoxycarbonylamino-5-azaspiro[2,4]heptan-5-yl)-1-cyclopropyl-6-fluoro-1,4-dihydro-4-oxoquinoline-3-carboxylic acid as a crude product.

5 ml of trifluoroacetic acid wa added to this product and the mixture was stirred at room temperature for 30 minutes to remove the tert-butoxycarbonyl group. The solvent was then removed under reduced pressure and the residue was dissolved in 1N aqueous sodium hydroxide. The solution was washed with chloroform and adjusted to pH 7.0 with 1N hydrochloric acid, whereupon crystals separated out. The crystals were collected by filtration and recrystallized from ethanol-concentrated aqueous ammonia to give 200 mg of title compound 33.

m.p 249°–252° C.

Elemental analysis: $C_{19}H_{20}FN_3O_3$. Calcd.: C; 63.85, H; 5.64, N; 11.76. Found: C; 63.61, H; 5.94, N; 11.71.

EXAMPLES 5 AND 6

In substantially the same manner as Example 4, 7-(7-amino-5-azaspiro[2,4]heptan-5-yl)-6-fluoro-1-(2,4-difluorophenyl)-1,4-dihydro-4-oxoquinoline-3-carboxylic acid (compound 34) melting at 226°–228° C. and 7-(7-amino-5-azaspiro[2,4]heptan-5-yl)-1-cyclopropyl-6-fluoro-1,4-dihydro-4-oxo-1,8-naphthyridine-3-carboxylic acid (compound 35) melting at 256°–257° C. were synthesized.

EXAMPLE 7

10-(7-Amino-5-azaspiro[2,4]heptan-5-yl)-9-fluoro-2,3-dihydro-3-(S)-methyl-7-oxo-7H-pyrido[1,2,3-de][1,4-]benzoxazine-6-carboxylic acid (compound 36)

300 mg of 9,10-difluoro-2,3-dihydro-3-(S)-methyl-7-oxo-7H-pyrido[1,2,3-de][1,4]benzoxazine-6-carboxylic acid $BF_2$-chelate and 250 mg of compound 11 were added to 5 ml of dimethylacetamide and the mixture was stirred at room temperature for 3 hours. The solvent was then removed under reduced pressure and 1 ml of triethylamine and 30 ml of 95% methanol were added to the residue. The mixture was refluxed for 6 hours. After cooling, the solvent was removed under reduced pressure and the residue was triturated with ethanol. The resulting crystals were collected by filtration and treated as described in Example 4 to remove the tert-butoxycarbonyl group. The procedure gave 170 mg of title compound 36 as a crude product. This product was dissolved in ethanol-concentrated aqueous ammonia, treated with activated carbon and recrystallized to yield 110 mg of title compound 36.

m.p.: 236°–237° C.

EXAMPLE 8

1-Cyclopropyl-7-(4,7-diazaspiro[2,5]octan-7-yl)-6-fluoro-1,4-dihydro-4-oxoquinoline-3-carboxylic acid (compound 37)

200 mg of 1-cyclopropyl-6,7-difluoro-1,4-dihydro-4-oxoquinoline-3-carboxylic acid and 200 mg of crude 4,7-diazaspiro[2,5]octane 25 were added to 10 ml of dimethyl sulfoxide followed by the addition of 0.3 ml of triethylamine. The mixture was heated on a bath of 120° C. for 2 hours. The solvent was then removed under reduced pressure and the residue was subjected to silica gel column chromatography, eluting with chloroform-methanol-water=15:3:1 (v/v). The crude product obtained from the fraction containing the desired compound was recrystallized from ethanol-concentrated aqueous ammonia to give 160 mg of title compound 37.

m.p.: 243°–245° C. (decomp.).

Elemental analysis: $C_{19}H_{20}N_3O_3F\cdot\frac{1}{4}H_2O$: Calcd.: C; 63.03, H; 5.71, N; 11.61. Found: C; 62.88, H; 5.99, N; 11.64.

$^1$H-NMR (NaOD-DSS) δppm: 0.97 (2H, t, J=6 Hz), 1.12 (2H, m), 1.36 (2H, br t), 1.48 (2H, br t, J=6 Hz), 7.64 (1H, d, J=8 Hz), 7.92 (1H, d, J=14 Hz), 8.52 (1H, s).

EXAMPLE 9

7-(7-Acetoxy-5-azaspiro[2,4]heptan-5-yl)-8-chloro-1-cyclopropyl-6-fluoro-1,4-dihydro-4-oxoquinoline-3-carboxylic acid (compound 38)

360 mg of 8-chloro-1-cyclopropyl-6,7-difluoro-3-oxo-3,4-dihydroquinoline-3-carboxylic acid and 1 ml of triethylamine were added to a solution of 900 mg of 7-acetoxy-5-azaspiro[2,4]heptane (compound 69) in 10 ml of dry acetonitrile and the mixture was refluxed for 2.5 days. (After 3 hours, 400 mg of the above azaspiroheptane was further added.) The reaction mixture was diluted with chloroform and the organic layer was washed with 10% aqueous citric acid and dried. The solvent was then removed under reduced pressure.

The residue was subjected to silica gel (20 g) column chromatography eluting with chloroform and 3% methanol-chloroform.

The fractions containing the object compound were collected and the solvent was removed under reduced pressure. A small amount of ethanol was added to the residue and the mixture was warmed and allowed to stand. The resulting crystals were collected by filtration and washed with diisopropyl ether to give 174 mg of title compound 38.

m.p.: 179°–182° C.

$^1$H-NMR (CDCl$_3$) δ: 0.72–1.00 (4H, m), 1.00–1.40 (4H, m), 2.10 (3H, s), 7.95 (1H, d), 8.87 (1H, s).

EXAMPLE 10

7-(7-Hydroxy-5-azaspiro[2,4]heptan-5-yl)-8-chloro-1-cyclopropyl-6-fluoro-1,4-dihydro-4-oxoquinoline-3-carboxylic acid (compound 39)

174 mg of 7-(7-acetoxy-5-azaspiro[2,4]heptan-5-yl)-8-chloro-1-cyclopropyl-1-fluoro-1,4-dihydro-4-oxoquinoline-3-carboxylic acid 38 was suspended in 8 ml of ethanol followed by the addition of 1.5 ml of 1N aqueous sodium hydroxide. The mixture was stirred at room temperature for 10 minutes. The solvent was then removed under reduced pressure and chloroform was added to the residue. The mixture was washed with water. The aqueous layer was acidified with 1N hydrochloric acid and extracted with chloroform. The extract was dried and the solvent was removed under reduced pressure. Finally, the residue was recrystallized from aqueous ammonia-ethanol to give 127 mg of title compound 39.

m.p.: 242°–244° C.

$^1$H-NMR (1N NaOD) δ: 0.53–1.17 (8H, m), 2.98, 3.35 & 3.74 (each 1H), 4.09–4.13 (3H, m), 7.59 (1H, d), 8.45 (1H, s).

Elemental analysis, for $C_{19}H_{18}N_2O_4ClF$ Calcd C; 58.10, H; 4.62, N; 7.13. Found: C; 58.39, H; 4.65, N; 7.27.

EXAMPLE 11

7-(7-Hydroxyimino-5-azaspiro[2,4]heptan-5-yl)-8-chloro-1-cyclopropyl-6-fluoro-1,4-dihydro-4-oxoquinoline-3-carboxylic acid (compound 40)

0.5 ml of anisole was added to 678 mg of 5-tert-butoxycarbonyl-7-hydroxyimino-5-azaspiro[2,4]heptane (compound 67) followed by the addition of 5 ml of trifluoroacetic acid with ice-cooling. The mixture was stirred at the same temperature for 30 minutes. The solvent was then removed under reduced pressure and 100 ml of dry acetonitrile was added to the residue. Then, 300 mg of 8-chloro-1-cyclopropyl-6,7-difluoro-4-oxo-3,4-dihydroquinoline-3-carboxylic acid and 1 ml of triethylamine were added and the mixture was refluxed for 9 hours. The solvent was then removed under reduced pressure, methanol was added to the residue, and the insolubles were filtered off. The mother liquor was allowed to stand for 2 days and the resulting crystals were collected by filtration and recrystallized from aqueous ammonia-ethanol to give 58 mg of title compound 40.

m.p.: 239°–242° C.

$^1$H-NMR (1N NaOD) δ: 0.70–1.05 (8H, m), 3.50 (2H, s), 4.09–4.12 (1H, m), 4.29 (2H, s), 7.65 (1H, d, J=15 Hz), 8.46 (1H, s).

Elemental analysis, for $C_{19}H_{17}N_3O_4FCl$: Calcd.: C; 56.24, H; 4.22, N; 10.35. Found: C; 56.34, H; 4.34, N; 10.32.

EXAMPLE 12

(−)-10-(7-Amino-5-azaspiro[2,4]heptan-5-yl)-9-fluoro-2,3-dihydro-3-(S)-methyl-7-oxo-7H-pyrido[1,2,3-de][1,4]benzoxazine-3-carboxylic acid (compound 36b)

280 mg of (−)-9,10-difluoro-2,3-dihydro-3-(S)-methyl-7-oxo-7H-pyrido[1,2,3-de][1,4]benzoxazine-3-carboxylic acid $BF_2$-chelate was suspended in 4 ml of dry dimethyl sulfoxide followed by the addition of 450 mg of compound 68b and 520 mg of triethylamine at room temperature. The mixture was stirred for 45 minutes. Then, under ice-cooling, water was added slowly to the reaction mixture and the resulting crystals were collected by filtration. 30 ml of 90% methanol and 2 ml of triethylamine were added to the crystals and the mixture was refluxed for 17 hours. The solvent was removed under reduced pressure and the residue was recrystallized from aqueous ammonia-ethanol to give 73 mg of title compound 36b.

m.p.: 217°–238° C.

$[α]_D$ −109.22° (c=0.683, 1N NaOH).

$^1$H-NMR (1N NaOD) δ: 0.38–0.68 (4H, m), 1.31 (3H, d, J=5 Hz), 2.91–4.39 (8H, m), 7.28 (1H, d, J=15 Hz), 8.17 (1H, s).

Elemental analysis, for $C_{19}H_{20}N_3O_4F.1\frac{1}{4}H_2O$. Calcd.: C; 57.64, H; 5.73, N; 10.61. Found: C; 57.64, H; 5.21, N; 10.81.

EXAMPLE 13

(−)-7-(7-Amino-5-azaspiro[2,4]heptan-5-yl)-1-cyclopropyl-6-fluoro-4-oxo-1,4-dihydro-1,8-naphthyridine-3-carboxylic acid (compound 35b)

282.5 mg of 7-chloro-1-cyclopropyl-6-fluoro-4-oxo-1,4-dihydro-1,8-naphthyridine-3-carboxylic acid, 200 mg of compound 68b and 1 g of triethylamine were added to 6 ml of dimethyl sulfoxide. The mixture was stirred at 110° C. for 1 hour. The solvent was removed under reduced pressure and diethyl ether was added to the residue. The resulting precipitate was collected by filtration and 1N hydrochloric acid was added thereto. The mixture was washed with chloroform. The aqueous solution was made alkaline with 1N aqueous sodium hydroxide and rewashed with chloroform. This alkaline solution was then adjusted to pH 7.1 with concentrated hydrochloric acid under ice-cooling and the resulting colorless crystals were collected by filtration, washed with water, ethanol and ether, and dried. The crystals were then recrystallized from concentrated aqueous ammonia-ethanol to give 283 mg of title compound 35b as colorless fine needles.

m.p.: 240°–250° C. (decomp.)

$[α]_D$ −13.6° (c=0.66, 1N NaOH).

Elemental analysis, for $C_{18}H_{19}N_4O_3F.\frac{1}{4}H_2O$ Calcd.: C; 59.58, H; 5.42, N; 15.44. Found: C; 59.68, H; 5.40, N; 15.36.

EXAMPLE 14

7-(7-Amino-5-azaspiro[2,4]heptan-5-yl)-1,4-dihydro-6-fluoro-1-(2-methyl-2-propyl)-4-oxo-1,8-naphthyridine-3-carboxylic acid (compound 41b)

200 mg of compound 68b was suspended in 15 ml of acetonitrile followed by the addition of 3 ml of triethylamine and under refluxing, 327 mg of ethyl 7-chloro-1,4-dihydro-6-fluoro-1-(2-methyl-2-propyl)-4-oxo-1,8-naphthyridine-3-carboxylate was added in small portions. After 1 hour of refluxing, the solvent was removed under reduced pressure and water was added to the residue. The mixture was extracted with chloroform and n-butanol. The organic layers were combined and the solvents were removed. Diethyl ether was added to the residue and the resulting precipitate was collected by filtration to give 516 mg of a colorless powder.

$^1$H-NMR (DMSO-$d_6$) δ: 0.77–1.05 (4H, m), 1.27 (3H, t, J=7 Hz), 1.82 (9H, s), 2.86–3.36 (4H, m), 4.20 (1H, m), 4.21 (2H, q, J=7 Hz), 7.91 (1H, d, J=13 Hz), 8.68 (1H, s).

510 mg of the above colorless powder was suspended in 2 ml of water followed by the addition of 2 ml of 1N aqueous sodium hydroxide and the mixture was refluxed for 40 minutes. To the reaction mixture was added 5 ml of water and pH was adjusted to 7.5 with 0.25N hydrochloric acid. The resulting crystals were collected by filtration and washed with water. The crystals were dried and recrystallized from ethanol to give 171 mg of title compound 41b as a colorless powder.

m.p.: 243°–247° C. (decomp.)

$[α]_D$ −16.7° (c=0.504, 1N NaOH).

$^1$H-NMR (DMSO-$d_6$) δ: 0.45–0.82 (4H, m), 1.87 (9H, s), 2.80–3.80 (4H, m), 4.00 (1H, m), 7.98 (1H, d, J=13 Hz), 8.82 (1H, s).

Elemental analysis, for $C_{19}H_{23}H_4O_3F.\frac{1}{4}H_2O$. Calcd.: C 59.52, H 6.31, N 14.61. Found: C 59.17, H 6.17, N 14.49.

REFERENCE EXAMPLE 5

Synthesis of 2,4,5-trifluoro-3-methylbenzoic acid

1) Dimethyl 3,5,6-trifluoro-4-nitromethylphthalate (compound 42)

200 g of dimethyl tetrafluorophthalate was dissolved in 400 ml of nitromethane (Ishikawa, Suzuki & Tanabe: Nippon Kagaku Kaishi, 1976, 200) and the solution was cooled on an ice-salt bath. At an internal temperature of 15°–20° C., 171 g of 1,8-diazabicyclo[5,4,0]-7-undecene was added dropwise over a period of 30 minutes. After completion of the dropwise addition, the mixture was further stirred at an internal temperature of 10° C. for 30 minutes, then, the mixture was poured into a mixture of 1.5 liters of 1N hydrochloric acid and 1 liter of ice.

The reaction mixture was extracted with benzene and the organic layer was washed with water and dried over anhydrous sodium sulfate. The solvent was then removed under reduced pressure and the residue was subjected to silica gel (500 g) column chromatography eluting with benzene. The procedure gave 195 g of title compound 42 as a yellow oil.

$^1$H-NMR (CDCl$_3$) δ: 3.88 (3H, s), 3.94 (3H, s), 5.60 (2H, t, J=2 Hz).

2) Dimethyl 4-dimethylaminomethyl-3,5,6-trifluorophthalate (compound 43)

At atmospheric pressure, a mixture of 5.0 g of compound 42, 20 ml of Raney nickel, 15 ml of 35% formalin and 70 ml of ethanol was subjected to a reduction reaction for 22 hours.

The catalyst was then filtered off and the filtrate was concentrated under reduced pressure. The residue was dissolved in chloroform and the solution was washed with water and dried over anhydrous sodium sulfate. The solvent was then removed under reduced pressure to give 5.2 g of title compound 43 as a light yellow oil.

$^1$H-NMR (CDCl$_3$) δ: 2.32 (6H, s), 3.70 (2H, t, J=2 Hz), 3.96 (3H, s), 3.98 (3H, s).

3) 2,5,6-Trifluoro-3,4-di(methoxycarbonyl)phenylmethylenetrimethylammonium iodide (compound 44)

5.2 g of compound 42 was dissolved in 50 ml of ethanol followed by the addition of 5 ml of methyl iodide and the mixture was allowed to stand for 1.5 hours. The resulting crystals were collected by filtration. The procedure gave 3.6 g of colorless crystals of title m.p.: 186°-190° C. (decomp.)

4) Dimethyl 3,5,6-trifluoro-4-methylphthalate (compound 45)

a) A mixture of 4.6 g of compound 42, 6.8 g of tributyltin hydride, 300 mg of α,α'-azobisisobutyronitrile and 70 ml of benzene was refluxed for 4 hours. The reaction mixture was then concentrated under reduced pressure and the residue was subjected to silica gel (50 g) column chromatography eluting with benzene. The procedure gave 2.45 g of title compound 45 as a light yellow coil.

b) A mixture of 17.0 g of compound 44, 30 ml of Raney nickel and 350 ml of ethanol was subjected to a reduction reaction at atmospheric pressure under irradiation with a tungsten lamp for 25.5 hours.

The catalyst was then filtered off and the filtrate was concentrated under reduced pressure. To the residue was added water and extracted with chloroform. The organic layer was dried over anhydrous sodium sulfate. The solvent was then removed under reduced pressure to give 9.62 g of title compound 45 as a yellow oil.

$^1$H-NMR (CDCl$_3$) δ: 2.29 (3H, t, J=2 Hz), 3.91 (3H, s), 3.93 (3H, s).

5) 3,5,6-Trifluoro-4-methylphthalic acid (compound 46)

A mixture of 2.45 g of compound 45, 10 ml of acetic acid and 20 ml of concentrated hydrochloric acid was refluxed for 12 hours. The reaction mixture was then concentrated under reduced pressure and the residue was extracted with diethyl ether. The extract was dried over anhydrous sodium sulfate. The solvent was then removed under reduced pressure to give 2.1 g of title compound 46 as colorless crystals.

m.p.: 155°-160° C.

6) 2,4,5-Trifluoro-3-methylbenzoic acid (compound 47)

10.1 g of compound 46 was dissolved in 40 ml of water and the mixture was heated in a sealed tube on a bath of 200° C. for 4 days. The reaction mixture was then extracted with chloroform and the extract was dried over anhydrous sodium sulfate. Finally, the solvent was removed under reduced pressure to yield 6.2 g of title compound 47 as light yellow crystals.

m.p.: 89°-90° C.

$^1$H-NMR (CDCl$_3$) δ: 2.29 (3H, t, J=2 Hz), 7.56–7.84 (1H, m), 8.1–8.6 (1H, broad).

REFERENCE EXAMPLE 6

Ethyl 2,4,5-trifluoro-3-methylbenzoylacetate (compound 48)

9.89 g of 2,4,5-trifluoro-3-methylbenzoic acid 47 was dissolved in 200 ml of benzene followed by the addition of 40 ml of thionyl chloride and the mixture was refluxed for 14 hours. The reaction mixture was then concentrated to dryness under reduced pressure and 200 ml of benzene was added to the residue. The mixture was reconcentrated to dryness under reduced pressure and the resulting crude acid chloride was dissolved in 200 ml of diethyl ether.

A mixture of 1.26 g of magnesium, 250 ml of ethanol and 6 ml of carbon tetrachloride was stirred at room temperature for 1 hour, at the end of which time 50 ml of a diethyl ether solution of 8.34 g of diethyl malonate was added dropwise. The mixture was then stirred at room temperature for 1 hour. The reaction mixture was then concentrated to dryness under reduced pressure and the residue was dissolved in 300 ml of diethyl ether. To this solution was added the above-prepared diethyl ether solution of acid chloride dropwise over a period of 10 minutes and the mixture was stirred at room temperature for 4 days. Thereafter, 100 ml of 1N hydrochloric acid was added and after stirring, the ether layer was taken, washed with water and dried over anhydrous sodium sulfate. The solvent was then removed under reduced pressure. To the residue were added 500 ml of water and 500 mg of p-toluenesulfonic acid and the mixture was refluxed for 7 hours. The reaction mixture was then extracted with chloroform, the organic layer was dried over anhydrous sodium sulfate and the solvent was removed under reduced pressure. The residue was subjected to silica gel column chromatography using benzene as an eluent. The procedure gave 6.1 g of title compound 48 as a colorless oil. When allowed to stand, this oil underwent partial crystallization.

REFERENCE EXAMPLE 7

Ethyl 2-cyclopropylaminomethylene-3-oxo-3-(2,4,5-trifluoro-3-methyl)phenylpropionate (compound 49)

A mixture of 1.57 g of compound 48, 6 ml of ethyl orthoformate and 6 ml of acetic anhydride was heated at 120° C. with stirring for 3 hours. The reaction mixture was then concentrated to dryness under reduced pressure. The residue was dissolved in 25 ml of 1,2-dichloromethane followed by the addition of 10 ml of a solution prepared by dissolving 400 mg of cyclopropylamine in 1,2-dichloromethane. The mixture was stirred at room temperature for 14 hours. The reaction mixture was then concentrated to dryness under reduced pressure to give 2 g of title compound 49 as colorless crystals melting at 61°–64° C.

REFERENCE EXAMPLE 8

Ethyl 1-cyclopropyl-6,7-difluoro-8-methyl-4-oxo-1,4-dihydroquinoline-3-carboxylate (compound 50)

1.97 g of compound 49 was dissolved in 30 ml of dry dioxane followed by the addition of 360 mg of 60% sodium hydride and the mixture was stirred at room temperature for 18 hours. After 10 ml of 1N hydrochloric acid was added, the reaction mixture was concentrated under reduced pressure and water was added to the residue. The resulting crystals were collected by filtration and washed with water and small amounts of ethanol and diethyl ether. The procedure gave 1.35 g of title compound 50 as colorless crystals.

m.p.: 204°–210° C.

REFERENCE EXAMPLE 9

1-Cyclopropyl-6,7-difluoro-8-methyl-4-oxo-1,4-dihydroquinoline-3-carboxylic acid (compound 51)

A mixture of 1.30 g of compound 50 and 10 ml of concentrated hydrochloric acid was refluxed for 3 hours, at the end of which time 50 ml of water was added to the reaction mixture. The resulting crystals were collected by filtration and washed with water and ethanol to give 1.12 g of title compound 51.

m.p.: 241°–242° C.

REFERENCE EXAMPLE 10

1-Cyclopropyl-6,7-difluoro-8-methyl-4-oxo-1,4-dihydroquinoline-3-carboxylic acid $BF_2$-chelate (compound 52)

420 mg of compound 50 was suspended in 30 ml of diethyl ether followed by the addition of 2 ml of boron trifluoride-diethyl ether complex and the mixture was stirred at room temperature for 24 hours. The resulting crystals were collected by filtration and washed with diethyl ether. The procedure gave 487 mg of title compound 52 as yellow crystals m.p.: 275°–278° C.

EXAMPLE 15

(−)-7-(7-Amino-5-azaspiro[2,3]heptan-5-yl)-1-cyclopropyl-6-fluoro-8-methyl-4-oxo-1,4-dihydroquinoline-3-carboxylic acid (compound 55b)

A mixture of 340 mg of compound 52, 330 mg of 7-tert-butoxycarbonylamino-5-azaspiro[2,3]heptane (compound 11b), 150 mg of triethylamine and 5 ml of dimethyl sulfoxide was stirred at room temperature for 5 days. The reaction mixture was then dissolved in 100 ml of chloroform and the solution was washed with water. The organic layer was dried over anhydrous sodium sulfate and the solvent was removed under reduced pressure.

The residue was subjected to silica gel (30 g) column chromatography eluting with chloroform-methanol (95:5). The resulting 7-(7-tert-butoxycarbonylamino-5-azaspiroheptan-5-yl)-1-cyclopropyl-6-fluoro-8-methyl-4-oxo-1,4-dihydroquinoline-3-carboxylic acid $BF_2$-chelate was dissolved in 30 ml of 70% methanol followed by the addition of 1 ml of triethylamine and the mixture was refluxed for 3 hours.

The reaction mixture was then concentrated under reduced pressure and 20 ml of 10% citric acid was added to the residue. The mixture was extracted with chloroform and the organic layer was dried over anhydrous sodium sulfate. The solvent was then removed under reduced pressure. To the residue was added 10 ml of trifluoroacetic acid and the mixture was stirred at room temperature for 20 minutes and then concentrated to dryness under reduced pressure. To the residue was added hydrochloric acid and the mixture was washed with chloroform. Under ice-cooling, the aqueous layer was adjusted to pH 12 with aqueous sodium hydroxide and washed with chloroform. The aqueous layer was adjusted to pH 7.4 and extracted with chloroform. The organic layer was dried over anhydrous sodium sulfate and the solvent was removed. The residue was recrystallized twice from aqueous ammonia-ethanol to yield 52 mg of title compound 55b as colorless crystals.

m.p.: 180°–182° C.

$[\alpha]_D$ −128.0° (c=0.125, 1N NaOH).

$^1$H-NMR (CDCl$_3$) δ: 0.61–0.63 (1H, m), 0.64–0.74 (2H, m), 0.84–0 88 (1H, m), 0.90–0.97 (2H, m), 1.19–1.28 (2H, m), 2.62 (3H, s), 3.19–3.21 (1H, m), 3.29 (1H, d, J=9 Hz), 3.36–3.39 (1H, m), 3.84 (1H, d, J=9 Hz), 3.99–4.03 (1H, m), 4.05–4.08 (1H, m), 7.85 (1H, d, J=13.5 Hz), 8.86 (1H, s).

EXAMPLE 16

Optically active 7-[7-(tert-butoxycarbonylamino)-5-azaspiro[2,4]heptan-5-yl]-8-chloro-1-cyclopropyl-6-fluoro-1,4-dihydro-4-oxoquinoline-3-carboxylic acid (compound 56a and compound 56b)

500 mg of 8-chloro-1-cyclopropyl-6,7-difluoro-1,4-dihydro-4-oxoquinoline-3-carboxylic acid, 440 mg of compound 11b and 2 ml of triethylamine were dissolved in 20 ml of acetonitrile and the solution was refluxed overnight. After cooling, the solvent was removed under reduced pressure and the resulting precipitate was collected by filtration, washed successively with water, acetonitrile, ethanol and ether and dried under reduced pressure. The procedure gave 560 mg of title compound 56b as light yellow crystals. Using compound 11a in otherwise the same manner, title compound 56a was also synthesized.

56b: light yellow crystals, m.p. 216°–217° C.

$[\alpha]_D$ −134.7° (c=1.653, chloroform).

$^1$H-NMR (CDCl$_3$) δppm: 0.4–1.6 (8H, m), 1.45 (9H, s), 3.33 (1H, d, J=9 Hz), 3.60 (1H, d, J=9 Hz), 3.7–4.5 (4H, m), 4.7–5.1 (1H, br d), 7.95 (1H, d, J=12.9 Hz), 8.87 (1H, s).

Elemental analysis, for $C_{24}H_{27}N_3O_5ClF$. Calcd.: C; 58.60, H; 5.53, N; 8.54. Found: C; 58.43, H; 5.59, N; 8.40.

56a: light yellow crystals, m.p. 215°–216° C.

$[\alpha]_D$ +131.4° (c=0.77, chloroform)

Elemental analysis, for $C_{24}H_{27}N_3O_5ClF$ Calcd.: C; 58.60, H; 5.53, N; 8.54. Found: C; 58.37, H; 5.58, N; 8.44.

The NMR spectrum of 56a was in complete agreement with that of 56b.

EXAMPLE 17

Optically active 7-(7-amino-5-azaspiro2,4]heptan-5-yl)8-chloro-1-cyclopropyl-6-fluoro-1,4-dihydro-4-oxoquinoline-3-carboxylic acid (compound 32a and compound 32b)

0.5 ml of anisole and 10 ml of trifluoroacetic acid were added to 520 mg of compound 56b with ice-cooling. Then, at room temperature, the mixture was stirred for 30 minutes. The solvent was then removed under reduced pressure and water was added to the residue. The mixture was adjusted to a pH of about 11-12 with 1N aqueous sodium hydroxide under ice-cooling. This aqueous solution was washed twice with chloroform and adjusted to about pH 7 with concentrated hydrochloric acid and 10% citric acid. This solution was extracted with chloroform 3 times and the extract was washed with water and dried. The solvent was then removed under reduced pressure and the solid residue was recrystallized from ethanol-aqueous ammonia to give 328 mg of title compound 32b as light yellow crystals. Similarly, title compound 32a was prepared from compound 56a. Compound 32b: light yellow crystals m.p. 166°-170° C. (decomp.).

$[\alpha]_D$ −112.6° (c=0.43, 1N aqueous NaOH).

$^1$H-NMR (CDCl$_3$, 500 MHz) δppm: 0.6-1 25 (8H, m), 3.08 (1H, t, J=4.4 Hz), 3.30 (1H, d, J=10.3 Hz), 3.41 (1H, d, J=9.5 Hz), 3,96 (1H, d, J=9.5 Hz), 4.11 (1H, m), 4.24 (1H, m), 7.75 (1H, d, J=13.5 Hz), 8.55 (1H, s).

Elemental analysis: C$_{19}$H$_{19}$N$_3$O$_3$ClF.½H$_2$O. Calcd.: C; 56.93, H; 5.03, N; 10.48. Found: C; 57.16, H; 5.44, N; 10.46.

Compound 32a: light yellow crystals $[\alpha]_D$ +110.3° (c=0.435, 1N aqueous NaOH).

Elemental analysis, for C$_{19}$H$_{19}$N$_3$O$_3$ClF.½H$_2$O. Calcd.: C; 56.93, H; 5.03, N; 10.48. Found: C; 56.87, H; 5.37, N; 10.32.

The NMR spectrum of 32a was in complete agreement with that of 32b.

REFERENCE EXAMPLE 11

8-Chloro-1-cyclopropyl-6,7-difluoro-1,4-dihydro-4-oxoquinoline-3-carboxylic acid BF2-chelate (compound 57)

15 ml of borontrifluoride diethyl ether complex was added to a suspension of 3 g of 8-chloro-1-cyclopropyl-6,7-difluoro-1,4-dihydro-4-oxoquinoline-3-carboxylic acid in 30 ml of diethyl ether. The mixture was stirred at room temperature for 2 hours. A precipitate was collected by filtration and was washed with ether several times, then dried under reduced pressure to yield 3.35 g of title compound 57 as a colorless powder.

m.p.: 245°-260° C. (decomp.).

Elemental analysis, for C$_{13}$H$_7$NO$_3$BClF$_4$: Calcd.: C; 44.94, H; 2.03, N; 4.03. Found: C; 45.07, H; 2.21, N; 4.12.

EXAMPLE 18

(−)-7-(7-Amino-5-azaspiro[2,4]heptan-5-yl)-8-chloro-1-cyclopropyl-6-fluoro-1,4-dihydro-4-oxoquinoline-3-carboxylic acid (compound 32a)

A mixture of 700 mg of compound 57, 450 mg of 7-amino-5-azaspiro[2,4]heptane dihydrochloride (compound 68b), 610 mg of triethylamine and 7 ml of dimethyl sulfoxide was stirred at room temperature for 24 hours. Water was added to the mixture and a yellow precipitate was collected by filtration and dried. 50 ml of 95% methanol and 1 ml of triethylamine were added to the precipitate. The mixture was stirred at room temperature for 1 hour. The solvent was removed under reduced pressure and 1N hydrochloric acid was added to the residue. The mixture was washed with chloroform, and the aqueous layer was made alkaline with 1N aqueous sodium hydroxide. The aqueous layer was washed with chloroform again. The pH of the alkaline aqueous solution was adjusted to pH 7.1 with concentrated hydrochloric acid under cooling. The aqueous solution was extracted with chloroform three times. The extract was washed with saturated aqueous sodium chloride, then dried. The solvent was removed under reduced pressure. The residue was recrystallized from concentrated ammonia, water and ethanol to yield 610 mg of title compound 32a as colorless crystals.

REFERENCE EXAMPLE 12

An alternative synthesis of 4,7-dioxo-5-[1-(R)-phenylethyl]-5-azaspiro[2,4]heptane 12

1) 1-Acetylcyclopropane-1-carboxylic acid (compound 58)

To a solution of 268.6 g of compound 2 in 400 ml of ethanol was added dropwise at room temperature an aqueous solution of 75.67 g of sodium hydroxide in 200 ml of water in 20 minutes. The mixture was stirred at room temperature for 2 hours. 1,500 ml of dichloromethane and 500 ml of water were added to the mixture. The mixture was shaken, then the aqueous layer was separated. The aqueous layer was washed with two 500 ml portions of dichloromethane. The aqueous layer was adjusted to pH 2 with concentrated hydrochloric acid under cooling, and the mixture was extracted with 1,500 ml of dichloromethane. The aqueous layer was extracted with 500 ml of dichloromethane, and the extracts were combined. The combined organic layer was washed with water and dried over anhydrous sodium sulfate. The solvent was removed under reduced pressure. The residue was distilled under reduced pressure to yield 232 g of title compound 58 as a colorless oil.

$^1$H-NMR (CDCl$_3$) δppm: 1.6-2.0 (4H, m), 2.21 (3H, s).

2) N-[1-(R)-phenylethyl]-1-acetyl-1-cyclopropanecarboxamide (compound 59)

A solution of 232 g of compound 58, 1,500 ml of chloroform and 250.8 ml of triethylamine was cooled on a dry ice-acetone bath to an inner temperature of −40° C. 215.9 g of ethyl chloroformate was added dropwise to the solution in 20 minutes. The mixture was stirred under cooling keeping the inner temperature at about −30° C. for 40 minutes. The mixture was cooled to inner temperature of −40° C., and 241.1 g of R-(+)-1-phenylethylamine was added to the mixture. The mixture was stirred for 1.5 hours. The mixture was washed with 1N hydrochloric acid, water, saturated sodium bicarbonate aqueous solution and water. The chloroform layer was dried over anhydrous sodium sulfate. The solvent was removed under reduced pressure to yield 489.3 g of title compound 59 as a colorless oil.

$^1$H-NMR (CDCl$_3$) δppm: 1.50 (3H, d, J=7.2 Hz), 1.4-1.6 & 1.7-1.9 (2H each, m), 1.95 (3H, s), 5.10 (1H, q, J=7.2 Hz), 7.30 (5H, s).

3) N-[1-(R)-phenylethyl]-1-(1,1-ethylenedioxyethyl)-1-cyclopropanecarboxamide (compound 60)

A mixture of 248.4 g of compound 59, 800 ml of benzene, 230 ml of ethylene glycol and 10.0 g of p-toluenesulfonic acid monohydrate was refluxed for 24 hours. Water formed during the reaction was removed. After cooling, 500 ml of water and 500 ml of benzene were added to the mixture. The mixture was then shaken. The organic layer was separated and washed with saturated sodium bicarbonate aqueous solution and water. The organic layer was dried over anhydrous sodium sulfate and the solvent was removed under reduced pressure to yield 227.8 g of title compound 60.

$^1$H-NMR (CDCl$_3$) δppm: 0.7–0.95 & 1.0–1.2 (2H each, m), 1.48 (3H, s), 1.47 (3H, d, J=7.2 Hz), 3.98 (4H, s), 5.11 (1H, q, J=7.2 Hz), 7.31 (5H, s), 7.75 (1H, br s).

4) N-[1-(R)-phenylethyl]-1-(2-bromo-1,1-ethylenedioxyethyl)-1-cyclopropane-carboxamide (compound 61)

145.4 g of bromine was added dropwise to 436 ml of dioxane at room temperature in 30 minutes. The mixture was stirred at room temperature for 30 minutes, and a solution of 227.8 g of compound 60 in 2,000 ml of dichloromethane was added to the mixture. The mixture was stirred at room temperature for 2 hours. The mixture was washed with an aqueous solution of sodium thiosulfate and water. The organic layer was dried over anhydrous sodium sulfate and the solvent was removed under reduced pressure to yield 326.0 g of title compound 61.

$^1$H-NMR (CDCl$_3$) δppm: 0.7–1.0 & 1.0–1.25 (2H each, m), 1.49 (3H, d, J=7.2 Hz), 3.69 (2H, s), 3.8–4.3 (4H, m), 5.08 (1H, q, J=7.2 Hz), 7.30 (5H, s), 7.6 (1H, br s).

5) 4,7-Dioxo-5-[1-(R)-phenylethyl]-5-azaspiro[2,4]heptane-7-ethylene acetal (compound 62)

43 g of 60% sodium hydride was added in three portions to a solution of 293 g of compound 61 in 1,500 ml of N,N-dimethylformamide at room temperature in 1.5 hours. While adding sodium hydride, the mixture was cooled to keep the inner temperature at about 30° C. The mixture was stirred at room temperature for 18 hours. The mixture was poured into ice and extracted with ethyl acetate. The organic layer was separated and washed with water. The organic layer was dried over anhydrous sodium sulfate. The solvent was removed under reduced pressure to yield 203.3 g of title compound 62 as a dark oil.

$^1$H-NMR (CDCl$_3$) δppm: 0.98–1.38 (4H, m), 1.50 (3H, d, J=7.2 Hz), 3.07 & 3.41 (1H each, d, J=10.2 Hz), 3.83 (4H, s), 5.61 (1H, q, J=7.2 Hz), 7.30 (5H, s).

6) 4,7-Dioxo-5-[1-(R)-phenylethyl]-5-azaspiro[2,4]heptane (compound 12)

A mixture of 203.3 g of compound 62, 300 ml of 1N hydrochloric acid and 1,000 ml of acetone was refluxed for 1.5 hours. Then, the solvent was removed under reduced pressure and the residue was extracted with ethyl acetate. The extract was washed with water and dried over anhydrous sodium sulfate. The extract was decolorized with active charcoal and the solvent was removed under reduced pressure. The residue was purified by silica gel column chromatography (1,300 g) eluting with chloroform containing 0–10% of ethyl acetate to yield 65.7 g of title compound 12 as a colorless crystal.

$^1$H-NMR (CDCl$_3$) δppm: 1.61 (3H, d, J=7 2 Hz), 1.4–1.75 (4H, m), 3.48 & 3.88 (1H each, J=17.7 Hz), 5.81 (1H, q, J=7.2 Hz), 7.34 (5H, s).

REFERENCE EXAMPLE 13

Synthesis of 5-tert-butoxycarbonyl-7-hydroxyimino-5-azaspiro[2,4-]heptane (compound 67)

1) 7,7-Ethylenedioxy-5-[1-(R)-phenylethyl]-5-azaspiro[2,4]heptane (compound 63)

2.5 g of lithium aluminum hydride was added to a solution of 7.1 g of compound 62 in 150 ml of anhydrous tetrahydrofuran, and the mixture was refluxed for 3.5 hours. The mixture was cooled by ice and 2.5 ml of water, 2.5 ml of 15% of sodium hydroxide aqueous solution and 7.5 ml of water were added to the mixture in this order. An insoluble material was removed by filtration, and the solvent was removed from the filtrate. The residue was purified by silica gel column chromatography (100 g) eluting with a mixture of n-hexane and ethyl acetate (3:2) to yield 5.67 g of title compound 63.

$^1$H-NMR (CDCl$_3$) δppm: 0.40–0.60 (2H, m), 0.76–0.96 (2H, m), 1.36 (3H, d, J=7.2 Hz), 2.40–2.88 (4H, m), 3.77 (4H, s), 7.18–7.50 (5H, m).

2) 7,7-Ethylenedioxy-5-azaspiro[2,4]heptane (compound 64)

A mixture of 3.89 g of compound 63, 50 ml of ethanol and 4 g of 5% palladium-on-carbon was shaken under a hydrogen atmosphere of 4 atm. The reaction vessel was heated externally by a tungsten lamp during the reduction reaction. The reduction reaction was continued for 3 hours. The catalyst was removed by filtration. The solvent was removed under reduced pressure from the filtrate to yield 2 g of title compound 64.

$^1$H-NMR (CDCl$_3$) δppm: 0.44–0.64 (2H, m), 0.72–0.92 (2H, m), 3.03 & 3.05 (2H each, s), 3.86 (4H, s).

3) 5-tert-Butoxycarbonyl-7,7-ethylenedioxy-5-azaspiro[2,4]heptane (compound 65)

1,515 g of triethylamine and 3.05 g of di-tert-butyl dicarbonate were added to an ice-cooled solution of 1.98 g of compound 64 in 25 ml of anhydrous dichloromethane. The mixture was stirred at room temperature for 30 minutes. The solvent was removed under reduced pressure. The residue was extracted with chloroform and the extract was washed with water. The solvent was removed under reduced pressure. The residue was purified by silica gel column chromatography (50 g) eluting with a mixture of n-hexane and ethyl acetate (3:1) to yield 3.21 g of title compound 65.

4) 5-tert-Butoxycarbonyl-7-oxo-5-azaspiro[2,4]heptane (compound 66)

A mixture of 3.15 g of compound 65, 30 ml of acetone and 5 ml of 1N hydrochloric acid was refluxed for 30 minutes. The solvent was removed under reduced pressure. The residue was extracted with chloroform and the extract was dried. The solvent was removed under reduced pressure to yield 1.94 g of title compound 66.

¹H-NMR (CDCl₃) δppm: 1.00–1.20 & 1.30–1.50 (2H each, m), 4.49 (9H, s), 3.78 (2H, m), 3.95 (2H, s).

5-tert-Butoxycarbonyl-7-hydroxyimino-5-azaspiro[2,4]heptane (compound 67)

1.25 g of hydroxylamine hydrochloride and 1.8 g of triethylamine were added to a solution of 1.9 g of compound 66. The mixture was stirred at room temperature for 1 day. The solvent was removed under reduced pressure and 10% citric acid aqueous solution was added to the residue. The mixture was extracted with chloroform and the extract was washed with water. The extract was dried and the solvent was removed under reduced pressure to yield 1.86 g of title compound 67.

m.p. 117°–119° C.

¹H-NMR (CDCl₃) δppm: 0.90–1.10 & 1.14–1.34 (2H each, m), 1.45 (9H, s), 3.36 (2H, s), 4.29 (2H, s).

REFERENCE EXAMPLE 14

7-Amino-5-azaspiro[2,4]heptane dihydrochloride (compound 68b)

A mixture of 630 mg of compound 15b, 10 ml of 1N hydrochloric acid, 20 ml of ethanol and 800 mg of 5% palladium-on-charcoal was shaken under a hydrogen atmosphere of 4 atm. The reaction vessel was heated externally by a tungsten lamp during the reduction reaction. The reduction reaction was continued for 3.5 hours. The catalyst was removed by filtration and the solvent was removed to yield 350 mg of title compound 68b.

$[\alpha]_D$ −41.5° (c=1 616, H₂O).

m.p.: 230–240 (decomp., decomposition began at about 190° C.).

Elemental analysis, for C₆H₁₄N₂Cl₂·½H₂O. Calcd.: C; 37.13, H; 7.79, N; 14.43. Found: C; 37.49, H; 7.32, N; 14.59.

MS; m/Z:149 (M⁺-HCl).

¹H-NMR (D 0) δppm: 0.79–1.60 (4H, m), 3.08 (1H, d, J=12 Hz), 3.48–3.67 (3H, m), 3.93 (1H, dd, J=7 & 13.5 Hz).

REFERENCE EXAMPLE 15

7-tert-Butoxycarbonylamino-5-azaspiro[2,4]heptane (compound 11b)

A mixture of 11.8 g of compound 16b, 200 ml of ethanol and 11 g of 5% palladium-on-carbon was shaken under a hydrogen atmosphere of 4 atm. The reaction vessel was heated by a tungsten lamp during the reduction reaction. The reduction reaction was carried out for 6 hours. The catalyst was removed by filtration, and the solvent was removed under reduced pressure from the filtrate. The residue was dissolved in ethyl acetate and the solution was extracted with 10% citric acid aqueous solution. The aqueous layer was washed with ethyl acetate. The aqueous layer was made alkaline with a sodium hydroxide aqueous solution and extracted with chloroform. The extract was dried and the solvent was removed under reduced pressure to give 7.6 g of title compound 11b.

m.p.: 56°–59° C.

$[\alpha]_D$ −68.54° (c=1.742, CHCl₃).

REFERENCE EXAMPLE 16

1) Diethyl cyclobutylidenemalonate (compound 70)

A solution of 15.68 ml of titanium tetrachloride in 35.7 ml of carbon tetrachloride was added dropwise rapidly with stirring to 285 ml of tetrahydrofuran which was cooled to −30° C. 5 g of cyclobutanone and 10.83 g of diethyl malonate were added to the mixture. Then, a solution of 23.1 ml of pyridine in 50 ml of tetrahydrofuran was added dropwise in 1 hour while the temperature of the reaction mixture was maintained below −10° C. The mixture was stirred for 18 hours keeping the temperature of the mixture about 0° C. Water was added to the mixture and the mixture was extracted with diethyl ether. The ethereal layer was separated and the aqueous layer was extracted with diethyl ether. The combined organic layers were washed with a saturated sodium chloride aqueous solution, saturated sodium bicarbonate aqueous solution and a saturated sodium chloride aqueous solution. The organic layer was dried over anhydrous sodium sulfate. The solvent was removed under reduced pressure to yield 17.265 g of title compound 70 as a colorless oil.

¹H-NMR (CDCl₃) δppm: 1.29 (6H, 6, J=7.3 Hz), 1.7–2.4 (2H, m), 3.15 (4H, t, J=7.7 Hz), 4.22 (4H, q, J=7.3 Hz).

In the similar procedure, diethyl cyclopentylidenemalonate (compound 71) (¹H-NMR (CDCl₃) δppm: 1.29 (6H, t, J=7 Hz), 1.6–2.0 (4H, m), 2.6–2.8 (4H, m), 4.24 (4H, q, J=7 Hz)) and diethyl cyclohexylidenemalonate (compound 72) (¹H-NMR (CDCl₃) δppm: 1.28 (6H, t, J=7.2 Hz), 1.4–1.85 (6H, br), 2.3–2.6 (4H, br), 4.22 (4H, q, J=7.2 Hz)) were obtained.

2) Diethyl (1-nitromethyl-1-cyclobutyl)malonate (compound 73)

A mixture of 15.32 g of compound 70, 59 ml of nitromethane and 4.5 ml of tetramethylguanidine was stirred at room temperature for 16 hours. To the mixture was added 10% citric acid aqueous solution and the mixture was shaken. The organic layer was separated and washed with a saturated sodium chloride aqueous solution and dried over anhydrous sodium sulfate. The solvent was removed under reduced pressure to yield 19.03 g of title compound 73 as a yellow oil.

¹H-NMR (CDCl₃) δppm: 1.28 (6H, t, J=7.1 Hz), 1.8–2.4 (6H, m), 3.80 (1H, s), 4.20 (4H, q, J=7.1 Hz), 4.82 (2H, s).

In the similar procedure, diethyl (1-nitromethyl-1-cyclopentyl)malonate (compound 74) ¹H-NMR (CDCl₃) δppm: 1.27 (6H, t, J=7 Hz), 1.6–2.0 (8H, m), 3.79 (1H, s), 4.20 (4H, q, J=7 Hz), 4.71 (2H, s)) and diethyl (1-nitromethyl-1-cyclohexyl)malonate (compound 75) (¹H-NMR (CDCl₃) δppm: 1.27 (6H, t, J=7 Hz), 1.4–1.8 (10H, m), 3.88 (1H, s), 4.20 (4H, q, J=7 Hz), 4.96 (2H, s)) were obtained.

3) Ethyl 7-oxo-6-azaspiro[3,4]octane-8-carboxylate (compound 76)

30 ml of Raney nickel washed with water and ethanol was added to a solution of 19.03 g of compound 73 in 400 ml of ethanol. Catalytic reduction was conducted for 2 days. The catalyst was removed by filtration and the solvent was removed under reduced pressure. To the residue were added ethyl acetate and 1N hydrochloric acid and the mixture was shaken. The organic layer was dried over anhydrous sodium sulfate and the solvent was removed under reduced pressure. The residue was purified by silica gel column chromatography (100 g) eluting with chloroform containing 0–3% methanol to yield 2.97 g of title compound 76. The hydrochloric acid layer was neutralized with sodium bicarbonate and the mixture was extracted with ethyl acetate. The organic layer was dried over anhydrous sodium sulfate and the solvent was removed under reduced pressure to yield 1.58 g of title compound 76. Finally, 4.56 g total of title compound 76 was obtained.

¹H-NMR (CDCl₃) δppm: 1.28 (3H, t, J=7.1 Hz), 1.8-2.2 (6H, m), 3.21 (1H, s), 3.41 (1H, dd, J=9.7 & 1.4 Hz), 3.60 (1H, d, J=9.7 Hz), 4.20 (2H, q, J=7.1 Hz), 7.21 (1H, br).

In the similar procedure, ethyl 3-oxo-2-azaspiro[4,4]nonane-4-carboxylate (compound 77) (¹H-NMR (CDCl₃) δppm: 1.28 (3H, t, J=7.3 Hz), 2.6-2.8 (8H, br), 3.07 (1H, s), 3.01 (1H, dd, J=9.3 & 1.3 Hz), 3.45 (1H, d, J=9.3 Hz), 4.20 (2H, q, J=7.3 Hz), 7.30 (1H, br)) and ethyl 3-oxo-2-azaspiro[4,5]decane-4-carboxylate (compound 78) (¹H-NMR (CDCl₃) δppm: 1.29 (3H, t, J=7.3 Hz), 1.3-1.7 (10H, br), 3.05 (1H, s), 3.17 (1H, dd, J=9.9 & 1.4 Hz), 4.20 (2H, q, J=7.3 Hz), 7.30 (1H, br)) were obtained.

4) 7-Oxo-6-azaspiro[3,4]octane-8-carboxylic acid (compound 79)

20 ml of water and 0.8 g of sodium hydroxide were added to a solution of 1.97 g of compound 76 in 20 ml of ethanol. The mixture was refluxed for 2 hours. Ethanol was removed under reduced pressure and the aqueous layer was washed with chloroform. The aqueous layer was neutralized by 1N hydrochloric acid under ice cooling. The aqueous layer was extracted with 2-butanone, and the extract was dried over anhydrous magnesium sulfate. The solvent was removed to yield 1.57 g of title compound 79 as colorless crystals.

¹H-NMR (CDCl₃) δppm: 1.6-2.7 (6H, m), 3.15 (1H, s), 3.40 (1H, d, J=9.2 Hz), 3.60 (1H, d, J=9.2 Hz), 6.2 (1H, br).

In the similar procedure, 3-oxo-2-azaspiro[4,4]nonane-4-carboxylic acid (compound 80) (¹H-NMR (CDCl₃) δppm: 1.5-2.3 (8H, m), 3.15 (1H, d, J=9.5 Hz), 3.28 (1H, s), 3.33 (1H, d, J=9.5 Hz), 6.45 (1H, br)) and 3-oxo-2-azaspiro[4,5]decane-4-carboxylic acid (compound 81) (¹H-NMR (CDCl₃) δppm: 1.2-2.0 (10H, m), 3.06 (1H, s), 3.11 (1H, d, J=9.8 Hz), 3.48 (1H, d, J=9.8 Hz), 6.47 (1H, br)) were obtained.

5) 8-tert-Butoxycarbonylamino-7-oxo-6-azaspiro[3,4]octane (compound 82)

2.2 ml of diphenyl phosphorylazide and 1.55 ml of triethylamine were added to a suspension of 1.57 g of compound 79 in 20 ml of benzene with stirring. The mixture was refluxed for 1.5 hours. Then, 4.4 ml of tert-butanol was added to the mixture and the mixture was refluxed for 16 hours. The solvent was removed under reduced pressure. The residue was extracted with ethyl acetate and the extract was washed with a saturated sodium bicarbonate aqueous solution, a saturated sodium chloride aqueous solution, 10% citric acid aqueous solution and a saturated sodium chloride aqueous solution. The washings were extracted with ethyl acetate and the combined extracts were dried over anhydrous sodium sulfate. The solvent was removed under reduced pressure. The residue was purified by silica gel column chromatography (50 g) eluting with chloroform containing 0-3% methanol to yield 0.56 g of title compound 82.

¹H-NMR (CDCl₃) δppm: 1.48 (9H, s), 1.5-2.5 (6H, m), 3.27 (1H, d, J=9.9 Hz), 3.44 (1H, d, J=9.9 Hz), 4.18 (1H, d, J=7.7 Hz), 5.20 (1H, d, J=7.7 Hz), 7.13 (1H, br s).

In the similar procedure, 4-tert-butoxy-carbonylamino-3-oxo-2-azaspiro[4,4]nonane (compound 83) ¹H-NMR (CDCl₃) δppm: 1.45 (9H, s), 1.2-1.8 (8H, m), 3.13 (2H, s), 4.35 (1H, d, J=7.9 Hz), 5.15 (1H, d, J=7.9 Hz), 7.21 (1H, br s)) and 4-tert-butoxycarbonylamino-3-oxo-2-azaspiro[4,5]decane (compound 84) ¹H-NMR (CDCl₃) δppm: 1.46 (9H, s), 1.0-1.8 (10H, m), 2.9-3.4 (2H, m), 4.15 (1H, d, J=8.6 Hz), 4.89 (1H, d, J=8.6 Hz), 6.71 (1H, br s)) were obtained.

6) 6-tert-Butoxycarbonyl-8-tert-butoxycarbonylamino-6-azaspiro[3,4]octane (compound 87)

15 ml of trifluoroacetic acid was added to 560 mg of ice-cooled compound 82, while stirring. The mixture was then stirred at room temperature for 1.5 hours. Trifluoroacetic acid was removed under reduced pressure and the residue was dissolved in 30 ml of anhydrous tetrahydrofuran. The solution was cooled by ice and 884 mg of lithium aluminum hydride was added to the mixture. The mixture was refluxed for 16 hours. The mixture was cooled by ice then water was added with stirring. An insoluble material was removed by filtration and washed with tetrahydrofuran. The filtrate and washings were combined and to this was added 1.02 g of di-tert-butyl dicarbonate. The mixture was stirred at room temperature for 16 hours. The solvent was removed under reduced pressure. The residue was purified by silica gel column chromatography (50 g) eluting with a mixture of ethyl acetate and n-hexane (1:10) to yield 273 mg of title compound 87.

¹H-NMR (CDCl₃) δppm: 1.45 (18H, s), 1.7-2.1 (6H, m). 3.0-3.6 (4H, m), 3.8-4.2 (1H, m), 5.1 (1H, br d).

In the similar procedure, 2-tert-butoxycarbonyl-4-tert-butoxycarbonylamino-2-azaspiro[4,4]nonane (compound 90) (¹H-NMR (CDCl₃) δppm: 1.45 (18H, s), 1.3-1.8 (8H, m), 3.0-3.3 (3H, m), 3.4-3.7 (1H, m), 3.7-4.1 (1H, m), 4.55 (1H, br d)) and 2-tert-butoxycarbonyl-4-tert-butoxycarbonylamino-2-azaspiro[4,5]decane (compound 93) (¹H-NMR (CDCl₃) δppm: 1.0-1.9 (28H, m), 2.9-4.1 (5H, m), 4.51 (1H, br d)) were obtained.

EXAMPLE 19

7-(8-Amino-6-azaspiro[3,4]octan-6-yl)-1-cyclopropyl-6,8-difluoro-4-oxo-1,4-dihydroquinoline-3-carboxylic acid (compound 94)

2.7 ml of trifluoroacetic acid was added to 173 mg of ice-cooled compound 87 with stirring. Trifluoroacetic acid was removed under reduced pressure. The residue was dissolved in 10 ml of acetonitrile and 100 mg of 1-cyclopropyl-6,7,8-trifluoro-4-oxo-1,4-dihydroquinoline-3-carboxylic acid and 0.98 ml of triethylamine were added to the solution. The mixture was refluxed for 16 hours. The solvent was removed under reduced pressure. Diethyl ether was added to the residue. On cooling, a precipitate was formed. The precipitate was collected by filtration and recrystallized from ethanol and ammonia water to yield 125 mg of title compound 94. m.p.: 260°-263° C.

Elemental analysis, for $C_{20}H_{21}N_3O_3F_2$. Calcd.: C; 58.19, H; 5.76, N; 10.18. Found: C; 58.10, H; 5.38, N; 10.13.

¹H-NMR (0.1N NaOD-D₂O) δppm: 1.05 (2H, br s), 1.13-1.20 (2H, m), 1.85-2.01 (6H, m), 2.15-2.22 (1H, m), 3.25-3.95 (6H, m), 7.56 (1H, d, J=15 Hz), 8.41 (1H, s).

In the similar procedure, 7-(4-amino-2-azaspiro[4,4-]nonan-2-yl)-1-cyclopropyl-6,8-difluoro-4-oxo-1,4-dihydroquinoline-3-carboxylic acid (compound 95) and 7-(4-amino-2-azaspiro[4,5]decan-2-yl)-1-cyclopropyl-6,8-difluoro-4-oxo-1,4-dihydroquinoline-3-carboxylic acid (compound 96) were obtained.

7-(4-Amino-2-azaspiro[4,4]nonan-2-yl)-1-cyclopropyl-6,8-difluoro-4-oxo-1,4-dihydroquinoline-3-carboxylic acid 95:

m.p.: 249°–253° C.

Elemental analysis, for $C_{21}H_{23}N_3O_3F_2.0.7H_2O$: Calcd.: C; 60.63, H; 5.91, N; 10.10. Found: C; 60.63, C; 5.69, N; 9.94.

$^1$H-NMR (0.1N NaOD-D$_2$O) δppm: 1.00 (2H, br s), 1.11–1.15 (2H, m), 1.4–1.7 (8H, m), 3.1–3.9 (6H, m), 7.49 (1H, d, J=13.5 Hz), 8.38 (1H, s).

7-(4-Amino-2-azaspiro[4,5]decan-2-yl)-1-cyclopropyl-6,8-difluoro-4-oxo-1,4-dihydroquinoline-3-carboxylic acid 96:

m.p. 247°–274° C.

Elemental analysis, for $C_{22}H_{25}N_3O_3F_2$: Calcd.: C; 63.30, H; 6.04, N; 10.07. Found: C; 63.14, H; 6.08, N; 10.02.

$^1$H-NMR (0.1N NaOD-D$_2$O) δppm: 1.00 (2H, br s), 1.10–1.16 (2H, m), 1.20–1.63 (10H, m), 2.99–3.90 (6H, m), 7.50 (1H, d, J=14.5 Hz), 8.38 (1H, s).

EXAMPLE 20

10-(8-Amino-6-azaspiro[3,4]octan-6-yl)-9-fluoro-2,3-dihydro-3-(S)-methyl-7-oxo-7H-pyrido[1,2,3-de][1,4-]benzoxazine-6-carboxylic acid (compound 98)

A mixture of 120 mg of compound 87 in 2 ml of trifluoroacetic acid was stirred at room temperature for 2 hours, then trifluoroacetic acid was removed under reduced pressure. To the residue were added 85 mg of 9,10-difluoro-2,3-dihydro-3-(S)-methyl-7-oxo-7H-pyrido[1,2,3-de][1,4]benzoxazine-6-carboxylic acid BF$_2$-chelate, 15 ml of dimethyl sulfoxide and 1 ml of triethylamine. The mixture was stirred at room temperature overnight. The solvent was removed under reduced pressure. 20 ml of 95% methanol and 1.2 ml of triethylamine were added to the residue and the mixture was refluxed for 5 hours. The solvent was removed under reduced pressure and diethyl ether was added to the residue. The resulting crystalline product was collected by filtration and recrystallized from ammonia water and ethanol to yield 50 mg of title compound 98.

m.p.: 229°–231° C.

Elemental analysis, for $C_{20}H_{22}N_2O_4F.\frac{1}{2}H_2O$: Calcd.: C; 57.96, H; 6.08, N; 10.14. Found: C; 57.66, H; 5.84, N; 10.24.

$^1$H-NMR (0.1N NaOH-D$_2$O) δppm: 1.28 (3H, s), 1.60–1.82 (5H, m), 1.95–2.04 (1H, m), 2.95–3.02 (1H, m), 3.08–3.17 (1H, m), 3.34–3.46 (1H, m), 3.58–3.70 (2H, m), 4.00–4.08 (1H, m), 4.18–4.24 (1H, m), 4.29–4.36 (1H, m), 7.18 (1H, d, J=19.5 Hz), 8.13 (1H, s).

REFERENCE EXAMPLE 17

1) tert-Butyl 7-oxo-6-azaspiro[3,4]octane-8-carboxylate (compound 99)

2 g of compound 79 was dissolved in 30 ml of tert-butanol under heating with stirring. 2.8 ml of diphenyl phosphorylazide and 1.97 ml of triethylamine were added to the solution and the mixture was refluxed for 16 hours. The solvent was removed under reduced pressure. The residue was extracted with ethyl acetate and the extract was washed with a saturated sodium bicarbonate aqueous solution, a saturated sodium chloride aqueous solution, 10% citric acid aqueous solution and a saturated sodium chloride aqueous solution. The washings were extracted with ethyl acetate and the extracts were washed as in the same way. The organic layer was dried over anhydrous sodium sulfate and the solvent was removed under reduced pressure. The residue was purified by silica gel column chromatography (75 g) eluting with chloroform containing 0–2% methanol to yield 1.97 g of title compound 99.

$^1$H-NMR (CDCl$_3$) δppm: 1.46 (9H, s), 1.7–2.4 (6H, m), 3.09 (1H, s), 3.41 (1H, d, J=10 Hz), 3.62 (1H, d, J=10 Hz), 6.90 (1H, br).

In the similar procedure, tert-butyl 3-oxo-2-azaspiro[4,4]nonane-4-carboxylate (compound 100) ($^1$H-NMR (CDCl$_3$) δppm: 1.47 (9H, s), 1.70 (8H, br s), 2.98 (1H, s), 3.10 (1H, d, J=9.7 Hz), 3.43 (1H, d, J=9.7 Hz), 7.50 (1H, br s) and tert-butyl 3-oxo-2-azaspiro[4,5]decane-4-carboxylate (compound 101) ($^1$H-NMR (CDCl$_3$) δppm: 1.45 (19H, br s), 2.93 (1H, s), 3.13 (1H, d, J=11Hz), 3.32 (1H, d, J=11 Hz), 6.90 (1H, br s) were obtained.

2) 6-tert-Butoxycarbonyl-8-hydroxymethyl-6-azaspiro[3,4]octane (compound 103)

20 ml of ice-cooled trifluoroacetic acid was added to 1.94 g of ice-cooled compound 99 with stirring. The mixture was stirred at room temperature for 1 hour and trifluoroacetic acid was removed under reduced pressure. The residue was dissolved in 100 ml of anhydrous tetrahydrofuran and the solution was cooled on an ice-bath. 3.11 g of lithium aluminum hydride was slowly added to the solution and the mixture was refluxed for 18 hours. The mixture was cooled by ice and 10 ml of water was slowly added to the solution. The mixture was stirred at room temperature for 30 minutes. An insoluble material was removed by filtration and washed with tetrahydrofuran. The combined filtrate and washings were condensed under reduced pressure to a volume of about 50 ml. To the solution was added di-tert-butyl dicarbonate and the mixture was stirred at room temperature for 18 hours. The solvent was removed under reduced pressure. The residue was purified by silica gel column chromatography (150 g) eluting with a mixture of n-hexane and ethyl acetate (3:2) to yield 420 mg of title compound 103.

$^1$H-NMR (CDCl$_3$) δppm: 1.46 (9H, s), 1.7–2.3 (8H, m), 3.2–3.9 (5H, m).

In the similar procedure, 2-tert-butoxycarbonyl-4-hydroxymethyl-2-azaspiro[4,4]nonane (compound 105) $^1$H-NMR (CDCl$_3$) δppm: 1.46 (9H, s), 1.61 (8H, s), 3.0–3.9 (7H, m)) and 2-tert-butoxycarbonyl-4-hydroxymethyl-2-azaspiro[4,5]decane (compound 107) ($^1$H-NMR (CDCl$_3$) δppm: 1.46 (9H, s), 1.1–1.7 (10H, m), 3.0–3.8 (5H, m)) were obtained.

EXAMPLE 21

1-Cyclopropyl-6,8-difluoro-7-(8-hydroxymethyl-6-azaspiro[3,4]octan-6-yl)-4-oxo-1,4-dihydroquinoline-3-carboxylic acid (compound 108)

Ice-cooled 2.7 ml of trifluoroacetic acid was added to 120 mg of ice-cooled compound 103 dropwise with stirring. The mixture was stirred at room temperature for 1 hour. Trifluoroacetic acid was removed under reduced pressure. The residue was dissolved in 10 ml of acetonitrile and 100 mg of 1-cyclopropyl-6,7,8-trifluoro-4-oxo-1,4-dihydroquinoline-3-carboxylic acid and 0.22 ml of triethylamine were added to the solution. The mixture was then refluxed for 18 hours. The solvent was removed under reduced pressure and to the residue were added concentrated hydrochloric acid and chloroform. The mixture was shaken and the aqueous layer was separated. The aqueous layer was washed with chloroform and the chloroform washings were extracted with a small amount of concentrated hydrochloric acid. The combined aqueous layer was cooled by ice and the pH was adjusted to above 13 with sodium hydroxide. The aqueous layer was washed with chloroform. Then, the aqueous layer was adjusted to pH 7.4 with concentrated hydrochloric acid and a saturated sodium bicarbonate solution. The aqueous layer was extracted with chloroform and the extract was dried over anhydrous sodium sulfate. The solvent was removed under reduced pressure. The residue was recrystallized from ethanol and ammonia water to yield 52 mg of title compound 108 as yellow needles.

m.p.: 273°–274° C.

Elemental analysis, for $C_{21}H_{22}N_2O_4F_2$: Calcd.: C; 62,37, H; 5.48, N; 6.93. Found: C; 62.31, H; 5.39, N; 6.96.

$^1$H-NMR (CDCl$_3$) δppm: 1.11–1.31 (4H, m), 1.89–2.31 (7H, m), 3.63–3.99 (7H, m), 7.75 (1H, dd, J=13.5 & 1.6 Hz), 8.62 (1H, s).

In the similar procedure, 1-cyclopropyl-6,8-difluoro-7-(4-hydroxymethyl-2-azaspiro[4,4]nonan-2-yl)-4-oxo-1,4-dihydroquinoline-3-carboxylic acid (compound 109) and 1-cyclopropyl-6,8-difluoro-7-(4-hydroxymethyl-2-azaspiro[4,5]decan-2-yl)-4-oxo-1,4-dihydroquinoline-3-carboxylic acid (compound 110) were obtained. 1-Cyclopropyl-6,8-difluoro-7-(4-hydroxymethyl-2-azaspiro[4,4]nonan-2-yl)-4-oxo-1,4-dihydroquinoline-3-carboxylic acid (compound 109):

m.p.: 249°–252° C.

Elemental analysis, for $C_{22}H_{24}N_2O_4F_2$: Calcd.: C 63.15, H 5.78, N 6.70. Found: C 62.74, H 5.76, N 6.46.

$^1$H-NMR (CDCl$_3$) δppm: 1.11–1.31 (4H, m), 1.50–1.77 (8H, m), 2.18–2.22 (1H, m), 3.47–4.03 (7H, m), 7.73 (1H, dd, J=13.5 & 1.6 Hz), 8.60 (1H, s).

1-Cyclopropyl-6,8-difluoro-7-(4-hydroxymethyl-2-azaspiro[4,5]decan-2-yl)-4-oxo-1,4-dihydroquinoline-3-carboxylic acid (compound 110):

m.p.: 231°–234° C. Calcd.: C 62.58, H 6.17, N 6.35. Found: C 62.92, H 6.17, N 6.25.

$^1$H-NMR (CDCl$_3$) δppm: 1.13–1.18 (2H, m), 1.24–1.28 (2H, m), 1.30–1 69 (11H, m), 3.51–4.02 (7H, m), 7.80 (1H, dd, J=13.5 & 1.6 Hz), 8.70 (1H, s).

REFERENCE EXAMPLE 18

Synthesis of 7-acetoxy-5-azaspiro[2,4]heptane (compound 69)

A suspension of 1.5 g of compound 12 and 500 mg of lithium aluminum hydride in 30 ml of tetrahydrofuran was refluxed for 16 hours. 0.5 ml of water, 0.5 ml of 15% aqueous sodium hydroxide and 1.5 ml of water were added to the mixture in the mentioned order, and the mixture was stirred at room temperature for 30 minutes. The insoluble material was removed by filtration and the filtrate was concentrated to dryness to yield 1.4 g of 7-hydroxy-5-[1-(R)-phenylethyl]-5-azaspiro[2,4]heptane as a pale yellow oil. 5 ml of acetic anhydride and 5 ml of pyridine were added to 1.4 g of 7-hydroxy-5-[1-(R)-phenylethyl]-5-azaspiro[2,4]heptane which was cooled on an ice-bath. The mixture was stirred at room temperature for 3 hours. Ethyl acetate was added thereto and the solution was washed with saturated aqueous sodium bicarbonate and water, then, dried over anhydrous sodium sulfate. The solvent was removed under reduced pressure to yield 1.6 g of 7-acetoxy-5-[1-(R)-phenylethyl]-5-azaspiro[2,4]heptane as a yellow oil. A mixture of 1.6 g of 7-acetoxy-5-[1-(R)-phenylethyl]-5-azaspiro[2,4]heptane and 1.2 g of palladium-on-carbon (50% water wet) in 20 ml of ethanol was shaken under 3.8 atm of pressured hydrogen atmosphere for 5 hours. During the reduction reaction, the reaction vessel was warmed by a tungsten lamp. The catalyst was removed by filtration and the solvent was removed under reduced pressure to give 880 mg of title compound 69 as an oil.

In addition to the foregoing compounds, the following compounds were synthesized. The physical data of the respective compounds are also indicated.

1: (−)-7-[7-(S)-amino-5-azaspiro[2,3]heptan-5-yl)-1-cyclopropyl-6-fluoro-1,4-dihydro-4-oxoquinoline-3-carboxylic acid 33b, melting point: 259°–261° C.

2: (−)-7-[7-(S)-amino-5-azaspiro[2,3]heptan-5-yl)-6-fluoro-1-(2,4-difluorophenyl)-1,4-dihydro-4-oxo-1,8-naphthyridine-3-carboxylate 111b, melting point: 232°–235° C., [α]$_D$ −20.54° (c=0.73, CHCl$_3$)

TABLE

| Antibacterial Activity (MIC, μg/ml) | | | | | | |
|---|---|---|---|---|---|---|
| bacteria/compound | 31 | 31a | 31b | 32 | 32a | 32b |
| E. coli, NIHJ | ≦0.05 | ≦0.05 | ≦0.05 | ≦0.05 | ≦0.05 | ≦0.05 |
| S. flexneri, 2A 5503 | ≦0.05 | ≦0.05 | ≦0.05 | ≦0.05 | ≦0.05 | ≦0.05 |
| Pr. vulgaris, 08601 | ≦0.05 | ≦0.05 | ≦0.05 | ≦0.05 | ≦0.05 | ≦0.05 |
| Pr. mirabillis, IFO-3849 | ≦0.05 | 0.10 | ≦0.05 | ≦0.05 | 0.10 | ≦0.05 |
| Ser. marcescens, 10100 | ≦0.05 | ≦0.05 | ≦0.05 | ≦0.05 | 0.10 | ≦0.05 |
| Ps. aeruginosa, 32104 | 0.10 | 0.20 | ≦0.05 | 0.10 | 0.39 | 0.10 |
| Ps. aeruginosa, 32121 | ≦0.05 | 0.10 | ≦0.05 | ≦0.05 | 0.10 | ≦0.05 |
| Ps. maltophilia, IID-1275 | ≦0.05 | 0.10 | ≦0.05 | ≦0.05 | 0.10 | ≦0.05 |
| S. aureus, 209P | ≦0.05 | 0.10 | ≦0.05 | ≦0.05 | 0.10 | ≦0.05 |
| S. epidermidis, 56500 | 0.10 | 0.39 | ≦0.05 | 0.10 | 0.20 | ≦0.05 |
| Str. pyogenes, G-36 | 0.39 | 1.57 | 0.10 | 0.10 | 0.78 | 0.39 |
| Str. faecalis, ATCC-19433 | 0.20 | 0.79 | 0.10 | 0.10 | 0.39 | 0.10 |
| bacteria/compound | 33 | 33b | 34 | 35 | 35b | 36 |
| E. coli, NIHJ | ≦0.05 | ≦0.05 | ≦0.05 | ≦0.05 | ≦0.05 | ≦0.05 |
| S. flexneri, 2A 5503 | ≦0.05 | ≦0.05 | ≦0.05 | ≦0.05 | ≦0.05 | ≦0.05 |
| Pr. vulgaris, 08601 | ≦0.05 | ≦0.05 | 0.20 | ≦0.05 | ≦0.05 | ≦0.05 |
| Pr. mirabillis, IFO-3849 | ≦0.05 | ≦0.05 | 0.39 | 0.10 | ≦0.05 | 0.10 |
| Ser. marcescens, 10100 | 0.10 | ≦0.05 | 0.39 | ≦0.05 | ≦0.05 | 0.20 |
| Ps. aeruginosa, 32104 | 0.10 | ≦0.05 | 0.39 | 0.10 | ≦0.05 | 0.20 |
| Ps. aeruginosa, 32121 | ≦0.05 | ≦0.05 | 0.20 | ≦0.05 | ≦0.05 | 0.10 |
| Ps. maltophilia, IID-1275 | 0.10 | 0.10 | 0.10 | ≦0.05 | ≦0.05 | 0.39 |

TABLE-continued
Antibacterial Activity (MIC, µg/ml)

| | | | | | | |
|---|---|---|---|---|---|---|
| S. aureus, 209P | ≦0.05 | ≦0.05 | 0.10 | 0.10 | ≦0.05 | 0.10 |
| S. epidermidis, 56500 | 0.20 | 0.10 | 0.20 | 0.20 | 0.10 | 0.20 |
| Str. pyogenes, G-36 | 0.39 | 0.20 | 0.39 | 0.78 | 0.78 | 0.39 |
| Str. faecalis, ATCC-19433 | 0.39 | 0.20 | 0.78 | 0.39 | 0.39 | 0.78 |

| bacteria/compound | 36b | 37 | 39 | 41b | 55b | 94 |
|---|---|---|---|---|---|---|
| E. coli, NIHJ | ≦0.05 | ≦0.05 | ≦0.05 | ≦0.05 | ≦0.05 | ≦0.05 |
| S. flexneri, 2A 5503 | ≦0.05 | ≦0.05 | ≦0.05 | ≦0.05 | ≦0.05 | ≦0.05 |
| Pr. vulgaris, 08601 | ≦0.05 | ≦0.05 | ≦0.05 | 0.10 | ≦0.05 | ≦0.05 |
| Pr. mirabillis, IFO-3849 | 0.10 | ≦0.05 | 0.20 | 0.20 | ≦0.05 | 0.10 |
| Ser. marcescens, 10100 | 0.20 | 0.10 | 0.39 | 0.10 | 0.10 | 0.10 |
| Ps. aeruginosa, 32104 | 0.20 | 0.20 | 1.56 | 0.20 | ≦0.05 | 0.10 |
| Ps. aeruginosa, 32121 | 0.10 | 0.20 | 0.39 | 0.10 | ≦0.05 | 0.39 |
| Ps. maltophilia, IID-1275 | 0.39 | 0.39 | ≦0.05 | 0.10 | ≦0.05 | 0.20 |
| S. aureus, 209P | ≦0.05 | 0.20 | ≦0.05 | ≦0.05 | ≦0.05 | ≦0.05 |
| S. epidermidis, 56500 | 0.10 | 0.39 | ≦0.05 | 0.10 | ≦0.05 | ≦0.05 |
| Str. pyogenes, G-36 | 0.39 | 0.78 | 0.39 | 0.39 | 0.10 | 0.39 |
| Str. faecalis, ATCC-19433 | 0.39 | 0.78 | 0.39 | 0.20 | 0.10 | 0.20 |

| bacteria/compound | 95 | 98 | 108 | 111b | | |
|---|---|---|---|---|---|---|
| E. coli, NIHJ | ≦0.05 | ≦0.05 | 0.20 | ≦0.05 | | |
| S. flexneri, 2A 5503 | ≦0.05 | ≦0.05 | 0.20 | ≦0.05 | | |
| Pr. vulgaris, 08601 | ≦0.05 | ≦0.05 | 0.10 | ≦0.05 | | |
| Pr. mirabillis, IFO-3849 | ≦0.05 | 0.20 | 0.78 | 0.20 | | |
| Ser. marcescens, 10100 | 0.10 | 0.10 | 1.56 | 0.10 | | |
| Ps. aeruginosa, 32104 | 0.39 | 0.39 | 1.56 | 0.20 | | |
| Ps. aeruginosa, 32121 | 0.20 | 0.20 | 0.39 | 0.10 | | |
| Ps. maltophilia, IID-1275 | 0.10 | 0.20 | 1.56 | 0.20 | | |
| S. aureus, 209P | ≦0.05 | ≦0.05 | ≦0.05 | ≦0.05 | | |
| S. epidermidis, 56500 | 0.10 | ≦0.05 | ≦0.05 | 0.10 | | |
| Str. pyogenes, G-36 | 0.20 | 0.39 | 0.39 | 0.20 | | |
| Str. faecalis, ATCC-19433 | 0.20 | 0.20 | 0.20 | 0.39 | | |

REACTION SCHEME

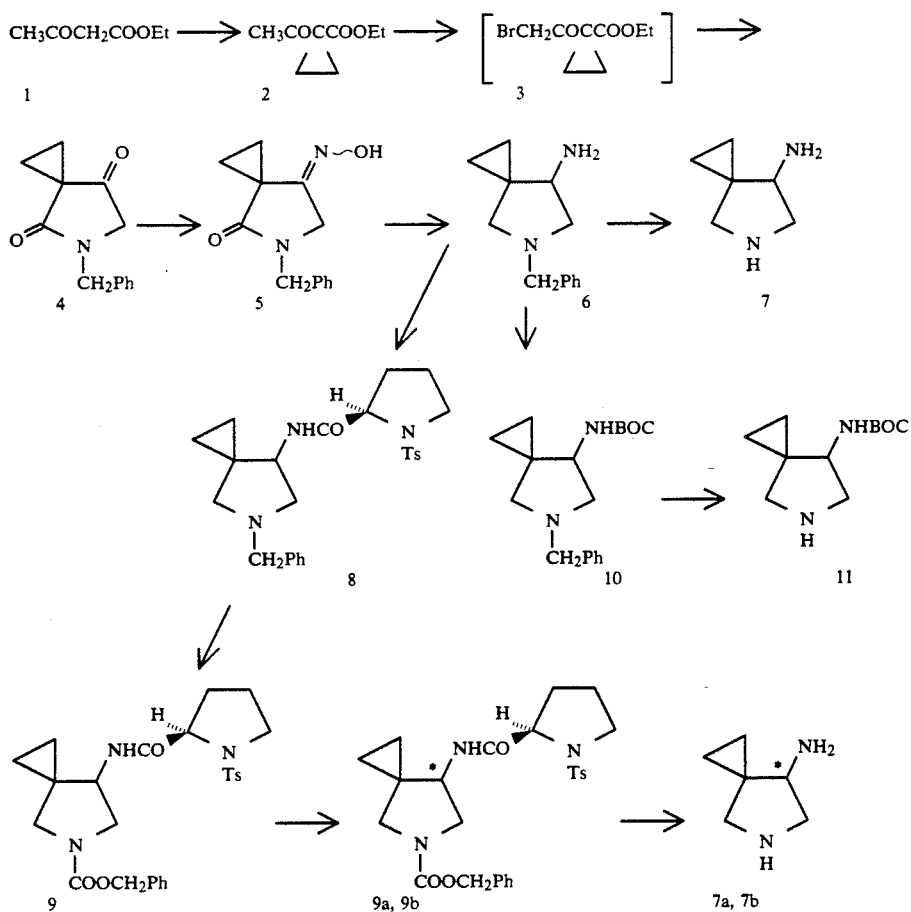

-continued
REACTION SCHEME
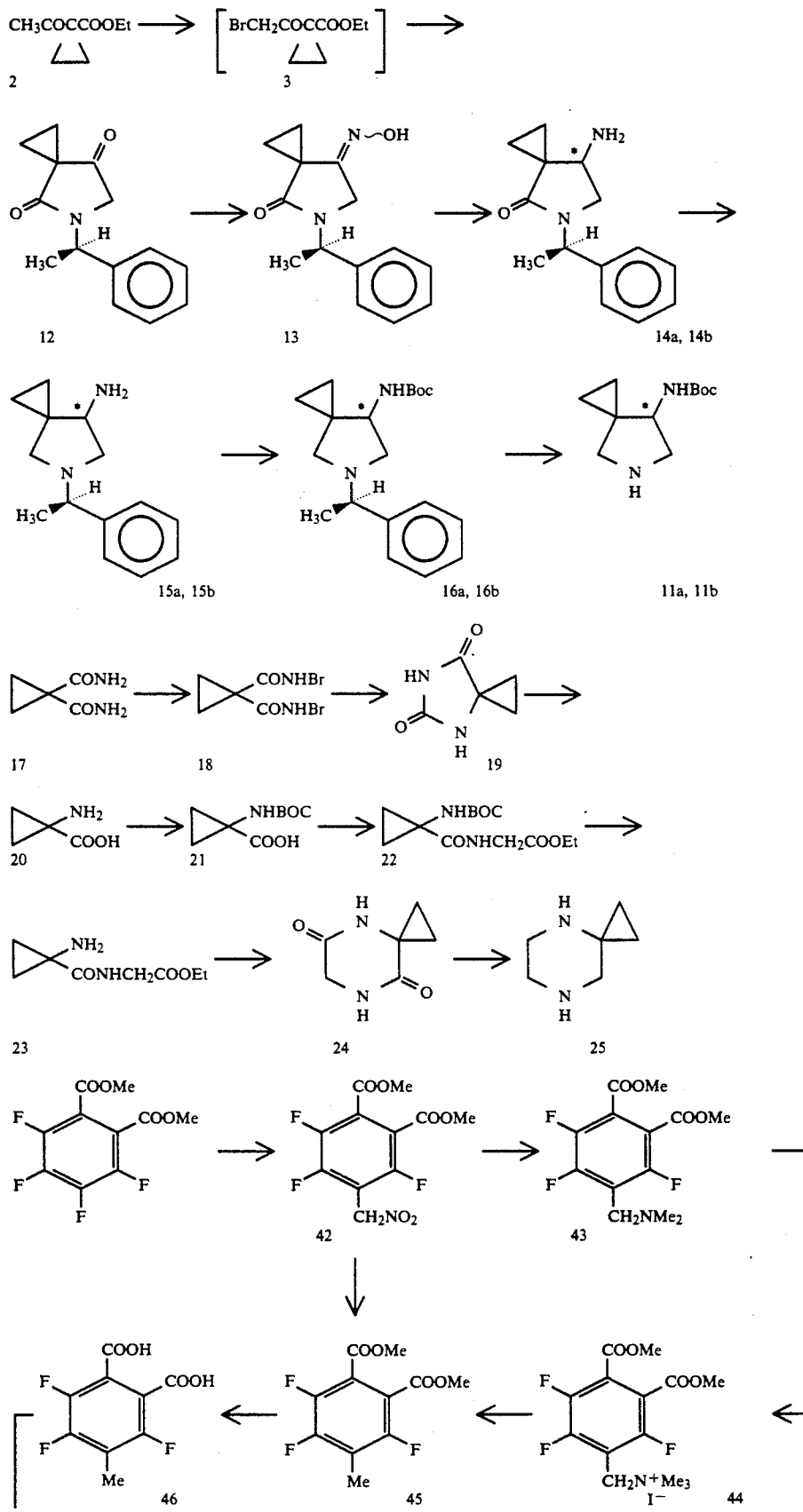

-continued
REACTION SCHEME
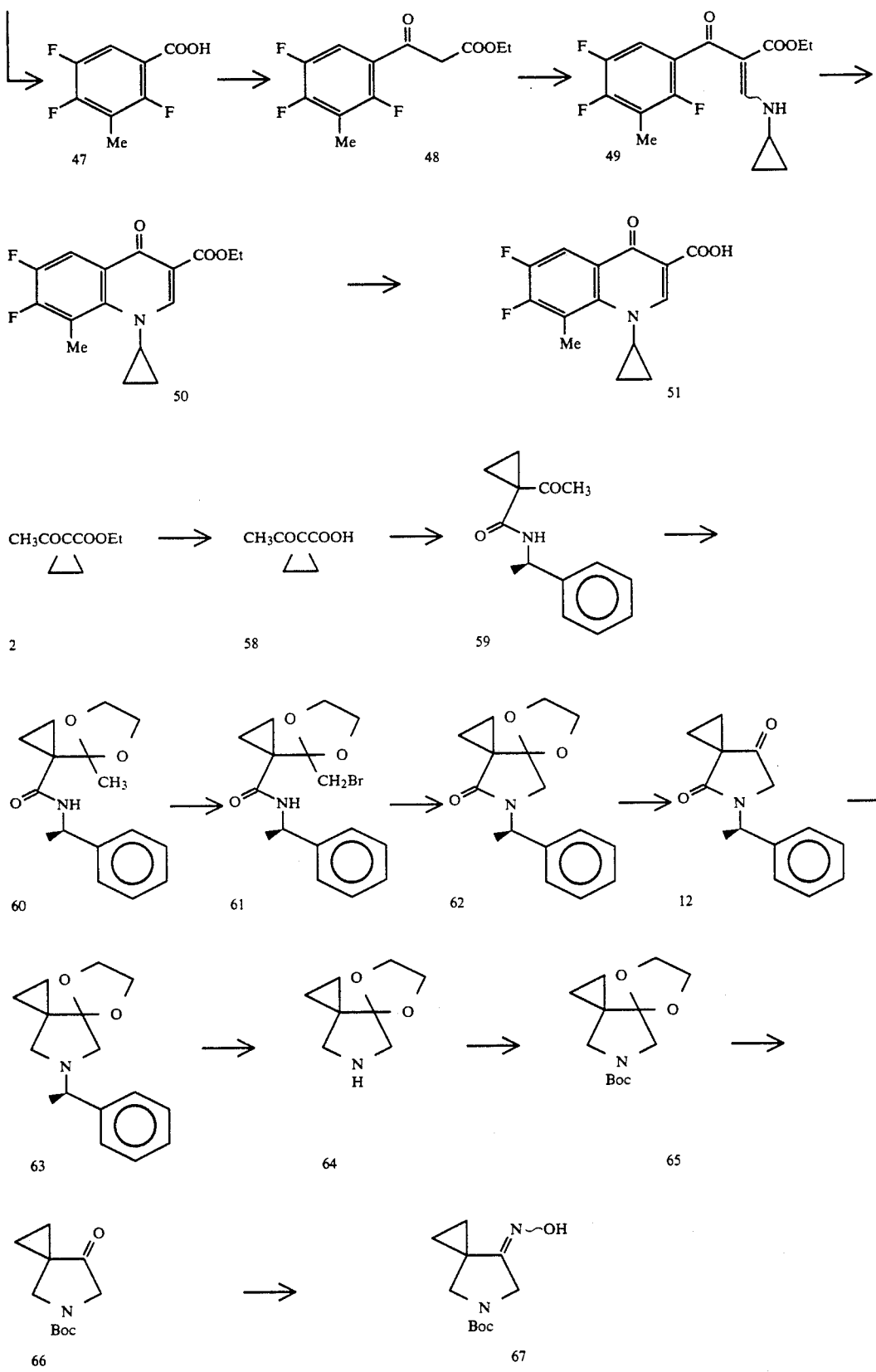

-continued
REACTION SCHEME
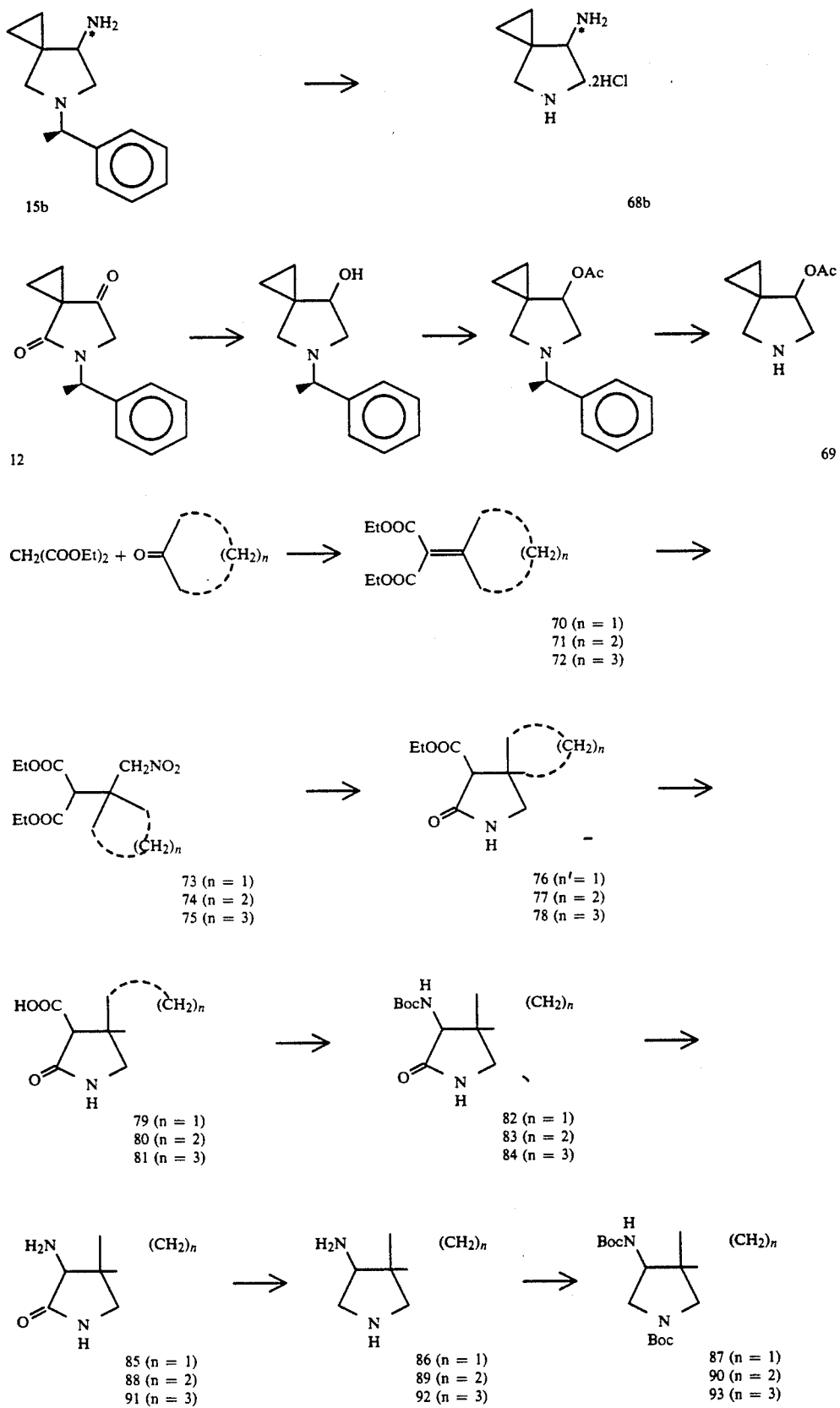

-continued
REACTION SCHEME
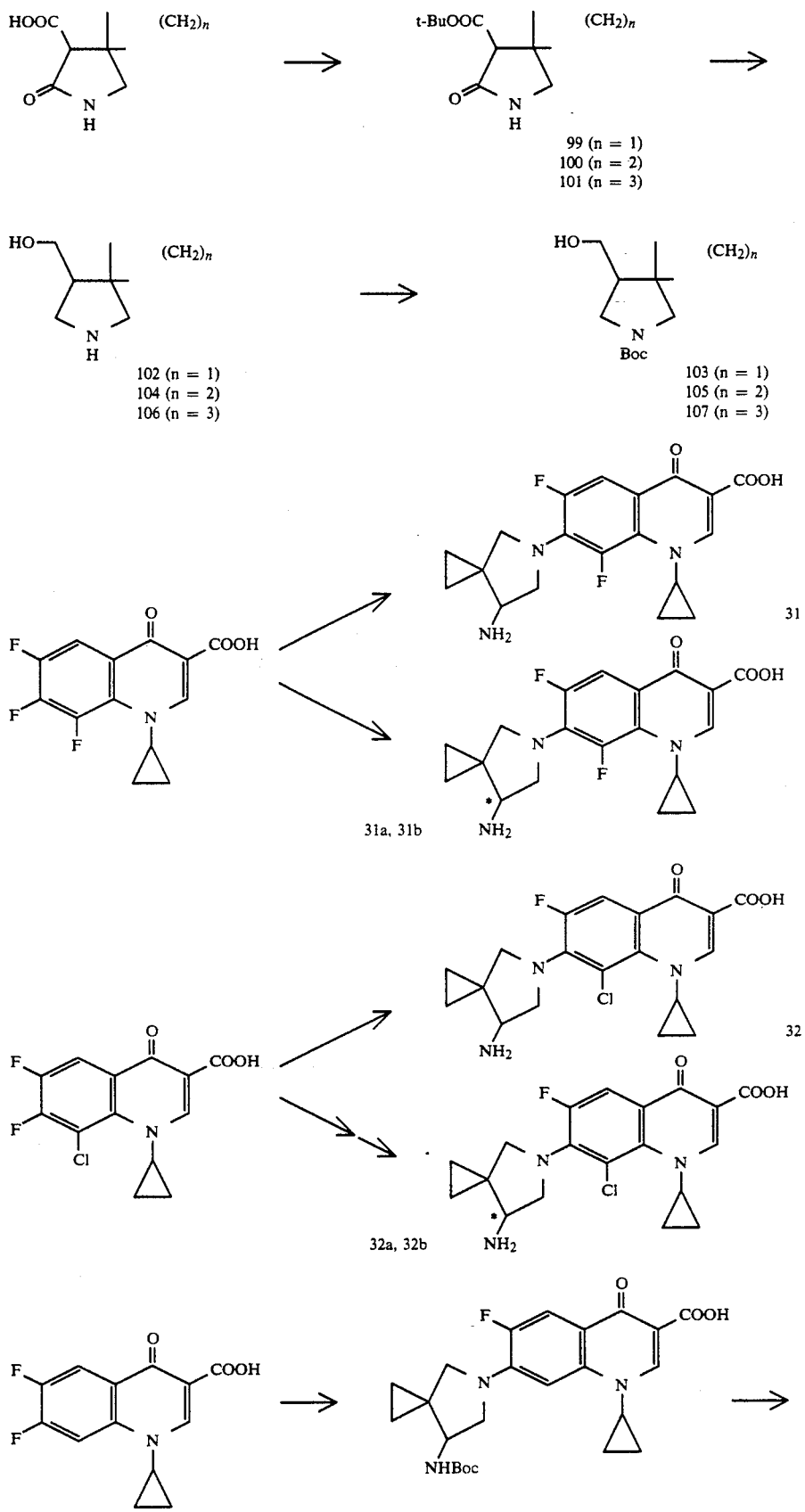

-continued
REACTION SCHEME
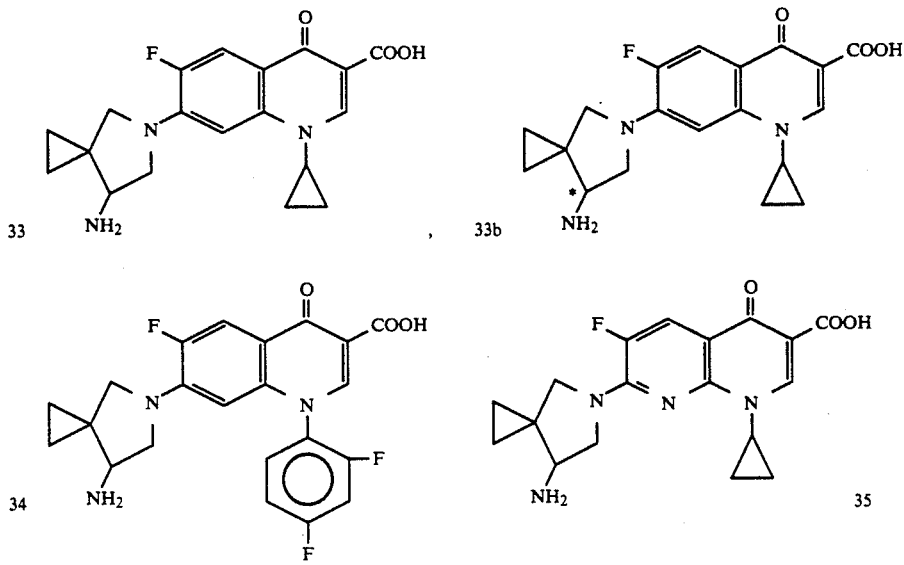
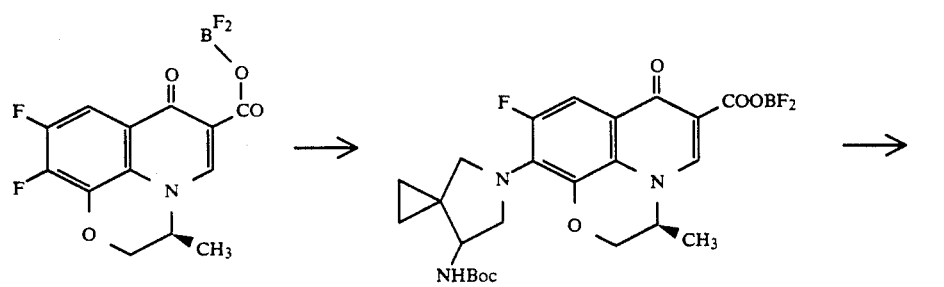
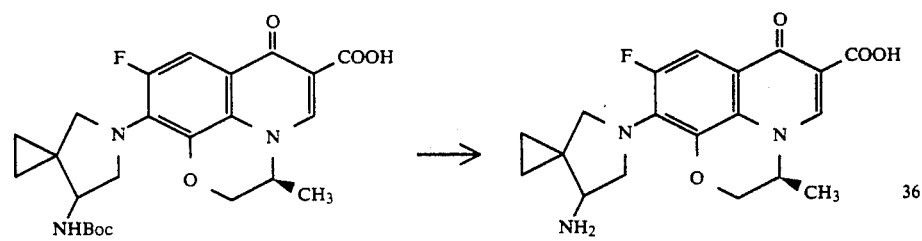
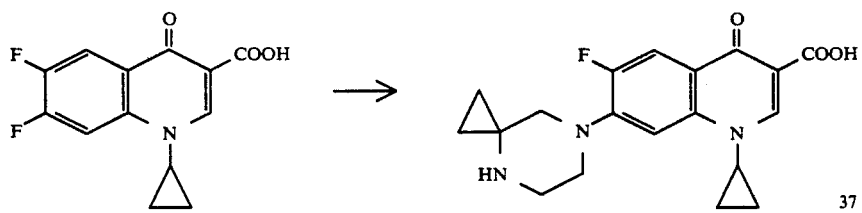
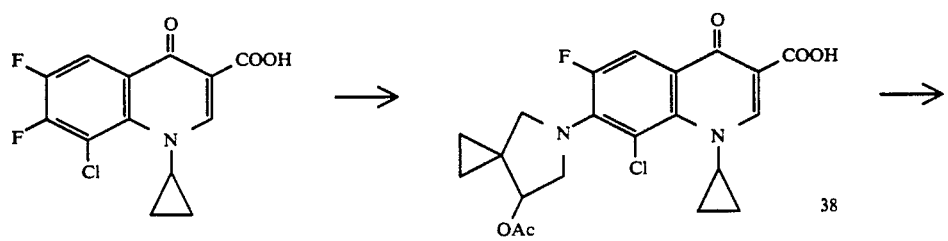

-continued
REACTION SCHEME
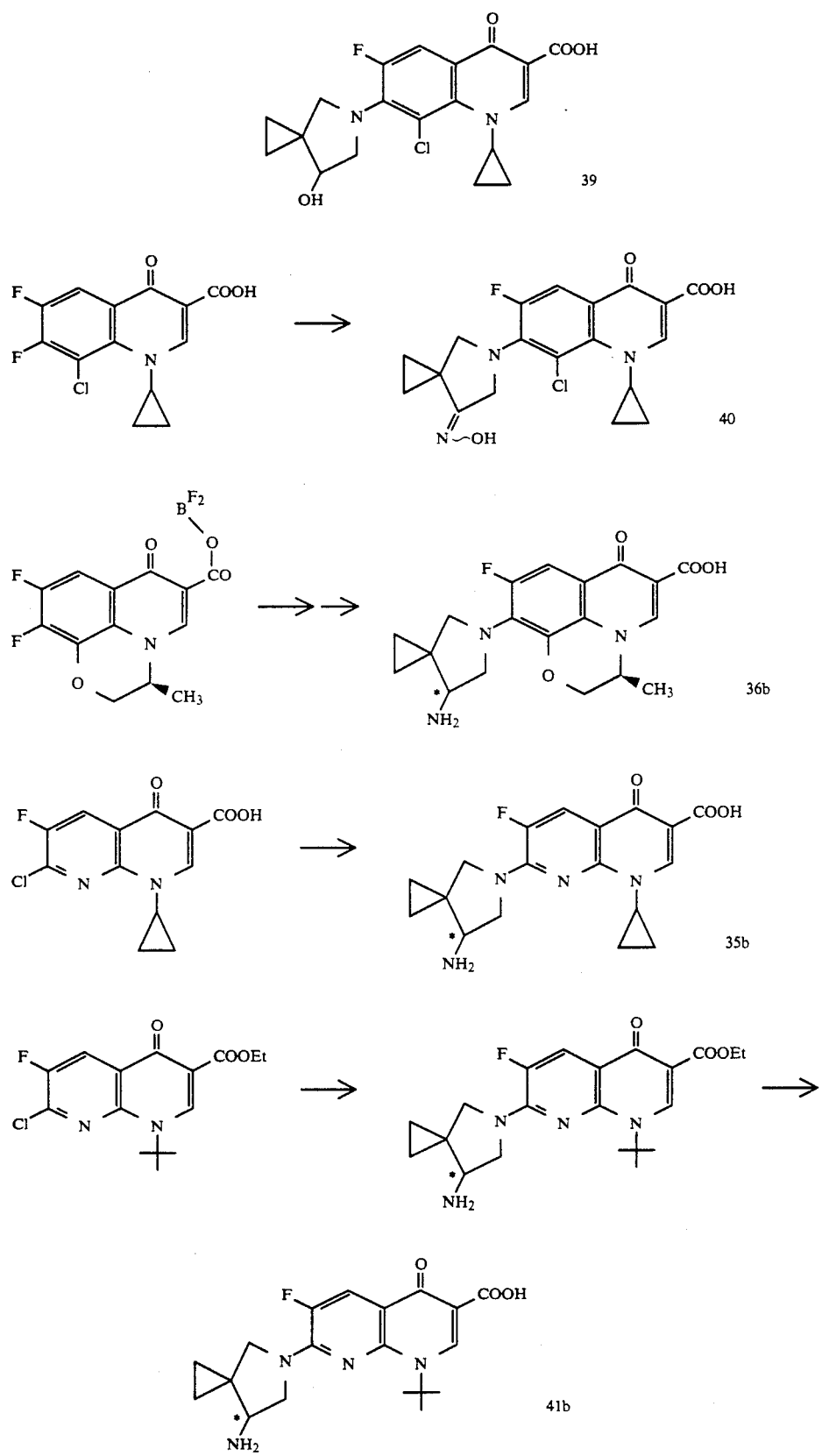

-continued
REACTION SCHEME
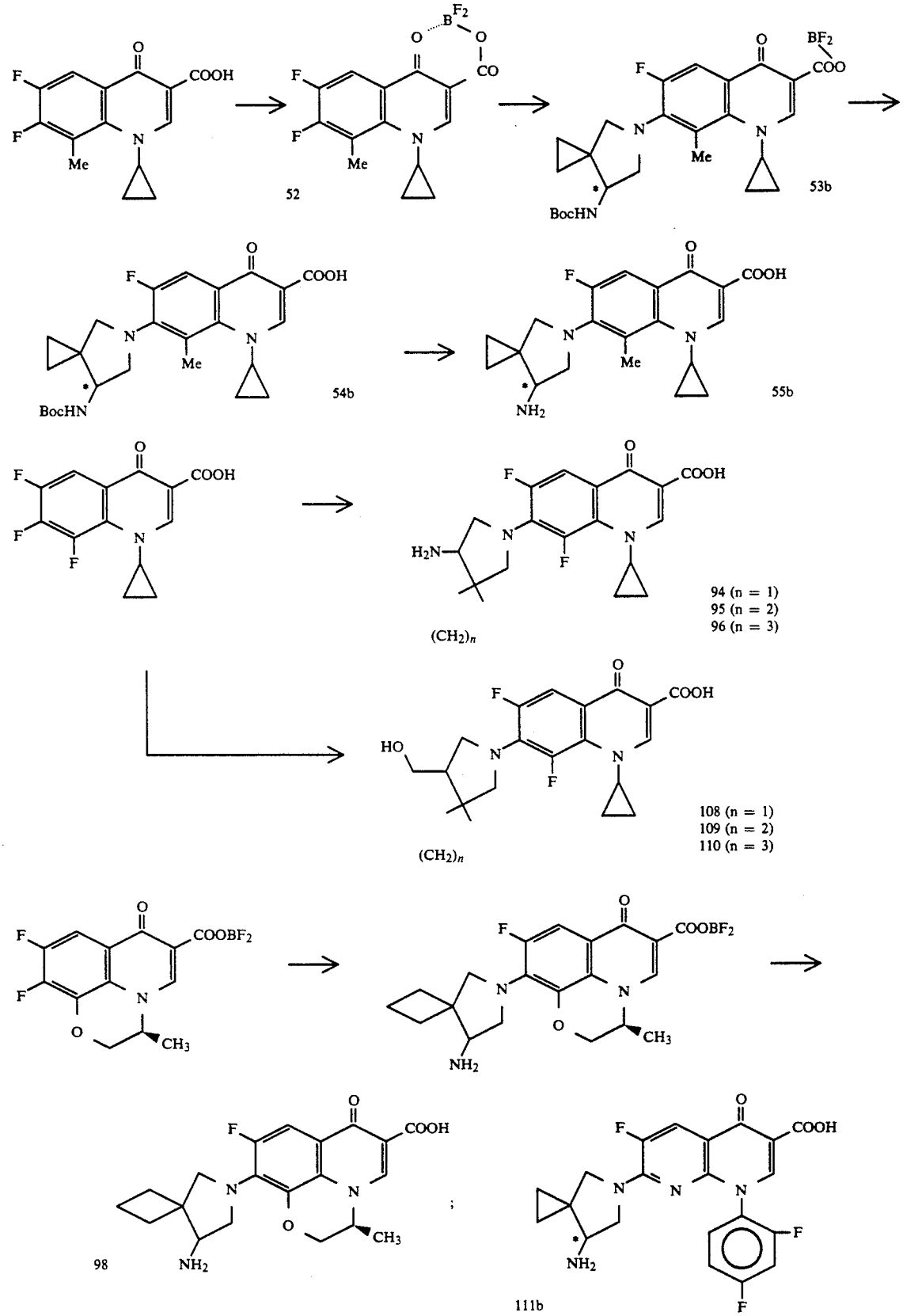
While the invention has been described in detail and with reference to specific embodiments thereof, it will be apparent to one skilled in the art that various changes and modifications can be made therein without departing from the spirit and scope thereof.

What is claimed is:

1. A spiro compound of formula I:

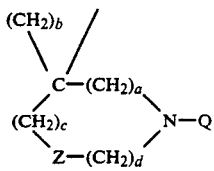

wherein a represents an integer equal to 0 or 1; b represents an integer equal to 2 through 5, inclusive; c represents an integer equal to 0 or 1; and d represents an integer equal to 0 through 2, inclusive; Z represents

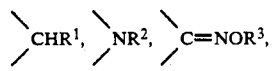

an oxygen atom or a sulfur atom, wherein $R^1$ represents a hydrogen atom, an amino group, a monoalkylamino group of 1 to 6 carbon atoms, a dialkylamino group containing 1 to 6 carbon atoms per alkyl, a hydroxyl group, an alkoxy group of 1 to 6 carbon atoms or a hydroxyalkyl group of 1 to 6 carbon atoms; $R^2$ represents a hydrogen atom, an alkyl group of 1 to 6 carbon atoms, a hydroxyalkyl group of 1 to 6 carbon atoms, a haloalkyl group of 1 to 6 carbon atoms, a formyl group or an alkylcarbonyl group of 2 to 7 carbon atoms; and $R^3$ represents a hydrogen atom or an alkyl group of 1 to 6 carbon atoms; Q represents a partial structure of formula II:

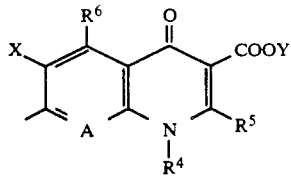

wherein $R^4$ represents an alkyl group of 1 to 6 carbon atoms, an alkenyl group of 2 to 6 carbon atoms, a haloalkyl group of 1 to 6 carbon atoms, a substituted or unsubstituted cycloalkyl group of 3 to 6 carbon atoms, a substituted or unsubstituted aryl group, a 4-pyridyl group or a 2-fluoro-4-pyridyl group, an alkoxy group of 1 to 6 carbon atoms or an alkylamino group of 1 to 6 carbon atoms; $R^5$ represents a hydrogen atom or an alkyl group of 1 to 6 carbon atoms; $R^6$ represents a hydrogen atom, an amino group, a methylamino group, an ethylamino group, an isopropylamino group, a dimethylamino group, a diethylamino group, a hydroxyl group, an alkoxy group of 1 to 6 carbon atoms or a halogen atom; A represents a nitrogen atom or

wherein $R^7$ represents a hydrogen atom, an alkyl group of 1 to 6 carbon atoms, a halogen atom, an alkoxy group of 1 to 6 carbon atoms, a haloalkyl group of 1 to 6 carbon atoms or a cyano group; X represents a halogen atom; Y represents a hydrogen atom, an alkyl group of 1 to 6 carbon atoms, an alkoxyalkyl group of 1 to 6 carbon atoms, a phenylalkyl group containing 1 to 6 carbon atoms in its alkyl moiety, a phenyl group, an acetoxymethyl group, a pivaloyloxymethyl group, an ethoxycarbonyloxy group, a choline group, a dimethylaminoethyl group, a 5-indanyl group, a phthalidinyl group, a 5-substituted-2-oxo-1,3-dioxazol-4-ylmethyl group or a 3-acetoxy-2-oxobutyl group; $R^4$, together with $R^5$, or $R^4$ together with $R^7$ may form a tricyclic ring of the following structure:

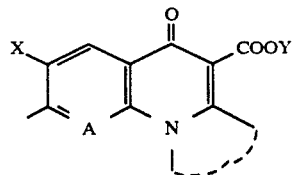

or

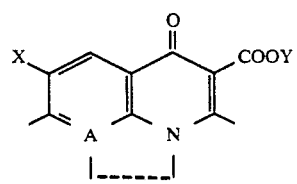

wherein A represents

and X and Y are as earlier defined in this claim; or $R^4$, $R^5$ and $R^7$ may form a tetracyclic ring system of the following formula:

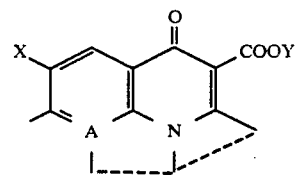

wherein A represents

X and Y are as earlier defined in this claim, and the broken lines represent a monocyclic or bicyclic ring system fused to the quinoline ring, which tricyclic or tetracyclic ring is a 4 to 7 membered substituted or unsubstituted carbon-containing ring having one of the following formulae:

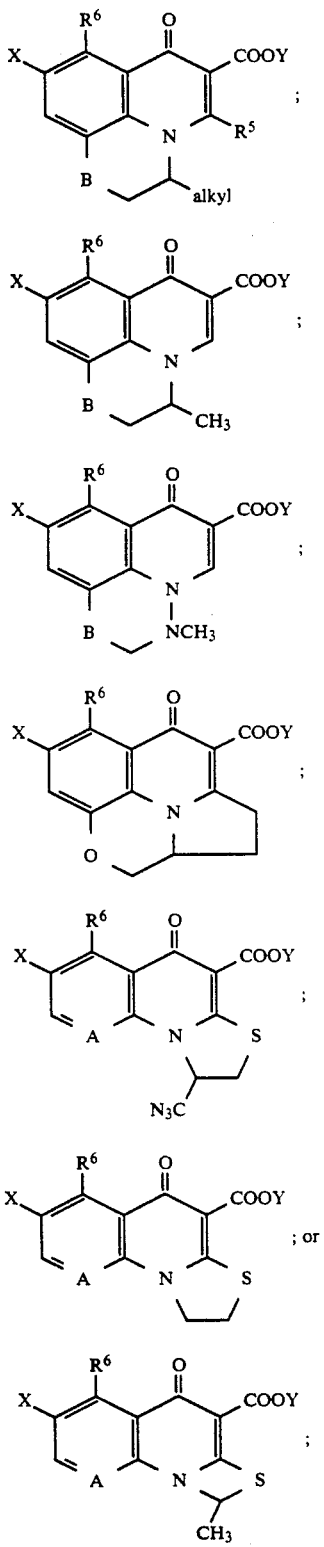

wherein A represents

$R^5$, $R^6$, and X and Y are as earlier defined in this claim; alkyl means an alkyl group of 1 to 6 carbon atoms; and B represents an oxygen atom, sulfur atom or carbonyl group, or a salt thereof.

2. The spiro compound of formula I as claimed in claim 1, wherein a is 1, b is 2, c is 0 and d is 1, and Z represents

or a salt thereof.

3. The spiro compound of formula I as claimed in claim 1, wherein a is 1, b is 3, c is 0, and d is 1, and Z represents

or a salt thereof.

4. The spiro compound of formula I as claimed in claim 1, wherein a is 1, b is 2, c is 0 and d is 2, and Z represents

or a salt thereof.

5. The spiro compound of formula I as claimed in claim 1, wherein said spiro compound is optically pure.

6. A spiro compound selected from the group consisting of 7-(7-amino-5-azaspiro[2.4]heptan-5-yl)-1-cyclopropyl-6,8-difluoro-1,4-dihydro-4-oxoquinoline-3-carboxylic acid, 7-(7-amino-5-azaspiro[2.4]heptan-5-yl)-8-chloro-1-cyclopropyl-6-fluoro-1,4-dihydro-4-oxoquinoline-3-carboxylic acid, 7-(7-amino-5-azaspiro[2.4]heptan-5-yl)-1-cyclopropyl-6-fluoro-1,4-dihydro-4-oxoquinoline-3-carboxylic acid, 7-(7-amino-5-azaspiro[2.4]heptan-5-yl)-6-fluoro-1-(2,4-difluorophenyl)-1,4-dihydro-4-oxoquinoline-3-carboxylic acid, 7-(7-amino-5-azaspiro[2.4]heptan-5-yl)-1-cyclopropyl-6-fluoro-1,4-dihydro-4-oxo-1,8-naphthyridine-3-carboxylic acid, 10-(7-amino-5-azaspiro[2.4]heptan-5-yl)-9-fluoro-2,3-dihydro-3-(S)-methyl-7-oxo-7H-pyrido[1.2.3-de][1.4]benzoxazine-6-carboxylic acid, 1-cyclopropyl-7-(4,7-diazaspiro[2.5]octan-7-yl)-6-fluoro-1,4-dihydro-4-oxoquinoline-3-carboxylic acid, 7-(7-amino-5-azaspiro[2.4]heptan-5-yl)-1-cyclopropyl-6-fluoro-8-methyl-1,4-dihydro-4-oxoquinoline-3-carboxylic acid, 7-(7-hydroxy-5-azaspiro[2.4]heptan-5-yl)-8-chloro-1-cyclopropyl-6-fluoro-1,4-dihydro-4-oxoquinoline-3-carboxylic acid, 7-(7-amino-5-azaspiro[2.4]heptan-5-yl)-1-(2-methyl-2-propyl)-6-fluoro-1,4-dihydro-4-oxo-1,8-naphthyridine-3-carboxylic acid, 7-(7-hydroxyamino-5-azaspiro[2.4]heptan-5-yl)-8-chloro-1-cyclopropyl-6-fluoro-1,4-dihydro-4-oxoquinoline-3-carboxylic acid, 1-cyclopropyl-6,8-difluoro-7-(8-hydroxymethyl-6-azaspiro[3.4]octan-6-yl)-4-oxo-1,4-dihydroquinoline-3-carboxylic acid, 1-cyclopropyl-6,8-difluoro-7-(4-hydroxymethyl-2-azaspiro[4,4]-nonan-2-yl)-4-oxo-1,4-dihydroquinoline-3-carboxylic acid, 1-cyclopropyl-6,8- difluoro-7-(4-hydroxymethyl-2-azaspiro[4.5]decan-2-yl)-4-oxo-1,4-dihydroquinoline-3-carboxylic acid, 7-(8-amino-6 -azaspiro[3.4]octan-6-yl)-1-cyclopropyl-6,8-difluoro-4-oxo-1,4-dihydroquinoline-3-carboxylic acid, 10-(8-amino-6-azaspiro[3.4]octan-6-yl)-9-fluoro-2,3-dihydro-3-(S)-methyl-7-oxo-7H-pyrido-[1.2.3-de][1.4-]benzoxazine-6-carboxylic acid, 7-(4-amino-2-azaspiro[4.4]nonan-2-yl)-1-cyclopropyl-6,8-difluoro-4-oxo-1,4-dihydroquinoline-3-carboxylic acid or a salt thereof.

7. A spiro compound of formula I:

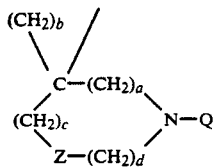

wherein a represents an integer equal to 0 or 1; b represents an integer equal to 2 through 5, inclusive; c represents an integer equal to 0 or 1; and d represents an integer equal to 0 through 2, inclusive; Z represents

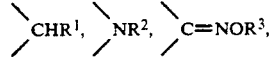

an oxygen atom or a sulfur atom, wherein $R^1$ represents a hydrogen atom, an amino group, a monoalkylamino group of 1 to 6 carbon atoms, a dialkylamino group containing 1 to 6 carbon atoms per alkyl, a hydroxyl group, an alkoxy group of 1 to 6 carbon atoms or a hydroxyalkyl group of 1 to 6 carbon atoms; $R^2$ represents a hydrogen atom, an alkyl group of 1 to 6 carbon atoms, a hydroxyalkyl group of 1 to 6 carbon atoms, a haloalkyl group of 1 to 6 carbon atoms, a formyl group or an alkylcarbonyl group of 2 to 7 carbon atoms; and $R^3$ represents a hydrogen atom or an alkyl group of 1 to 6 carbon atoms; Q represents a partial structure of formula II:

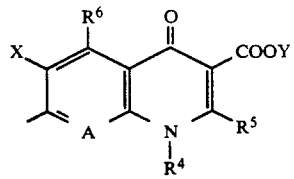

wherein $R^4$ represents an alkyl group of 1 to 6 carbon atoms, an alkenyl group of 2 to 6 carbon atoms, a haloalkyl group of 1 to 6 carbon atoms, a substituted or unsubstituted cycloalkyl group of 3 to 6 carbon atoms, a 4-fluorophenyl group, a 2,4-difluorophenyl group, a 4-pyridyl group or a 2-fluoro-4-pyridyl group, an alkoxy group of 1 to 6 carbon atoms or an alkylamino group of 1 to 6 carbon atoms; $R^5$ represents a hydrogen atom or an alkyl group of 1 to 6 carbon atoms; $R^6$ represents a hydrogen atom, an amino group, a methylamino group, an ethylamino group, an isopropylamino group, a dimethylamino group, a diethylamino group, a hydroxyl group, an alkoxy group of 1 to 6 carbon atoms or a halogen atom; A represents a nitrogen atom or

wherein $R^7$ represents a hydrogen atom, an alkyl group of 1 to 6 carbon atoms, a halogen atom, an alkoxy group of 1 to 6 carbon atoms, a haloalkyl group of 1 to 6 carbon atoms or a cyano group; X represents a halogen atom; Y represents a hydrogen atom, an alkyl group of 1 to 6 carbon atoms, an alkoxyalkyl group of 1 to 6 carbon atoms, a phenylalkyl group containing 1 to 6 carbon atoms in its alkyl moiety, a phenyl group, an acetoxymethyl group, a pivaloyloxymethyl group, an ethoxycarbonyloxy group, a choline group, a dimethylaminoethyl group, a 5-indanyl group, a phthalidinyl group, a 5-substituted-2-oxo-1,3-dioxazol-4-ylmethyl group or a 3-acetoxy-2-oxobutyl group; wherein $R^4$ and $R^5$ or $R^4$ and $R^7$ can form a monocyclic ring or $R^4$, $R^5$, and $R^7$ can form a bicyclic ring, the monocyclic ring or the bicyclic ring having one of the formulae:

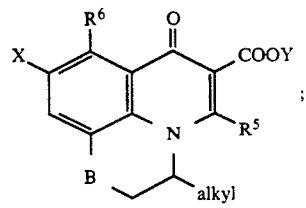

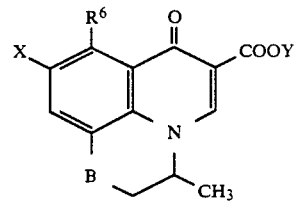

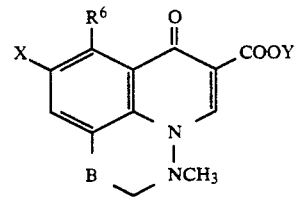

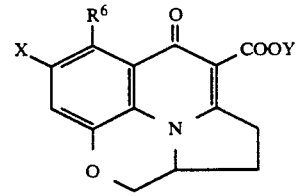

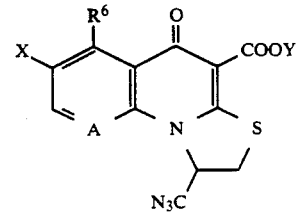

-continued

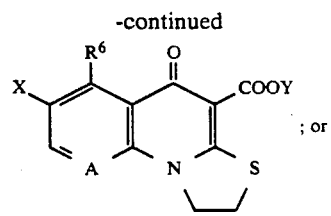
; or

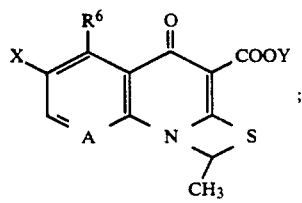
;

wherein A represents

where $R^7$ is as earlier defined in this claim, $R^5$ and $R^6$ are as earlier defined in this claim; alkyl is an alkyl group of 1 to 6 carbon atoms or a haloalkyl group of 1 to 6 carbon atoms; B represents an oxygen atom, sulfur atom or carbonyl group; and X and Y are as earlier defined in this claim, or a salt thereof.

8. A spiro compound of formula I:

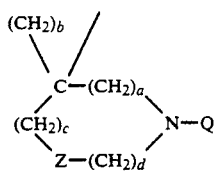

wherein a represents an integer equal to 0 or 1; b represents an integer equal to 2 through 5, inclusive; c represents an integer equal to 0 or 1; and d represents an integer equal to 0 through 2, inclusive; Z represents

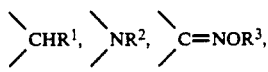

an oxygen atom or a sulfur atom, wherein $R^1$ represents a hydrogen atom, an amino group, a monoalkylamino group of 1 to 6 carbon atoms, a dialkylamino group containing 1 to 6 carbon atoms per alkyl, a hydroxyl group, an alkoxy group of 1 to 6 carbon atoms or a hydroxyalkyl group of 1 to 6 carbon atoms; $R^2$ represents a hydrogen atom, an alkyl group of 1 to 6 carbon atoms, a hydroxyalkyl group of 1 to 6 carbon atoms, a haloalkyl group of 1 to 6 carbon atoms, a formyl group or an alkylcarbonyl group of 2 to 7 carbon atoms; and $R^3$ represents a hydrogen atom or an alkyl group of 1 to 6 carbon atoms; Q represents a partial structure of formula II:

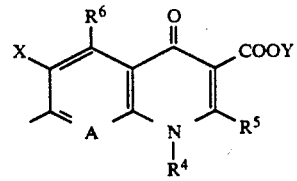

wherein $R^4$ represents an alkyl group of 1 to 6 carbon atoms, an alkenyl group of 2 to 6 carbon atoms, a haloalkyl group of 1 to 6 carbon atoms, a substituted or unsubstituted cycloalkyl group of 3 to 6 carbon atoms, a substituted or unsubstituted aryl group, a 4-pyridyl group or a 2-fluoro-4-pyridyl group, an alkoxy group of 1 to 6 carbon atoms or an alkylamino group of 1 to 6 carbon atoms; $R^5$ represents a hydrogen atom or an alkyl group of 1 to 6 carbon atoms; $R^6$ represents a hydrogen atom, an amino group, a methylamino group, an ethylamino group, an isopropylamino group, a dimethylamino group, a diethylamino group, a hydroxyl group, an alkoxy group of 1 to 6 carbon atoms or a halogen atom; A represents a nitrogen atom or

wherein $R^7$ represents a hydrogen atom, an alkyl group of 1 to 6 carbon atoms, a halogen atom, an alkoxy group of 1 to 6 carbon atoms, a haloalkyl group of 1 to 6 carbon atoms or a cyano group; X represents a halogen atom; Y represents a hydrogen atom, an alkyl group of 1 to 6 carbon atoms, an alkoxyalkyl group of 1 to 6 carbon atoms, a phenylalkyl group containing 1 to 6 carbon atoms in its alkyl moiety, a phenyl group, an acetoxymethyl group, a divaloyloxymethyl group, an ethoxycarbonyloxy group, a choline group, a dimethylaminoethyl group, a 5-indanyl group, a phthalidinyl group, a 5-substituted-2-oxo-1,3-dioxazol-4-ylmethyl group or a 3-acetoxy-2-oxobutyl group; $R^4$, together with $R^5$, or $R^4$ together with $R^7$, forms a tricyclic ring, or $R^4$, taken together with $R^5$ and $R^7$, forms a tetracyclic ring where said tricyclic or tetracyclic ring is one of the following formulae:

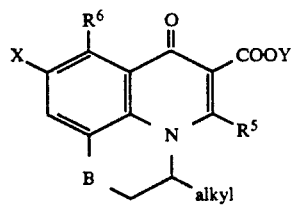
;

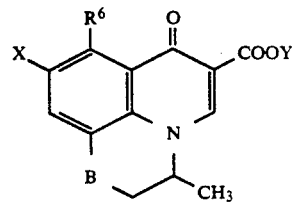
;

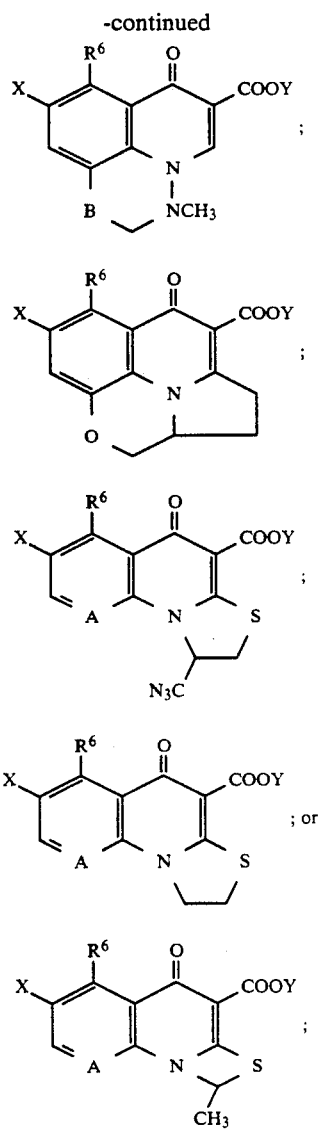

wherein alkyl means an alkyl group of from 1 to 6 carbon atoms; B represents an oxygen atom, sulfur atom or a carbonyl group; and X and Y are as earlier defined in this claim, or a salt thereof.

9. 7-(7-Amino-5-azaspiro[2.4]heptan-5-yl)-1-cyclopropyl-6,8-difluoro-1,4-dihydro-4-oxoquinoline-3-carboxylic acid or a salt thereof.

10. 7-(7-Amino-5-azaspiro[2.4]heptan-5-yl)-8-chloro-1-cyclopropyl-6-fluoro-1,4-dihydro-4-oxoquinoline-3-carboxylic acid or a salt thereof.

11. 7-(7-Amino-5-azaspiro[2.4]heptan-5-yl)-1-cyclopropyl-6-fluoro-1,4-dihydro-4-oxoquinoline-3-carboxylic acid or a salt thereof.

12. 7-(7-Amino-5-azaspiro[2.4]heptan-5-yl)-6-fluoro-1-(2,4-difluorophenyl)-1,4-dihydro-4-oxoquinoline-3-carboxylic acid or a salt thereof.

13. 7-(7-amino-5-azaspiro[2.4]heptan-5-yl)-1-cyclopropyl-6-fluoro-1,4-dihydro-4-oxo-1,8-naphthyridine-3-carboxylic acid or a salt thereof.

14. 7-(7-amino-5-azaspiro[2.4]heptan-5-yl)-1-(2-methyl-2-propyl)-6-fluoro-1,4-dihydro-4-oxo-1,8-naphthyridine-3-carboxylic acid or a salt thereof.

15. 7-(7-amino-5-azaspiro[2.4]heptan-5-yl)-6-fluoro-1-(2,4-difluorophenyl)-1,4-dihydro-4-oxo- 1,8-naphthyridine-3-carboxylic acid or a salt thereof.

16. 7-(7-Amino-5-azaspiro[2.4]heptan-5-yl)-1-cyclopropyl-6-fluoro-8-methyl-1,4-dihydro-4-oxoquinoline-3-carboxylic acid or a salt thereof.

17. 10-(7-amino-5-azaspiro[2.4]heptan-5-yl)-9-fluoro-2,3-dihydro-3-(S)-methyl-7-oxo-7H-pyrido[1.2.3-de][1.4]benzoxazine-6-carboxylic acid or a salt thereof.

18. 10-(8-Amino-6-azaspiro[3.4]octan-6-yl)-9-fluoro-2,3-dihydro-3-(S)-methyl-7-oxo-7H-pyrido-[1.2.3-de][1.4]benzoxazine-6-carboxylic acid or a salt thereof.

19. 7(7-Hydroxy-5-azaspiro[2.4]-heptan-5-yl)-8-chloro-1-cyclopropyl-6-fluoro-1,4-dihydro-4-oxoquinoline-3-carboxylic acid or a salt thereof.

20. 1-cyclopropyl-7-(4,7-diazaspiro-[2.5]octan-7-yl)-6-fluoro-1,4-dihydro-4-oxo-quinoline-3-carboxylic acid or a salt thereof.

21. A compound as set forth in claim 9, wherein said compound is stereoisomerically pure.

22. A compound as set forth in claim 10, wherein said compound is stereoisomerically pure.

23. A compound as set forth in claim 11, wherein said compound is stereoisomerically pure.

24. A compound as set forth in claim 12, wherein said compound is stereoisomerically pure.

25. A compound as set forth in claim 13, wherein said compound is stereoisomerically pure.

26. A compound as set forth in claim 14, wherein said compound is stereoisomerically pure.

27. A compound as set forth in claim 15, wherein said compound is stereoisomerically pure.

28. A compound as set forth in claim 16, wherein said compound is stereoisomerically pure.

29. A compound as set forth in claim 17, wherein said compound is stereoisomerically pure.

30. A compound as set forth in claim 18, wherein said compound is stereoisomerically pure.

31. A pharmaceutical composition comprising:
(A) an antibacterial effective amount of a spiro compound of formula I:

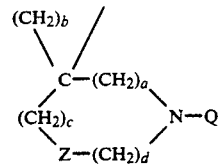

wherein a represents an integer equal to 0 or 1; b represents an integer equal to 2 through 5, inclusive; c represents an integer equal to 0 or 1; and d represents an integer equal to 0 through 2, inclusive; Z represents

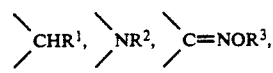

an oxygen atom or a sulfur atom, wherein $R^1$ represents a hydrogen atom, an amino group, a monoalkylamino group of 1 to 6 carbon atoms, a dialkylamino group containing 1 to 6 carbon atoms per alkyl, a hydroxyl group, an alkoxy group of 1 to 6 carbon atoms or a hydroxyalkyl group of 1 to 6 carbon atoms; $R^2$ represents a hydrogen atom, an alkyl group of 1 to 6 carbon atoms, a hydroxyalkyl group of 1 to 6 carbon atoms, a haloalkyl group of 1 to 6 carbon atoms, a formyl group or an alkylcarbonyl group of 2 to 7 carbon atoms; and $R^3$ represents a hydrogen atom or an alkyl group of 1 to 6 carbon atoms; Q represents a partial structure of formula II:

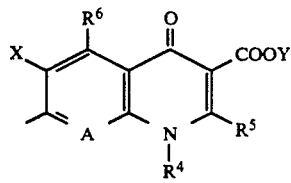

wherein $R^4$ represents an alkyl group of 1 to 6 carbon atoms, an alkenyl group of 2 to 6 carbon atoms, a haloalkyl group of 1 to 6 carbon atoms, a substituted or unsubstituted cycloalkyl group of 3 to 6 carbon atoms, a substituted or unsubstituted aryl group, a 4-pyridyl group, a 2-fluoro-4-pyridyl group, an alkoxy group of 1 to 6 carbon atoms or an alkylamino group of 1 to 6 carbon atoms; $R^5$ represents a hydrogen atom or an alkyl group of 1 to 6 carbon atoms; $R^6$ represents a hydrogen atom, an amino group, a methylamino group, an ethylamino group, an isopropylamino group, a dimethylamino group, a diethylamino group, a hydroxyl group, an alkoxy group of 1 to 6 carbon atoms or a halogen atom; A represents a nitrogen atom or

wherein $R^7$ represents a hydrogen atom, an alkyl group of 1 to 6 carbon atoms, a halogen atom, an alkoxy group of 1 to 6 carbon atoms, a haloalkyl group of 1 to 6 carbon atoms or a cyano group; X represents a halogen atom; Y represents a hydrogen atom, an alkyl group of 1 to 6 carbon atoms, an alkoxyalkyl group of 1 to 6 carbon atoms, a phenylalkyl group containing 1 to 6 carbon atoms in its alkyl moiety, a phenyl group, an acetoxymethyl group, a pivaloyloxymethyl group, an ethoxycarbonyloxy group, a choline group, a dimethylaminoethyl group, a 5-indanyl group, a phthalidinyl group, a 5-substituted-2-oxo-1,3-dioxazol-4-ylmethyl group or a 3-acetoxy-2-oxobutyl group; $R^4$ together with $R^5$, or $R^4$ together with $R^7$ may form a tricyclic ring of the following structure:

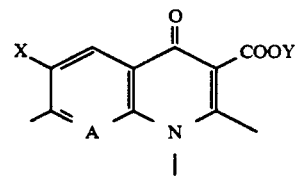

or

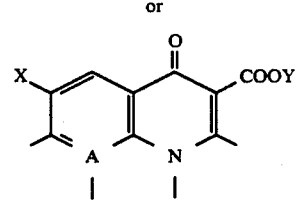

wherein A represents

and X and Y are as earlier defined in this claim; or $R^4$, $R^5$ and $R^7$ may form a tetracyclic ring system of the following formula:

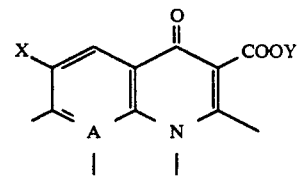

wherein A represents

X and Y are as earlier defined in this claim, and the broken lines represent a monocyclic or bicyclic ring fused to the quinoline ring, which tricyclic or tetracyclic ring is a 4 to 7 membered substituted or unsubstituted carbon-containing ring which can include an oxygen, nitrogen or sulfur atom, wherein if substituted substitution can be on a carbon or nitrogen atom, wherein the substituent is an alkyl group of 1 to 6 carbon atoms or a haloalkyl group of 1 to 6 carbon atoms; and X and Y are as earlier defined in this claim, or a salt thereof; and (B) a pharmaceutically acceptable carrier or diluent.

32. The pharmaceutical composition according to claim 31, wherein said composition comprises an oral dosage form selected from the group consisting of a tablet, powder, granules, capsule, solution, syrup, elixer, oily suspension and aqueous suspension.

33. The pharmaceutical composition according to claim 31, wherein said composition is an injectable solution.

34. The pharmaceutical composition according to claim 31, wherein said composition comprises an external dosage form selected from the group consisting of a solution, suspension, emulsion, ointment, gel, cream, lotion and spray.

* * * * *

UNITED STATES PATENT AND TRADEMARK OFFICE
CERTIFICATE OF CORRECTION

PATENT NO. : 5,286,723
DATED : February 15, 1994
INVENTOR(S) : Isao Hayakawa et al It is certified that error appears in the above-identified patent and that said Letters Patent is hereby corrected as shown below:

Cover sheet, formula I in the ABSTRACT, change

Column 1, formula I, lines 34-43, change

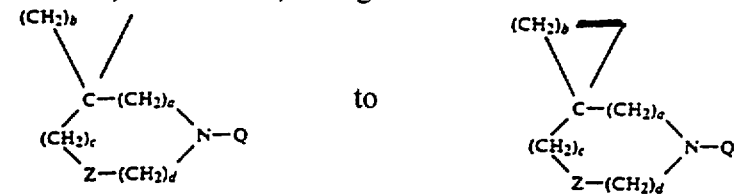

Column 9, formula I, lines 48-55, change

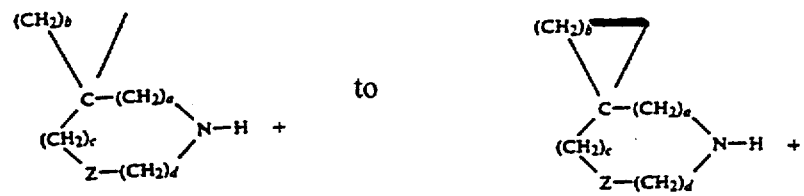

Column 57, first formula, change

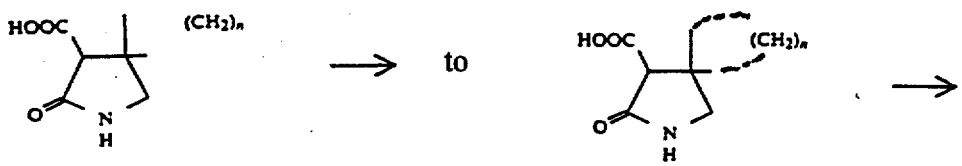

UNITED STATES PATENT AND TRADEMARK OFFICE
CERTIFICATE OF CORRECTION

PATENT NO. : 5,286,723
DATED : February 15, 1994
INVENTOR(S) : Isao Hayakawa et al Page 2 of 3

It is certified that error appears in the above-identified patent and that said Letters Patent is hereby corrected as shown below:

Column 57, second formula, change

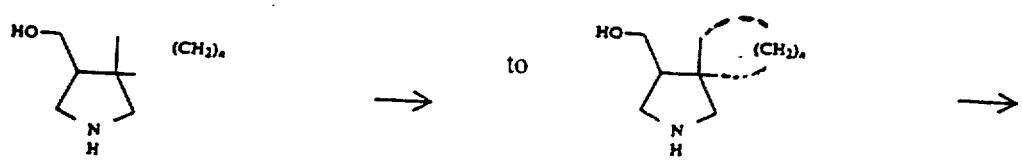

Column 58, first formula, change

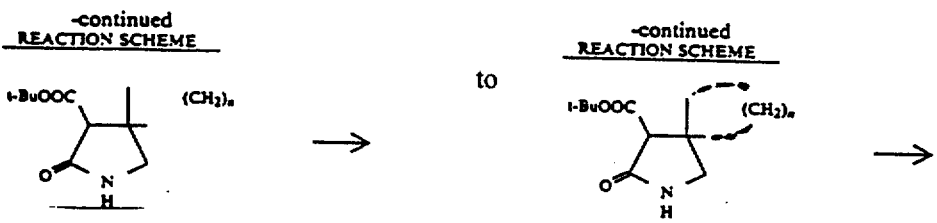

Column 58, second formula, change

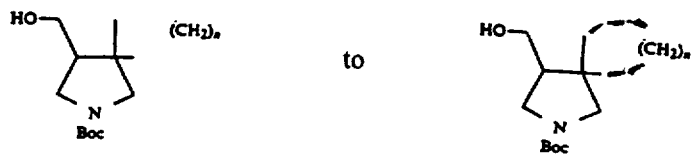

Column 65, formula I in claim 1, change

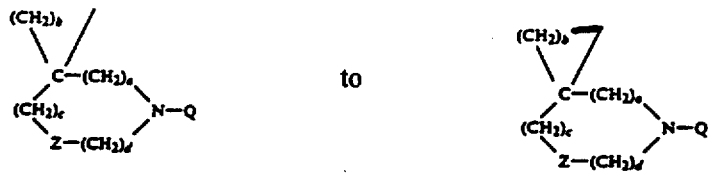

UNITED STATES PATENT AND TRADEMARK OFFICE
CERTIFICATE OF CORRECTION

PATENT NO. : 5,286,723
DATED : February 15, 1994
INVENTOR(S) : Isao Hayakawa et al It is certified that error appears in the above-identified patent and that said Letters Patent is hereby corrected as shown below:

Column 69, formula I in claim 7, change

Column 74, formula I in claim 31, change

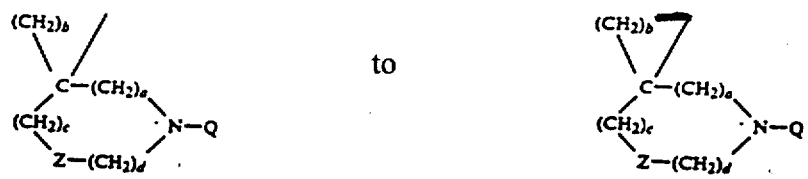

Signed and Sealed this

Twenty-third Day of December, 1997

Attest:

Attesting Officer

BRUCE LEHMAN

Commissioner of Patents and Trademarks